(12) United States Patent
Saliman

(10) Patent No.: US 8,663,253 B2
(45) Date of Patent: Mar. 4, 2014

(54) METHODS OF MENISCUS REPAIR

(75) Inventor: Justin D. Saliman, Los Angeles, CA (US)

(73) Assignee: Ceterix Orthopaedics, Inc., Menlo Park, CA (US)

( * ) Notice: Subject to any disclaimer, the term of this patent is extended or adjusted under 35 U.S.C. 154(b) by 179 days.

(21) Appl. No.: 13/090,089

(22) Filed: Apr. 19, 2011

(65) Prior Publication Data

US 2011/0218557 A1    Sep. 8, 2011

Related U.S. Application Data

(63) Continuation-in-part of application No. 11/773,388, filed on Jul. 3, 2007, now abandoned, and a continuation-in-part of application No. 12/291,159, filed on Nov. 5, 2008, application No. 13/090,089, which is a continuation-in-part of application No. 12/942,803, filed on Nov. 9, 2010, now Pat. No. 8,562,631.

(60) Provisional application No. 60/985,543, filed on Nov. 5, 2007, provisional application No. 60/985,556, filed on Nov. 5, 2007, provisional application No. 61/013,989, filed on Dec. 14, 2007, provisional application No. 61/013,994, filed on Dec. 14, 2007, provisional application No. 61/014,728, filed on Dec. 18, 2007, provisional application No. 61/013,999, filed on Dec. 14, 2007, provisional application No. 61/014,003, filed on Dec. 14, 2007, provisional application No. 61/014,012, filed on Dec. 14, 2007, provisional application No. 61/042,678, filed on Apr. 4, 2008, provisional application No. 61/127,658, filed on May 14, 2008, provisional application No. 61/259,572, filed on Nov. 9, 2009, provisional application No. 61/295,354, filed on Jan. 15, 2010, provisional application No. 61/318,215, filed on Mar. 26, 2010.

(51) Int. Cl.
*A61B 17/04* (2006.01)

(52) U.S. Cl.
USPC .......................................................... 606/145

(58) Field of Classification Search
USPC ......... 606/139, 144, 145, 142, 143, 205–209; 227/175.1–182.1
See application file for complete search history.

(56) References Cited

U.S. PATENT DOCUMENTS 1,037,864 A    9/1912    Carlson et al.
1,815,725 A    7/1931    Pilling et al.
(Continued)

FOREIGN PATENT DOCUMENTS

EP    0647431 A2    4/1995
SU    376089 A    4/1973
(Continued)

OTHER PUBLICATIONS

Saliman et al.; U.S. Appl. No. 13/247,892 entitled "Meniscus Repair," filed Sep. 28, 2011.
(Continued)

*Primary Examiner* — Corrine M McDermott
*Assistant Examiner* — Christopher L Templeton
(74) *Attorney, Agent, or Firm* — Shay Glenn LLP

(57) ABSTRACT

Methods of repairing knee meniscus tears are described which use suture passer devices and suture shuttles. These methods may be used with continuous suture passing, so that the suture passer device may remain on or in the tissue while passing a suture shuttle, and therefore a suture, back and forth from one side of the tissue to the other. These methods may be used minimally invasively for repairing meniscus tissue while avoiding further damage to the meniscus.

17 Claims, 40 Drawing Sheets

(56) References Cited

U.S. PATENT DOCUMENTS

| | | | |
|---|---|---|---|
| 2,738,790 | A | 3/1956 | Todt, Sr. et al. |
| 2,748,773 | A | 6/1956 | Vacheresse, Jr. |
| 3,470,875 | A | 10/1969 | Johnson |
| 3,580,256 | A | 5/1971 | Wilkinson et al. |
| 3,842,840 | A | 10/1974 | Schweizer |
| 3,901,244 | A | 8/1975 | Schweizer |
| 4,021,896 | A | 5/1977 | Stierlein |
| 4,109,658 | A | 8/1978 | Hughes |
| 4,164,225 | A | 8/1979 | Johnson et al. |
| 4,236,470 | A | 12/1980 | Stenson |
| 4,345,601 | A | 8/1982 | Fukuda |
| 4,440,171 | A | 4/1984 | Nomoto et al. |
| 4,484,580 | A | 11/1984 | Nomoto et al. |
| 4,605,002 | A | 8/1986 | Rebuffat |
| 4,621,640 | A | 11/1986 | Mulhollan et al. |
| 4,706,666 | A | 11/1987 | Sheets |
| 4,836,205 | A | 6/1989 | Barrett |
| 4,923,461 | A | 5/1990 | Caspari et al. |
| 4,957,498 | A | 9/1990 | Caspari et al. |
| 4,981,149 | A | 1/1991 | Yoon et al. |
| 5,002,561 | A | 3/1991 | Fisher |
| 5,011,491 | A | 4/1991 | Boenko et al. |
| 5,059,201 | A | 10/1991 | Asnis |
| 5,129,912 | A | 7/1992 | Noda et al. |
| 5,156,608 | A | 10/1992 | Troidl et al. |
| 5,193,473 | A | 3/1993 | Asao et al. |
| 5,211,650 | A | 5/1993 | Noda |
| 5,219,358 | A | 6/1993 | Bendel et al. |
| 5,222,962 | A | 6/1993 | Burkhart |
| 5,250,053 | A | 10/1993 | Snyder |
| 5,250,055 | A | 10/1993 | Moore et al. |
| 5,254,126 | A | 10/1993 | Filipi et al. |
| 5,281,237 | A | 1/1994 | Gimpelson |
| 5,312,422 | A | 5/1994 | Trott |
| 5,330,488 | A | 7/1994 | Goldrath |
| 5,336,229 | A | 8/1994 | Noda |
| 5,342,389 | A | 8/1994 | Haber et al. |
| 5,364,410 | A | 11/1994 | Failla et al. |
| 5,368,601 | A | 11/1994 | Sauer et al. |
| 5,389,103 | A | 2/1995 | Melzer et al. |
| 5,391,174 | A | 2/1995 | Weston |
| 5,397,325 | A | 3/1995 | Della Badia et al. |
| 5,403,328 | A | 4/1995 | Shallman |
| 5,405,532 | A | 4/1995 | Loew et al. |
| 5,431,666 | A | 7/1995 | Sauer et al. |
| 5,437,681 | A | 8/1995 | Meade et al. |
| 5,454,823 | A | 10/1995 | Richardson et al. |
| 5,454,834 | A | 10/1995 | Boebel et al. |
| 5,474,057 | A | 12/1995 | Makower et al. |
| 5,478,344 | A | 12/1995 | Stone et al. |
| 5,478,345 | A | 12/1995 | Stone et al. |
| 5,480,406 | A | 1/1996 | Nolan et al. |
| 5,496,335 | A | 3/1996 | Thomason et al. |
| 5,499,991 | A | 3/1996 | Garman et al. |
| 5,507,757 | A | 4/1996 | Sauer et al. |
| 5,520,702 | A | 5/1996 | Sauer et al. |
| 5,522,820 | A | 6/1996 | Caspari et al. |
| 5,540,704 | A | 7/1996 | Gordon et al. |
| 5,540,705 | A | 7/1996 | Meade et al. |
| 5,562,686 | A | 10/1996 | Sauer et al. |
| 5,569,301 | A | 10/1996 | Granger et al. |
| 5,571,090 | A | 11/1996 | Sherts |
| 5,571,119 | A | 11/1996 | Atala |
| 5,575,800 | A | 11/1996 | Gordon |
| 5,578,044 | A | 11/1996 | Gordon et al. |
| 5,616,131 | A | 4/1997 | Sauer et al. |
| 5,618,290 | A | 4/1997 | Toy et al. |
| 5,626,588 | A | 5/1997 | Sauer et al. |
| 5,632,751 | A | 5/1997 | Piraka |
| 5,643,289 | A | 7/1997 | Sauer et al. |
| 5,645,552 | A | 7/1997 | Sherts |
| 5,653,716 | A | 8/1997 | Malo et al. |
| 5,669,917 | A | 9/1997 | Sauer et al. |
| 5,674,229 | A | 10/1997 | Tovey et al. |
| 5,674,230 | A | 10/1997 | Tovey et al. |
| 5,681,331 | A | 10/1997 | de la Torre et al. |
| 5,690,652 | A | 11/1997 | Wurster et al. |
| 5,709,708 | A | 1/1998 | Thal |
| 5,713,910 | A | 2/1998 | Gordon et al. |
| 5,728,107 | A | 3/1998 | Zlock et al. |
| 5,728,113 | A | 3/1998 | Sherts |
| 5,730,747 | A | 3/1998 | Ek et al. |
| 5,741,278 | A | 4/1998 | Stevens |
| 5,749,879 | A | 5/1998 | Middleman et al. |
| 5,755,728 | A | 5/1998 | Maki |
| 5,759,188 | A | 6/1998 | Yoon |
| 5,766,183 | A | 6/1998 | Sauer |
| 5,792,153 | A | 8/1998 | Swain et al. |
| 5,800,445 | A | 9/1998 | Ratcliff et al. |
| 5,814,054 | A | 9/1998 | Kortenbach et al. |
| 5,824,009 | A | 10/1998 | Fukuda et al. |
| 5,843,100 | A | 12/1998 | Meade |
| 5,843,126 | A | 12/1998 | Jameel |
| 5,865,836 | A | 2/1999 | Miller |
| 5,876,412 | A | 3/1999 | Piraka |
| 5,895,393 | A | 4/1999 | Pagedas |
| 5,895,395 | A | 4/1999 | Yeung |
| 5,897,563 | A | 4/1999 | Yoon et al. |
| 5,899,911 | A | 5/1999 | Carter |
| 5,899,920 | A | 5/1999 | DeSatnick et al. |
| 5,906,630 | A | 5/1999 | Anderhub et al. |
| 5,908,428 | A | 6/1999 | Scirica et al. |
| 5,935,138 | A | 8/1999 | McJames, II et al. |
| 5,938,668 | A | 8/1999 | Scirica et al. |
| 5,944,739 | A | 8/1999 | Zlock et al. |
| 5,947,982 | A | 9/1999 | Duran |
| 5,980,538 | A | 11/1999 | Fuchs et al. |
| 5,993,466 | A | 11/1999 | Yoon |
| 6,048,351 | A | 4/2000 | Gordon et al. |
| 6,051,006 | A | 4/2000 | Shluzas et al. |
| 6,053,933 | A | 4/2000 | Balazs et al. |
| 6,056,771 | A | 5/2000 | Proto |
| 6,071,289 | A | 6/2000 | Stefanchik et al. |
| 6,077,276 | A | 6/2000 | Kontos |
| 6,099,550 | A | 8/2000 | Yoon |
| 6,113,610 | A | 9/2000 | Poncet |
| 6,126,666 | A | 10/2000 | Trapp et al. |
| 6,129,741 | A | 10/2000 | Wurster et al. |
| 6,139,556 | A | 10/2000 | Kontos |
| 6,159,224 | A | 12/2000 | Yoon |
| 6,190,396 | B1 | 2/2001 | Whitin et al. |
| 6,217,592 | B1 | 4/2001 | Freda et al. |
| 6,221,085 | B1 | 4/2001 | Djurovic |
| 6,238,414 | B1 | 5/2001 | Griffiths |
| 6,264,694 | B1 | 7/2001 | Weiler |
| 6,277,132 | B1 | 8/2001 | Brhel |
| 6,322,570 | B1 | 11/2001 | Matsutani et al. |
| 6,325,808 | B1 | 12/2001 | Bernard et al. |
| 6,332,889 | B1 | 12/2001 | Sancoff et al. |
| 6,355,050 | B1 | 3/2002 | Andreas et al. |
| 6,368,334 | B1 | 4/2002 | Sauer |
| 6,443,963 | B1 | 9/2002 | Baldwin et al. |
| 6,454,778 | B2 | 9/2002 | Kortenbach |
| 6,511,487 | B1 | 1/2003 | Oren et al. |
| 6,533,795 | B1 | 3/2003 | Tran et al. |
| 6,533,796 | B1 | 3/2003 | Sauer et al. |
| 6,551,330 | B1 | 4/2003 | Bain et al. |
| 6,585,744 | B1 | 7/2003 | Griffith |
| 6,605,096 | B1 | 8/2003 | Ritchart |
| 6,626,917 | B1 | 9/2003 | Craig |
| 6,626,929 | B1 | 9/2003 | Bannerman |
| 6,638,283 | B2 | 10/2003 | Thal |
| 6,638,286 | B1 | 10/2003 | Burbank et al. |
| 6,641,592 | B1 | 11/2003 | Sauer et al. |
| 6,719,764 | B1 | 4/2004 | Gellman et al. |
| 6,719,765 | B2 | 4/2004 | Bonutti |
| 6,723,107 | B1 | 4/2004 | Skiba et al. |
| 6,770,084 | B1 | 8/2004 | Bain et al. |
| 6,896,686 | B2 | 5/2005 | Weber |
| 6,921,408 | B2 | 7/2005 | Sauer |
| 6,923,806 | B2 | 8/2005 | Hooven et al. |
| 6,923,819 | B2 | 8/2005 | Meade et al. |
| 6,936,054 | B2 | 8/2005 | Chu |
| 6,984,237 | B2 | 1/2006 | Hatch et al. |

(56) References Cited

U.S. PATENT DOCUMENTS

| | | | |
|---|---|---|---|
| 6,991,635 B2 | 1/2006 | Takamoto et al. | |
| 6,997,931 B2 | 2/2006 | Sauer et al. | |
| 6,997,932 B2 | 2/2006 | Dreyfuss et al. | |
| 7,004,951 B2 | 2/2006 | Gibbens, III | |
| 7,029,480 B2 | 4/2006 | Klein et al. | |
| 7,029,481 B1 | 4/2006 | Burdulis, Jr. et al. | |
| 7,041,111 B2 | 5/2006 | Chu | |
| 7,063,710 B2 | 6/2006 | Takamoto et al. | |
| 7,087,060 B2 | 8/2006 | Clark | |
| 7,112,208 B2 | 9/2006 | Morris et al. | |
| 7,118,583 B2 | 10/2006 | O'Quinn et al. | |
| 7,131,978 B2 | 11/2006 | Sancoff et al. | |
| 7,166,116 B2 | 1/2007 | Lizardi et al. | |
| 7,175,636 B2 | 2/2007 | Yamamoto et al. | |
| 7,211,093 B2 | 5/2007 | Sauer et al. | |
| 7,232,448 B2 | 6/2007 | Battles et al. | |
| 7,235,086 B2 | 6/2007 | Sauer et al. | |
| 7,311,715 B2 | 12/2007 | Sauer et al. | |
| 7,344,545 B2 | 3/2008 | Takemoto et al. | |
| 7,390,328 B2 | 6/2008 | Modesitt | |
| 7,442,198 B2 | 10/2008 | Gellman et al. | |
| 7,481,817 B2 | 1/2009 | Sauer | |
| 7,491,212 B2 | 2/2009 | Sikora et al. | |
| 7,588,583 B2 | 9/2009 | Hamilton et al. | |
| 7,594,922 B1 | 9/2009 | Goble et al. | |
| 7,608,084 B2 | 10/2009 | Oren et al. | |
| 7,632,284 B2 | 12/2009 | Martinek et al. | |
| 7,674,276 B2 | 3/2010 | Stone et al. | |
| 7,731,727 B2 | 6/2010 | Sauer | |
| 7,736,372 B2 | 6/2010 | Reydel et al. | |
| 7,749,236 B2 | 7/2010 | Oberlaender et al. | |
| 7,842,050 B2 | 11/2010 | Diduch et al. | |
| 7,879,046 B2 | 2/2011 | Weinert et al. | |
| 7,883,519 B2 | 2/2011 | Oren et al. | |
| 7,938,839 B2 | 5/2011 | DiFrancesco et al. | |
| 7,951,147 B2 | 5/2011 | Privitera et al. | |
| 7,951,157 B2 | 5/2011 | Gambale | |
| 7,951,159 B2 | 5/2011 | Stokes et al. | |
| 7,972,344 B2 | 7/2011 | Murray et al. | |
| 8,394,112 B2 | 3/2013 | Nason | |
| 2003/0023250 A1 | 1/2003 | Watschke et al. | |
| 2003/0065336 A1 | 4/2003 | Xiao | |
| 2003/0065337 A1 | 4/2003 | Topper et al. | |
| 2003/0078599 A1 | 4/2003 | O'Quinn et al. | |
| 2003/0204194 A1 | 10/2003 | Bittar | |
| 2003/0216755 A1 | 11/2003 | Shikhman et al. | |
| 2003/0233106 A1 | 12/2003 | Dreyfuss | |
| 2004/0010273 A1* | 1/2004 | Diduch et al. | 606/144 |
| 2004/0249392 A1 | 12/2004 | Mikkaichi et al. | |
| 2004/0249394 A1 | 12/2004 | Morris et al. | |
| 2004/0267304 A1* | 12/2004 | Zannis et al. | 606/206 |
| 2005/0033319 A1 | 2/2005 | Gambale et al. | |
| 2005/0033365 A1 | 2/2005 | Courage | |
| 2005/0080434 A1 | 4/2005 | Chung et al. | |
| 2005/0090837 A1 | 4/2005 | Sixto, Jr. et al. | |
| 2005/0090840 A1 | 4/2005 | Gerbino et al. | |
| 2005/0154403 A1 | 7/2005 | Sauer et al. | |
| 2005/0228406 A1 | 10/2005 | Bose | |
| 2005/0288690 A1 | 12/2005 | Bourque et al. | |
| 2006/0020272 A1 | 1/2006 | Gildenberg | |
| 2006/0047289 A1 | 3/2006 | Fogel | |
| 2006/0084974 A1 | 4/2006 | Privitera et al. | |
| 2006/0106423 A1 | 5/2006 | Weisel et al. | |
| 2007/0032799 A1 | 2/2007 | Pantages et al. | |
| 2007/0156150 A1 | 7/2007 | Fanton et al. | |
| 2007/0219571 A1 | 9/2007 | Balbierz et al. | |
| 2007/0250118 A1 | 10/2007 | Masini | |
| 2007/0260260 A1 | 11/2007 | Hahn et al. | |
| 2007/0260278 A1 | 11/2007 | Wheeler et al. | |
| 2008/0027468 A1 | 1/2008 | Fenton et al. | |
| 2008/0086147 A1 | 4/2008 | Knapp | |
| 2008/0091219 A1 | 4/2008 | Marshall et al. | |
| 2008/0097489 A1* | 4/2008 | Goldfarb et al. | 606/151 |
| 2008/0140091 A1 | 6/2008 | DeDeyne et al. | |
| 2008/0228204 A1 | 9/2008 | Hamilton et al. | |
| 2008/0234725 A1 | 9/2008 | Griffiths et al. | |
| 2008/0243147 A1 | 10/2008 | Hamilton et al. | |
| 2008/0269783 A1 | 10/2008 | Griffith | |
| 2008/0294256 A1 | 11/2008 | Hagan et al. | |
| 2009/0012538 A1 | 1/2009 | Saliman | |
| 2009/0018554 A1 | 1/2009 | Thorne et al. | |
| 2009/0062816 A1 | 3/2009 | Weber | |
| 2009/0062819 A1 | 3/2009 | Burkhart et al. | |
| 2009/0105751 A1 | 4/2009 | Zentgraf | |
| 2009/0131956 A1 | 5/2009 | Dewey et al. | |
| 2009/0209998 A1 | 8/2009 | Widmann | |
| 2009/0216268 A1 | 8/2009 | Panter | |
| 2009/0228041 A1 | 9/2009 | Domingo | |
| 2009/0259233 A1 | 10/2009 | Bogart et al. | |
| 2009/0306684 A1 | 12/2009 | Stone et al. | |
| 2009/0306776 A1 | 12/2009 | Murray | |
| 2010/0057109 A1 | 3/2010 | Clerc et al. | |
| 2010/0106169 A1 | 4/2010 | Niese et al. | |
| 2010/0114137 A1 | 5/2010 | Vidal et al. | |
| 2010/0121352 A1 | 5/2010 | Murray et al. | |
| 2010/0130990 A1 | 5/2010 | Saliman | |
| 2010/0145364 A1 | 6/2010 | Keren et al. | |
| 2010/0185232 A1 | 7/2010 | Hughett et al. | |
| 2010/0198235 A1 | 8/2010 | Pierce et al. | |
| 2010/0228271 A1 | 9/2010 | Marshall et al. | |
| 2010/0241142 A1 | 9/2010 | Akyuz et al. | |
| 2010/0249806 A1 | 9/2010 | Oren et al. | |
| 2010/0249809 A1 | 9/2010 | Singhatat et al. | |
| 2010/0256656 A1 | 10/2010 | Park | |
| 2010/0280530 A1 | 11/2010 | Hashiba | |
| 2010/0305581 A1 | 12/2010 | Hart | |
| 2010/0305583 A1 | 12/2010 | Baird et al. | |
| 2010/0331863 A2 | 12/2010 | Saliman | |
| 2011/0028998 A1 | 2/2011 | Adams et al. | |
| 2011/0060350 A1 | 3/2011 | Powers et al. | |
| 2011/0087246 A1 | 4/2011 | Saliman et al. | |
| 2011/0112555 A1 | 5/2011 | Overes et al. | |
| 2011/0112556 A1 | 5/2011 | Saliman | |
| 2011/0118760 A1 | 5/2011 | Gregoire et al. | |
| 2011/0130773 A1 | 6/2011 | Saliman et al. | |
| 2011/0152892 A1 | 6/2011 | Saliman et al. | |
| 2011/0251626 A1 | 10/2011 | Wyman et al. | |

FOREIGN PATENT DOCUMENTS

| | | |
|---|---|---|
| SU | 7288848 A1 | 4/1980 |
| SU | 1725847 A1 | 4/1992 |
| WO | WO 98/31288 A1 | 7/1998 |
| WO | WO 03/028532 A2 | 4/2003 |
| WO | WO 03/077771 A1 | 9/2003 |
| WO | WO 2005/037112 A1 | 4/2005 |
| WO | WO 2006/001040 A1 | 1/2006 |
| WO | WO 2006/007399 A1 | 1/2006 |
| WO | WO 2010/036227 A1 | 4/2010 |
| WO | WO 2010/050910 A1 | 5/2010 |
| WO | WO 2010/141695 A1 | 12/2010 |

OTHER PUBLICATIONS

Cayenne Medical; CrossFix® II System (product webpage); 4 pgs.; downloaded Nov. 21, 2011 (www.cayennemedical.com/products/crossfix/).

Smith&Nephew; Fast-Fix Meniscal Repair System (product webpage); 4 pgs.; downloaded Nov. 21, 2011 (http://endo.smith-nephew.com/fr/node.asp?NodeId=3562).

Saliman et al.; U.S. Appl. No. 13/323,391 entitled "Suture passer devices and methods," filed Dec. 12, 2011.

Saliman, Justin D.; U.S. Appl. No. 13/347,184 entitled "Implant and method for repair of the anterior cruciate ligament," filed Jan. 10, 2012.

Arthrex®, Arthrex, Inc., "The Next Generation in Shoulder Repair Technology," Product Brochure from Arthrex, Inc; Naples, Florida, 2007, 22 pages.

ArthroCare® Sportsmedicine, Sunnyvale, CA, SmartStitch® Suture Passing System with the PerfectPasser™, Product brochure, 4 pages.

BiPass} Suture Punch, Biomet® Sports Medicine, Inc., accessed Feb. 29, 2008 at <http://www.arthrotek.com/prodpage.cfm?c=0A05&p=090706> 2 pages.

(56) References Cited

OTHER PUBLICATIONS

Boenisch et al.; Pull-out strength and stiffness of meniscal repair using absorbable arrows or Ti-Cron vertical and horizontal loop sutures; Amer. J. of Sports Med.; vol. 27; No. 5 pp. 626-631; 1999.
Depuy Mitek, Inc; Raynham, MA, "Versalok Surgical Technique for Rotator Cuff Repair: The next generation in rotator cuff repair," Product brochure, 2007, 18 pages.
Linvatec Conmed Company, Largo, Florida, Product descriptions B17-19, B21; Tissue Repair Systems, Tissue Repair Accessories, and Master Arthroscopy Shoulder Instrument Set, 4 pages.
Ma et al; "Biomechanical Evaluation of Arthroscopic Rotator Cuff Stitches," J Bone Joint Surg Am, 2004; 86:1211-1216.
Nho et al; "Biomechanical fixation in Arthroscopic Rotator Cuff Repair," Arthroscopy: J of Arthroscop and Related Surg; vol. 23. No. 1 Jan. 2007: pp. 94-102.
Schneeberger, et al; "Mechanical Strength of Arthroscopic Rotator Cuff Repair Techniques: An in Vitro Study," J Bone Joint Surg Am., 2002; 84:2152-2160.
Tornier, Inc.; CINCH} Knotless Fixation Implant System; 510K (K080335); 6 pgs.; Feb. 6, 2008.
USS SportsMedicine ArthoSewTM Single Use Automated Suturing Device with 8.6 mm ArthroPort Cannula Set, Instructions for Use, <http:www.uss-sportsmed.com/imageServer.aspx?contentID=5020 &contenttype=application/pdf> accessed Apr. 25, 2007, 2 pages.
USS SportsMedicine ArthroSewTM Suturing Device, <http://www.uss-sportsmed.com/SportsMedicine/pageBuilder. aspx?webPageID=0&topicID=7141&xs1=xsl/productPagePrint. xsl>, product description, accessed Apr. 25, 2007, 3 pages.
Saliman, Justin; U.S. Appl. No. 13/062,664 entitled "Knotless suture anchors," filed Mar. 7, 2011.
Saliman, Justin; U.S. Appl. No. 13/114,983 entitled "Suturing and repairing tissue using in vivo suture loading," filed May 24, 2011.
Saliman et al.; U.S. Appl. No. 13/462,760 entitled "Methods of Meniscus Repair," filed May 2, 2012.
Saliman et al.; U.S. Appl. No. 13/462,728 entitled "Devices, Systems and Methods for Meniscus Repair," filed May 2, 2012.
Murillo et al.; U.S. Appl. No. 13/462,773 entitled "Suture Passer Devices and Methods," filed May 2, 2012.
Asik et al.; Strength of different meniscus suturing techniques; Knee Sur, Sports Traumotol, Arthroscopy; vol. 5; No. 2; pp. 80-83; (month unavailable) 1997.
Asik et al.; Failure strength of repair devices versus meniscus suturing techniques; Knee Surg, Sports Traumatol, Arthrosc; vol. 10; No. 1; pp. 25-29; Jan. 2002.
Rimmer et al.; Failure Strength of Different Meniscal Suturing Techniques; Arthroscopy: The Journal of Arthroscopic and Related Surgery; vol. 11; No. 2; pp. 146-150; Apr. 1995.
Covidien Surgical; Endo Stitch 10 mm Suturing Device; accessed Dec. 4, 2012 at <http://www.autosuture.com/autosuture/pagebuilder. aspx?topicID=7407&breadcrumbs=0:63659,30691:0,309:0> 2pages.
MEDSFERA; Suturing devices; accessed Dec. 4, 2012 at <http://www.medsfera.ru/shiv.html> 13 pages.
Duerig, T. et al., "An overview of nitinol medical applications" Materials Science and Engineering A273-275, May 1999.
Saliman et al.; U.S. Appl. No. 13/893,209 entitled "Implant and method for repair of the anterior cruciate ligament," filed May 13, 2013.
Murillo et al.; U.S. Appl. No. 13/893,154 entitled "Suture passer devices and methods," filed May 13, 2013.
Strobel; Manual of Arthroscopic Surgery (1st Edition); Springer Verlag, Hiedelberg © 2002; pp. 127-129; Dec. 15, 2001.
Hirotsuka et al.; U.S. Appl. No. 13/758,994 entitled "Pre-Tied Surgical Knots for Use With Suture Passers," filed Feb. 4, 2013.
McCutcheon et al.; U.S. Appl. No. 13/759,000 entitled "Methods and Devices for Preventing Tissue Bridging While Suturing," filed Feb. 4, 2013.
Saliman, J.; U.S. Appl. No. 13/759,006 entitled "Suture Passers," filed Feb. 4, 2013.
Hendricksen et al.; U.S. Appl. No. 13/844,252 entitled "Suture passers and methods of passing suture," filed Mar. 15, 2013.
Saliman et al.; U.S. Appl. No. 13/873,841 entitled "Devices, systems and methods for meniscus repair," filed Apr. 30, 2013.

* cited by examiner

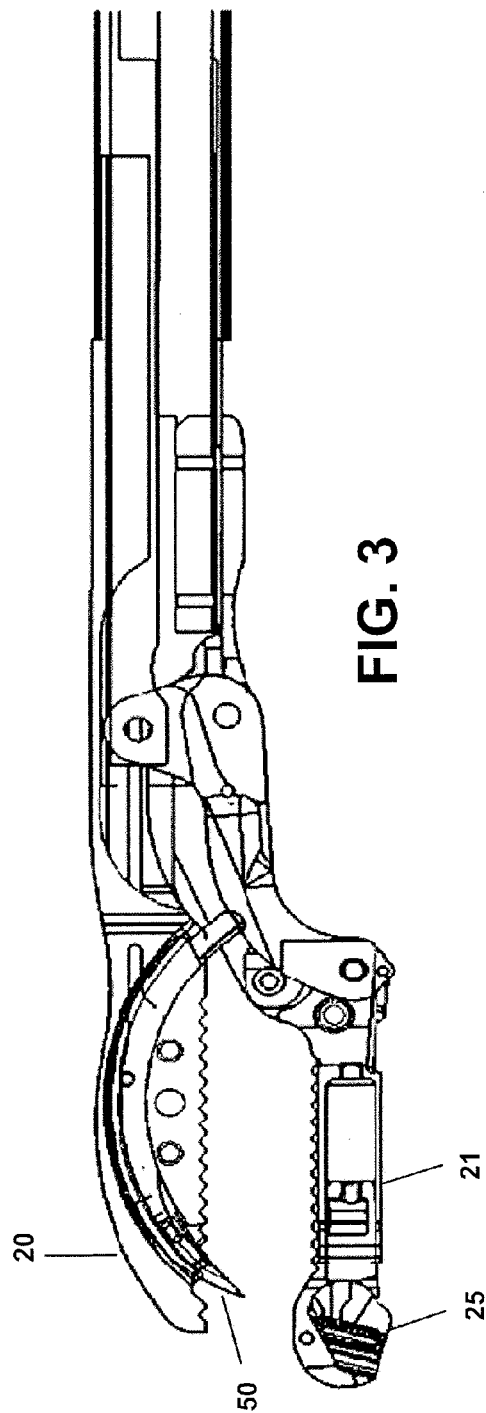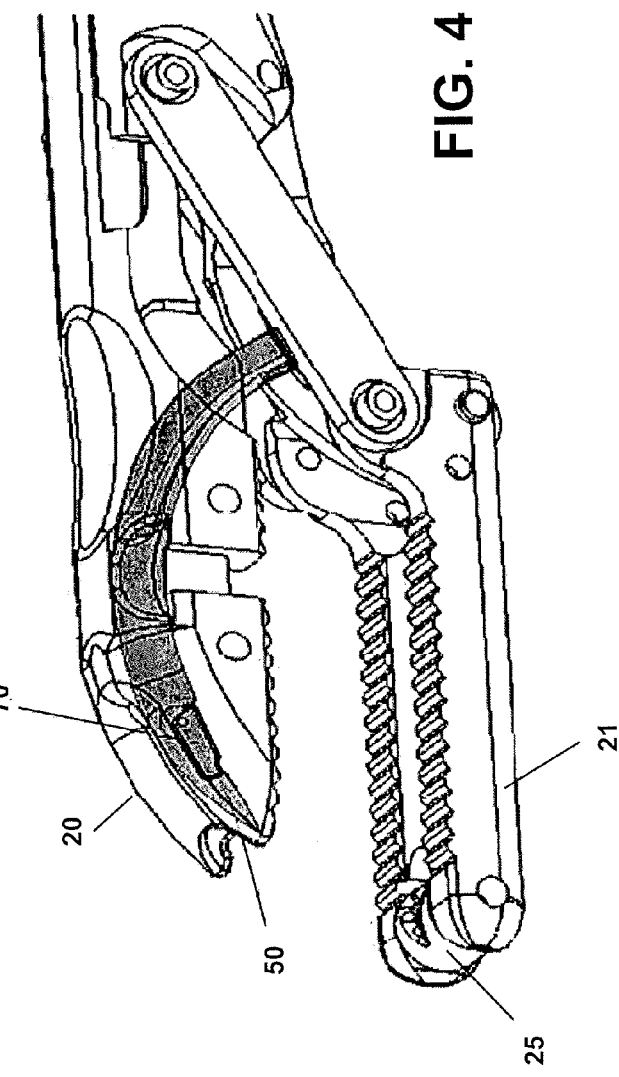

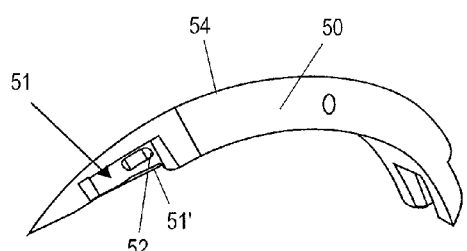
FIG. 8
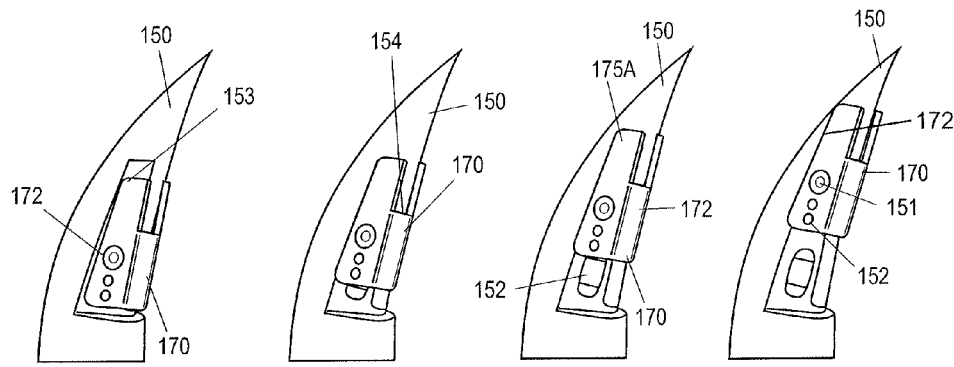
FIG. 9A   FIG. 9B   FIG. 9C   FIG. 9D

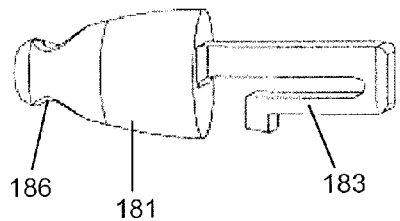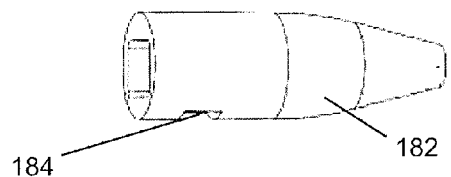
FIG. 11A FIG. 11B
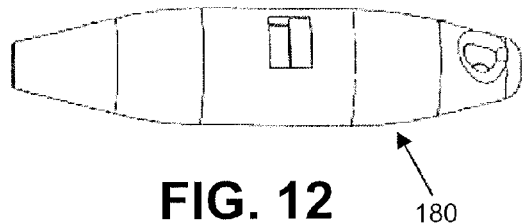
FIG. 12
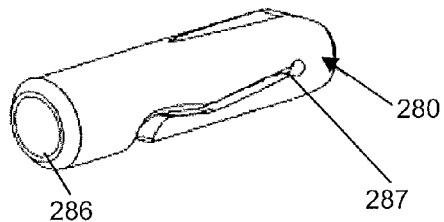
FIG. 13A
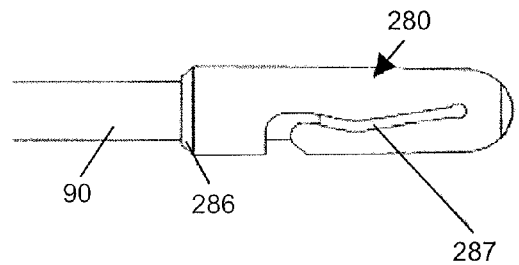
FIG. 13B
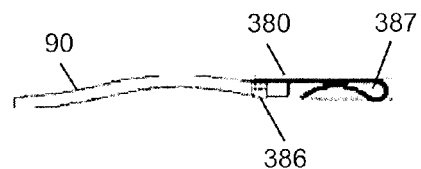
FIG. 14

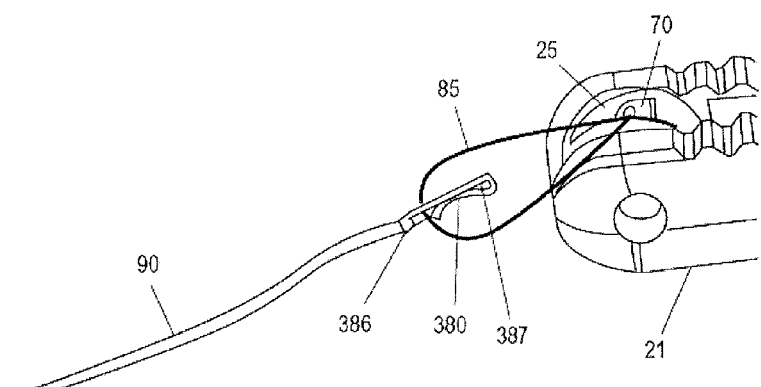
FIG. 15
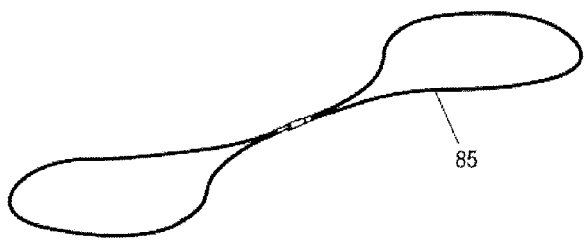
FIG. 16
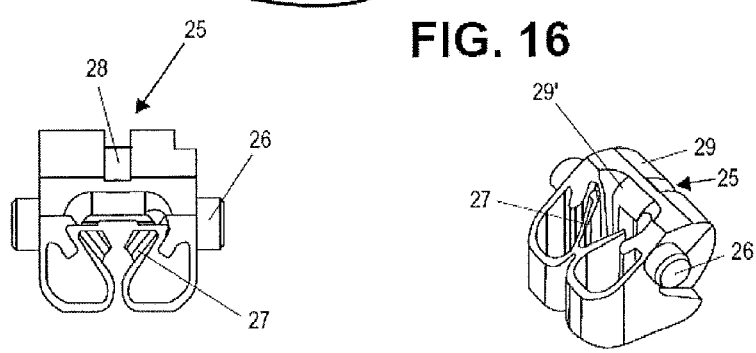
FIG. 17A          FIG. 17B
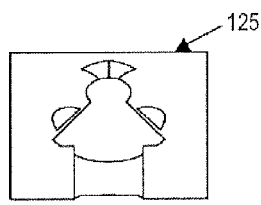     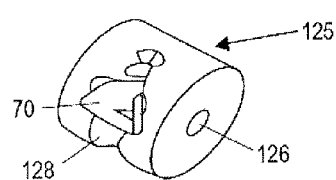
FIG. 18          FIG. 19

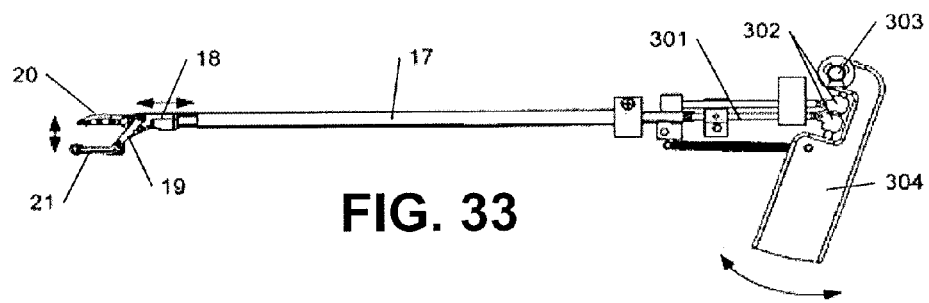
FIG. 33
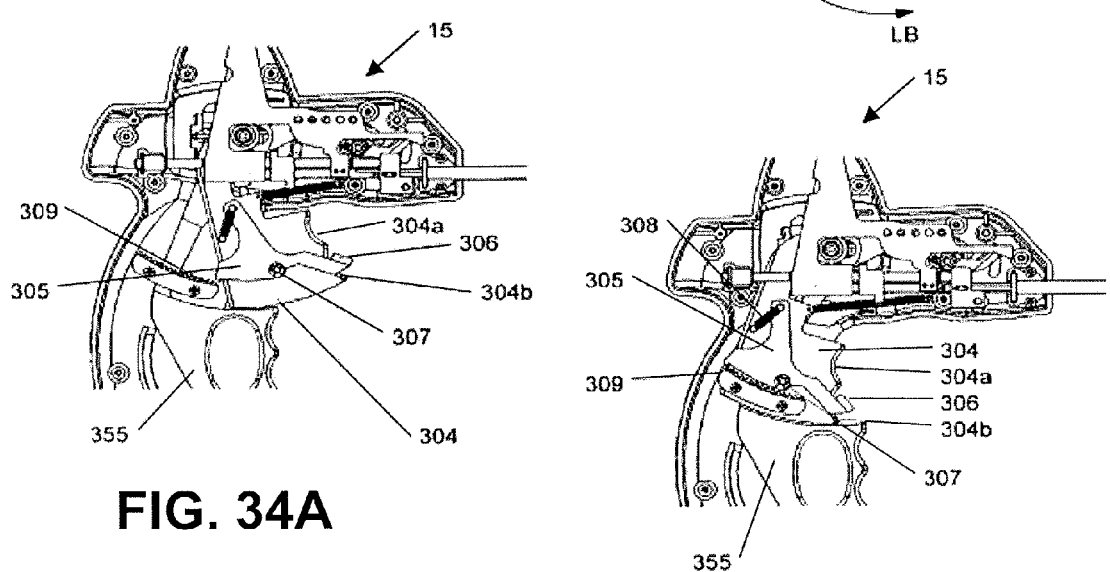
FIG. 34A
FIG. 34B
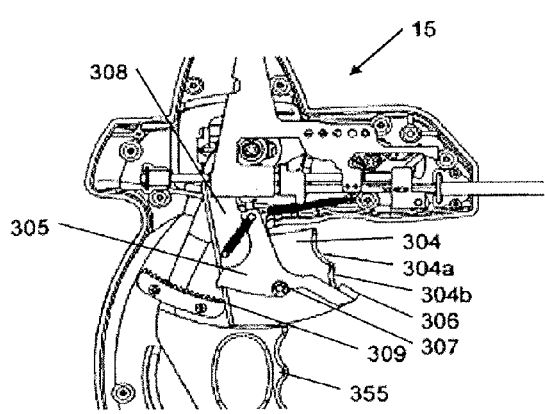
FIG. 34C

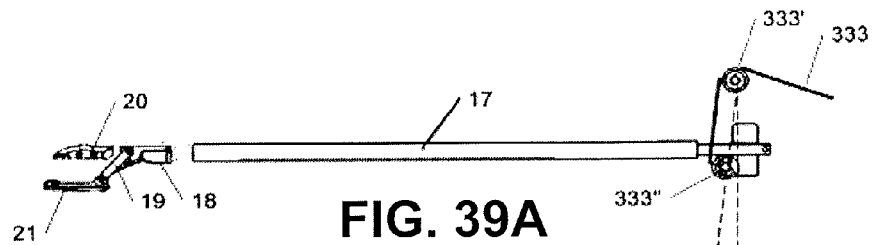
FIG. 39A
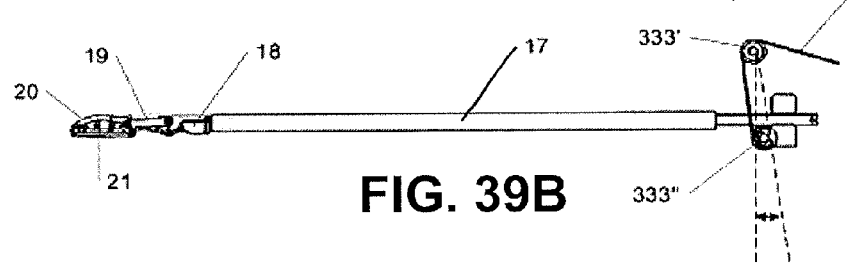
FIG. 39B
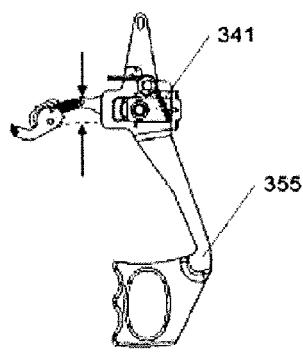 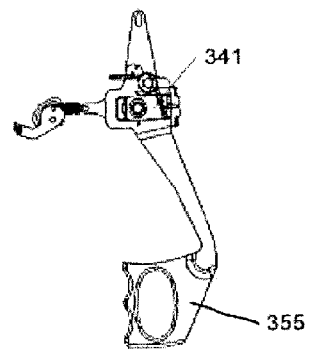 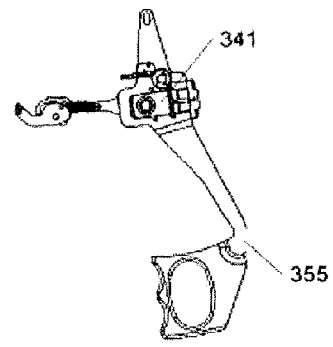
FIG. 40A  FIG. 41A  FIG. 42A
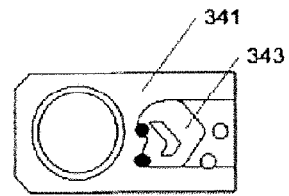 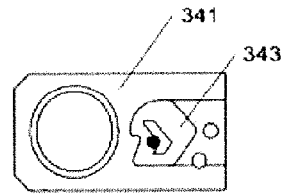 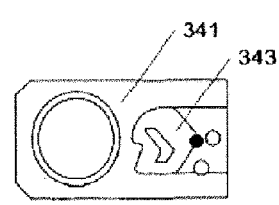
FIG. 40B  FIG. 41B  FIG. 42B

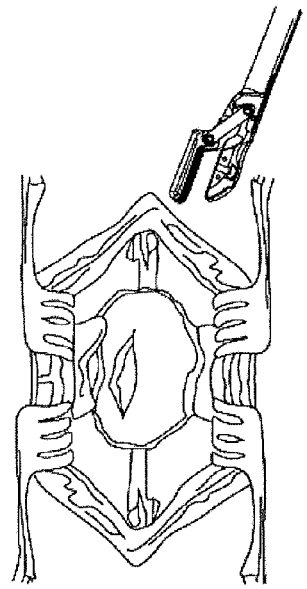 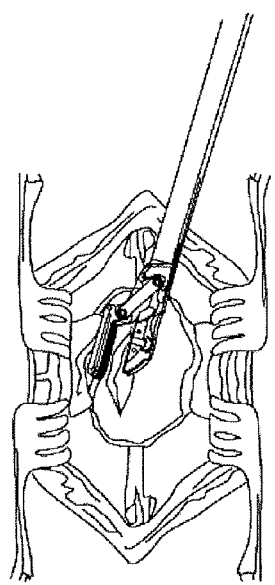 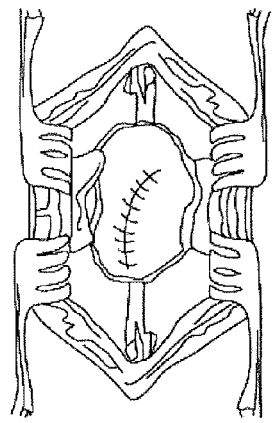
FIG. 57A     FIG. 57B     FIG. 57C
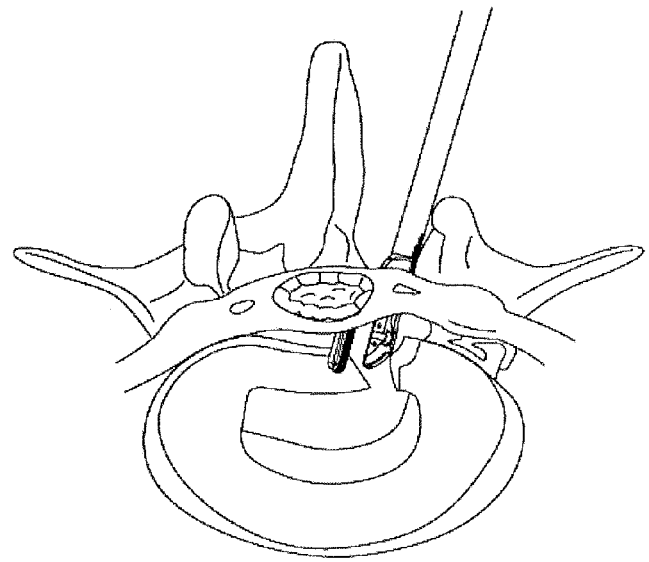
FIG. 58

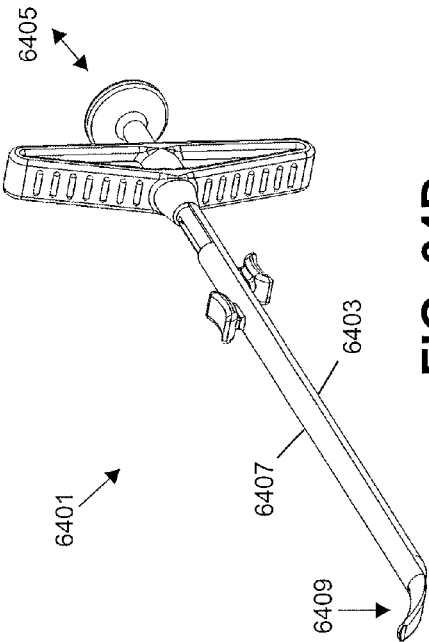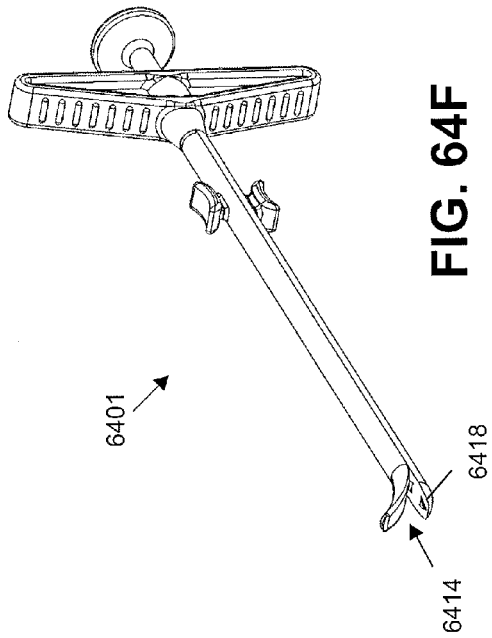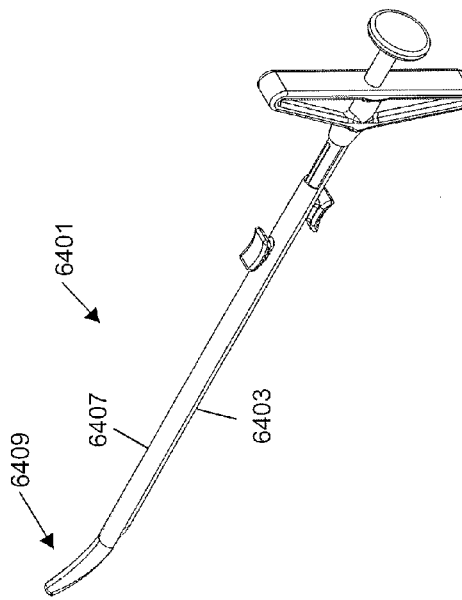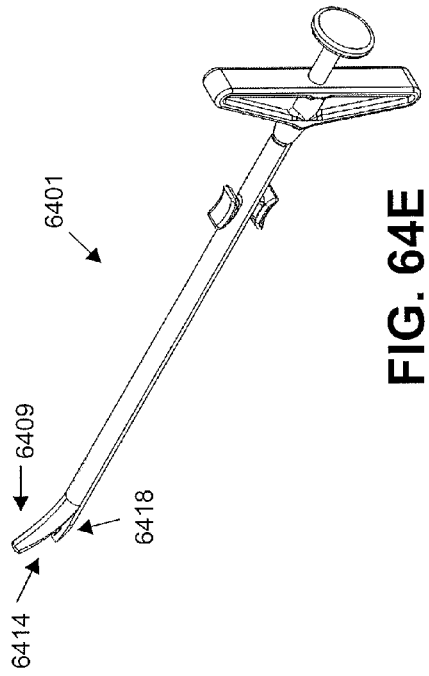

METHODS OF MENISCUS REPAIR

CROSS-REFERENCE TO RELATED APPLICATIONS

This application is a continuation-in-part of U.S. patent application Ser. No. 11/773,388, now abandoned, filed on Jul. 3, 2007, titled "METHODS AND DEVICES FOR CONTINUOUS SUTURE PASSING".

This application is also a continuation-in-part of U.S. patent application Ser. No. 12/291,159, filed on Nov. 5, 2008, titled "SUTURE PASSING INSTRUMENT AND METHOD" which claims the benefit of the filing dates of U.S. Provisional Patent Application Nos. 60/985,543, filed on Nov. 5, 2007; 60/985,556, filed on Nov. 5, 2007; 61/013,989, filed on Dec. 14, 2007; 61/013,994, filed on Dec. 14, 2007; 61/014,728, filed on Dec. 18, 2007; 61/013,999, filed on Dec. 14, 2007; 61/014,003, filed on Dec. 14, 2007; 61/014,012, filed on Dec. 14, 2007; 61/042,678, filed on Apr. 4, 2008; and 61/127,658, filed on May 14, 2008.

This application is also a continuation-in-part of U.S. patent application Ser. No. 12/942,803, now U.S. Pat. No. 8,562,631, filed on Nov. 9, 2010, titled "DEVICES, SYSTEMS AND METHODS FOR MENISCUS REPAIR", which claims the benefit of U.S. Provisional Patent Application Nos. 61/259,572, filed on Nov. 9, 2009; 61/295,354, filed on Jan. 15, 2010; and 61/318,215, filed on Mar. 26, 2010. The full disclosures of each of the foregoing patent applications are herein incorporated by reference as if their entirety.

INCORPORATION BY REFERENCE

All publications and patent applications mentioned in this specification are herein incorporated by reference to the same extent as if each individual publication or patent application was specifically and individually indicated to be incorporated by reference.

BACKGROUND OF THE INVENTION

This invention relates to surgical stitching devices by which a stitch or continuous stitches may be made during surgery.

Suturing instruments for assisting a medical practitioner in placing stitches during surgical procedures are particularly helpful in surgical procedures requiring the placement of secure and accurate sutures in difficult to access regions of the body. Instruments and methods for suturing remotely are especially important in minimally invasive surgical procedures such as laparoscopic and endoscopic procedures. In addition to helping to access remote regions of the body requiring suturing, suturing instruments may also allow the efficient manipulation of very small needles and the formation of small and precise sutures.

The meniscus is a C-shaped piece of fibrocartilage which is located at the peripheral aspect of the joint the knee). The central $2/3^{rds}$ of the meniscus has a limited blood supply while the peripheral $1/3^{rd}$ typically has an excellent blood supply. Young patients typically tear their menisci from traumatic events while degenerative tears are common in older patients as the menisci become increasingly brittle with age. Typically, when the meniscus is damaged, the torn piece begins to move in an abnormal fashion inside the joint, which may lead to pain and loss of function of the joint. Early arthritis can also occur due to these tears as abnormal mechanical movement of torn meniscal tissue and the loss of the shock absorbing properties of the meniscus commonly lead to destruction of the surrounding articular cartilage. Occasionally, it is possible to repair a torn meniscus. While this may be done arthroscopically, surgical repair using a suture may be difficult because of the difficult-to-reach nature of the procedure and the difficulty in placing sutures in a way to compresses and secures the torn surfaces.

Arthroscopy typically involves inserting a fiberoptic telescope that is about the size of a pencil into the joint through an incision that is approximately 1/8 inch long. Fluid may then be inserted into the joint to distend the joint and to allow for the visualization of the structures within that joint. Then, using miniature instruments which may be as small as 1/10 of an inch, the structures are examined and the surgery is performed.

FIGS. 59A-B illustrate the anatomy of the meniscus in the context of a knee joint. As shown in FIG. 60 the capsule region (the outer edge region of the meniscus) is vascularized. A typical meniscus has a flattened ("bottom") and a concave top, and the outer cross-sectional shape is somewhat triangular. The outer edge of the meniscus transitions into the capsule. FIG. 61 illustrates the various fibers forming a meniscus. As illustrated in FIG. 61, there are circumferential fibers extending along the curved length of the meniscus, as well as radial fibers, and more randomly distributed mesh network fibers. Because of the relative orientations and structures of these fibers, and the predominance of circumferential fibers, it may be beneficial to repair the meniscus by suturing radially (vertically) rather than longitudinally (horizontally), depending on the type of repair being performed.

For example, FIGS. 62A-62E, illustrate various tear patterns or injuries to a meniscus. Tears may be vertical/longitudinal (FIG. 62A), Oblique (FIG. 62B), Degenerative (FIG. 62C), including radially degenerative, Transverse or radial (FIG. 62D) and Horizontal (FIG. 62E). Most prior art devices for suturing or repairing the meniscus are only capable of reliably repairing vertical/longitudinal tears. Such devices are not typically recommended for repair of radial tears, particularly not arthroscopically/minimally invasively. FIGS. 63A-63C illustrate sutures placed with prior art devices to repair (via suturing) a torn meniscus (showing a longitudinal tear). FIG. 63A illustrates the results of a repair by a Smith&Nephew "Fast-T-Fix" device (comparable to a repair by a Biomet MaxFire device). FIG. 63B illustrates a Cayanne "CrossFix" device, and FIG. 63C illustrates a repair using an Arthrex meniscal "Viper" device.

In FIGS. 63A-62C the devices affecting these repairs require projection through the meniscus and substantially into the capsule region outside of the meniscus, which could potentially damage the nearby major nerves and large blood vessels. Further, the prior art devices, such as those placing the sutures illustrated in FIG. 63A-63C, typically place horizontal mattress suture patterns rather than vertical mattress suture patterns because vertical patterns are considerably more difficult for surgeons to place when using these devices. Vertical mattress patterns would have improved pull through strength because of the aforementioned predominance of circumferential collagen fibers found within the meniscus structure. Additionally, the devices forming the suture patterns illustrated in FIG. 63A-63C are only capable of point fixation; that is they cannot compress the tears uniformly across the torn surface. Finally, such prior art devices are designed for repairing peripheral vertical meniscus tears (torn from the superior surface to the inferior surface in line with the C-shape of the meniscus) and are incapable of repairing commonly encountered radial meniscus tears.

Thus, there is a need for methods, devices and systems for repairing a torn meniscus that are compatible with effective suturing, in particular, it would be beneficial to provide a device capable of suturing both radial and longitudinal tears. The methods, devices and systems described herein may address this need.

SUMMARY OF THE INVENTION

Described herein are methods for meniscus repair using suture passers. In general, these suture passer devices may be referred to herein as meniscus repair suture passers, meniscus repair devices, or simply suture passers. The devices described herein may be configured to stitch continuously or multiple times.

For example, described herein are methods of repairing or reconstructing a meniscus of a knee, the method comprising: positioning a first arm and a second arm of a suture passer around a meniscus, wherein at least one arm of the suture passer is movable relative to the other arm; extending a tissue penetrator out of the first arm along a first path through the meniscus, and engaging a suture shuttle held by the second arm with the tissue penetrator; retracting the tissue penetrator and suture shuttle back through the meniscus along the first path; repositioning the arms of the suture passer relative to the meniscus; extending the tissue penetrator and suture shuttle from the first arm along a second path through the meniscus and coupling the suture shuttle to the second arm; and retracting the tissue penetrator back through the meniscus along the second path.

The step of extending the tissue penetrator out of the first arm along a first path through the meniscus may include engaging the suture shuttle over a distal end region of the tissue penetrator that is proximal to the distal tip of the tissue penetrator. The shuttle may snap, clip or otherwise engage the distal end region of the tissue penetrator (which may also be referred to as a needle or penetrator). The shuttle may engage with a region of the tissue penetrator proximal to the distal tip of the tissue penetrator; this region of the tissue penetrator may be adapted to retain and/or seat the shuttle.

In some variations, the method of claim 1, wherein repositioning the arms of the suture passer relative to the meniscus comprises moving the suture passer relative to the meniscus without removing the first and second arms of the suture passer from around the meniscus.

The method may also include the step of accessing the meniscus, including minimally invasively accessing the meniscus to position the suture passer. For example, the method may comprise arthroscopically accessing the meniscus to position the suture passer.

In some variations, the first and second paths through the meniscus are curved paths. Thus, the tissue penetrator may be curved or curveable (as it extends from the arm of the suture passer).

In general, the devices and methods described herein may be performed with continuous suture passers, but are not limited to operation with continuous suture passers. In general, the devices are configured to pass a suture from one side of a tissue (e.g., meniscus) to another side of the tissue, and then back from the second side to the first side. Additional stitches or passes may also be (but are not necessarily) performed. In some variations, the step of retracting the tissue penetrator and suture shuttle along the first path comprises retracing the tissue penetrator back into the first arm.

The method may also include a step of connecting a suture to the suture shuttle while the suture shuttle is within the patient. In any of the variations described, the method may include pulling a suture thought the tissue; a suture may be coupled to the suture shuttle as it is passed, or it may be coupled later. For example, the suture shuttle may include a pull element such a leash, wire, loop, string, leader, or the like extending from it that may be passed through the tissue; the suture may be coupled to the end of this pull element and then drawn through the tissue to follow the path taken by the shuttle. Thus, the method may further comprise pulling a suture through the meniscus along the first path (and the second path) where the suture is held within a loop that is connected to the suture shuttle.

The step of positioning the first arm and the second arm around the meniscus may also comprise positioning the meniscus so that a tear in the meniscus is spanned by the first arm and the second arm. Positioning the first arm and the second arm around the meniscus may comprise pushing against the meniscus capsule with one of the first arm or second arm. For example, the capsule may be positioned with one arm so that the second arm can be placed under or around it. For example, the method may include the step of inserting a distal end of the suture passer into the patient's knee and then forming an opening between the first arm and the second arm of the suture passer at the distal end of the suture passer prior to positioning the first arm and the second arm around the meniscus. In some variations, the method further comprises inserting a distal end of the suture passer into the patient's knee and forming an opening between the first arm and the second arm of the suture passer at the distal end of the suture passer by extending the second arm distally relative to the first arm.

Also described herein are methods of repairing or reconstructing a torn meniscus of a knee using a suture passer and a suture shuttle, the method comprising: positioning a first arm and a second arm of a suture passer around at least a portion of a meniscus, wherein at least one arm of the suture passer is movable relative to the other arm; extending a tissue penetrator from the first arm, along a first curved path through the meniscus, and engaging the tissue penetrator with a suture shuttle held by the second arm; retracting the tissue penetrator and suture shuttle back through the meniscus along the first curved path; repositioning at least one arm of the suture passer relative to the meniscus without removing the suture passer from around at least a portion of the meniscus; extending the tissue penetrator and suture shuttle from the first arm along a second curved path through the meniscus and coupling the suture shuttle to the second arm; and retracting the tissue penetrator back through the meniscus along the second curved path leaving the suture shuttle held by the second arm.

The step of repositioning at least one arm of the suture passer relative to the meniscus may comprise moving one arm of the suture passer relative to the other arm. As mentioned, the method may also include minimally invasively accessing the meniscus to position the suture passer (e.g., arthroscopically accessing the meniscus to position the suture passer).

Also described herein are methods of arthroscopic meniscus repair or reconstruction using a suture passer and suture shuttle, the method comprising: accessing the meniscus with a suture passer having a first arm and second arm at the distal end region of the suture passer, wherein at least one of the first and second arms are movable relative to each other to form a distal-facing opening; extending one of the arms distally, relative to the other arm, and positioning the arms of the suture passer around the meniscus; extending a tissue penetrator from within the first arm along a first path through the meniscus, and transferring a suture shuttle held by the second arm onto the tissue penetrator; retracting the tissue penetrator and suture shuttle back through the meniscus along the first path; repositioning at least one arm of the suture passer around the meniscus without removing the meniscus from between the first and second arms; extending the tissue penetrator and suture shuttle from the first arm along a second path through the meniscus, and transferring the suture shuttle from the tissue penetrator to the second arm; and retracting the tissue penetrator back through the meniscus along the second path.

In some variations of the devices described herein, the devices may be configured to repair a meniscus (e.g., knee joint meniscus), and may have two arms which extend longitudinally and can be expanded around a meniscus from a lateral (central) approach. Typically, the distal end region the distal-most 3 or less cm) of one of the arms is bent or bendable at an angle away from the long axis of the device, and the other arm is axially movable distally and proximally (in the direction of the long axis of the device). Extending the distally and proximally movable arm distally will form an acute angled opening at the distal end that can be positioned around the meniscus, and a suture can be passed from one arm to the other through the meniscus or adjacent tissues to repair meniscal tears. The suture may be passed back and forth through the tissue multiple times by using a tissue penetrator that can extend and retract from just one of the arms to move a suture shuttle between the two arms.

In some variations of the devices described herein include suture passer devices and components for continuous suture passing. The devices described herein may include shuttles to which a suture may be attached directly or using an additional clip, for securing a suture when used with a continuous suture passer device. Although, in general, continuous suture passers are capable of passing a suture through a tissue multiple times without having to remove and reload the device, the devices and methods described herein may also be used to pass a suture a single time. In particular, described herein are improved continuous suture passers, particularly suture passers having laws that open and close in parallel, and that are capable of passing a suture when the jaws are open in any position. Any of the devices described herein may be used for continuous stitching and/or knot tying.

In particular, described herein are enhanced devices for continuous (or multiple, or single) suture passing using a shuttle, the device may include elements such as shuttles, tissue penetrators, shuttles having suture attachers, and shuttle retainer seats. Also described herein are methods of treating tissue using a continuous suture passer, which may include some embodiments of suture passers having jaws that open and close substantially parallel to each other, and that are capable of passing a suture and/or shuttle when the jaws are in any position.

In some variations of operation, a suture is passed from the first jaw to the second jaw and/or back from the second jaw to the first jaw. This may be accomplished using an extendable tissue penetrator that is connected to the first jaw. The extendable tissue penetrator can pierce the tissue, and may also engage a suture shuttle (to which a suture may be attached) and thereby pull the suture shuttle through the passage that the tissue penetrator forms in the tissue. Extending the tissue penetrator forms a passage through the tissue, and can also pass the suture between the first and second jaws. For example, the tissue penetrator may include a suture shuttle engagement region, such as, in a cavity within the tissue penetrator, along the outside of the tissue penetrator, or the like, to which the suture shuttle can be releasably attached. The suture can be passed from the tissue penetrator in the first jaw to or from a shuttle retainer seat connected to the second jaw. Thus, both the tissue penetrator and the shuttle retainer seat are configured to releasably secure the suture and suture shuttle. In some variations, the suture passer may pass a suture that is not attached to a suture shuttle. For example, the suture may be knotted, and the knot may be removably held by each jaw of the device.

In one embodiment, a continuous suture passer device may include a first jaw, a second jaw, a tissue penetrator which may penetrate through tissue positioned between the first and second jaws, and a suture shuttle which may be releasably secured to the tissue penetrator and adapted to carry a suture. Further, the device may include an actuator which may manipulate at least one of the first or second jaws and the tissue penetrator, and the second jaw may have a suture shuttle retainer seat on which the suture shuttle may be releasably secured. The tissue penetrator may be movable towards the second jaw such that the suture shuttle carried by the tissue penetrator may be transferred to the shuttle retainer seat on the second jaw. Additionally, the first and second jaws may be substantially parallel to one another at any position to which the at least one jaw is manipulated.

In another embodiment, a continuous suture passer device may include a first jaw and a second jaw; an actuator including a jaw control which may manipulate at least one jaw; and a tissue penetrator which may be configured to travel along an arcuate pathway from the first jaw to the second jaw. Further, the first and second jaws may be substantially parallel to one another at any position to which the at least one jaw is manipulated, and wherein the at least one jaw may be manipulated such that it travels along a path that is substantially the same arcuate path traveled by the tissue penetrator.

In yet another embodiment, a method of passing a suture may include positioning a tissue between a first jaw and a second jaw of a suture passer device, wherein the suture passer includes an arcuate extendable tissue penetrator connected with the first jaw and a shuttle retainer seat which may be connected with the second jaw, wherein a suture shuttle may be releasably held by either the shuttle retainer seat or the tissue penetrator; manipulating at least one of the first jaw and second jaw to secure tissue between them; extending the tissue penetrator through the tissue from a retracted position in the first jaw; transferring the suture shuttle between the shuttle retainer seat and the tissue penetrator; and retracting the tissue penetrator through the tissue and back into the first jaw. Further, the first jaw and second jaw may remain parallel throughout the manipulation.

In a further embodiment, a suture passer device may include a first jaw and a second jaw and a tissue penetrator configured to extend from the first jaw. The device may further include an actuator including a jaw motion control configured to control the motion of the first and second jaws so that at least one of the jaws extends or retracts so that the tissue penetrator extending from the first jaw will contact the second jaw regardless of the position of the at least one jaw. The device may also include a tissue penetrator control configured to extend and retract the tissue penetrator from the first jaw, such that the tissue penetrator control may operate independently of the jaw motion control layer. Additionally, the device may include a retainer pin control which may control a retainer pin, located in the second jaw, independently of the jaw motion control or the tissue penetrator control.

Additionally, the tissue penetrator control may include an alternating stroke limiter, or bi-modal limiter, to alternately pull on a capstan, which may be connected to the retainer pin. Moreover, the tissue penetrator control and retaining pin control may operate independently, but using a single trigger which may include two pivot points: a fixed pivot point and a pin and slot interface which may be a moving pivot. The jaw motion control may include a lock, such as a ratchet mechanism to secure the at least one jaw in place relative to the other jaw.

Described herein are devices and subassemblies for controlling the opening and closing of a pair of jaws of a suture passer device so that the jaws open and close in parallel in a tightly regulated manner, thereby allowing passage of a tissue penetrator from a first jaw so that the tissue penetrator contacts a predetermined target position on the second jaw regardless of the relative positions of the jaws. The devices described herein may include multiple control layers to accomplish the controlled motion. For example, the devices may include a conjugate motion layer having a conjugate motion cam surface, and a tissue penetrator control layer controlling the extension and retraction of the tissue penetrator. In some variations the devices also include a retainer controller layer controls the retention of a suture shuttle. Each of these layers may operate independently of each other. For example, the conjugate motion layer may operate to open and close the jaws independently of the tissue penetrator control layer. Features of the tissue control layer may interact with features of the conjugate motion layer.

The methods of passing a suture described herein may be used to form virtually any number of suture stitches that require multiple passes of the suture through tissue. For example, a modified Mason-Allen stitch may be particularly useful for orthopedic and other applications and may be formed by the methods described herein, using the continuous suture passers. The methods described herein may be used as part of any appropriate medical procedure, including (but not limited to) arthroscopic and endoscopic procedures. Thus, the devices, systems, kits, and methods described herein may be used to repair any appropriate type of tissue. For example, the devices described herein may be used during arthroscopic rotator cuff repair, open or mini-open rotator cuff repair, arthroscopic labral repair (e.g., Bankart repair or anterior-inferior labral repair, SLAP or superior labrum anterior posterior repair, hip labral repair, etc.), arthroscopic biceps tenodesis, arthroscopic capsular plication, rotator interval closure, capsular shift, arthroscopic capsular repair or reconstruction, arthroscopic meniscus repair or reconstruction, open tendon, ligament and muscle suturing, Achilles tendon repair, ACL repair, or the like, in general the devices described herein may be used for general suturing (laparoscopic, endoscopic, thoracoscopic, transoral, open, cutaneous, etc. Examples include: laparoscopic Nissen fundoplication, laparoscopic Rou-en-Y gastric bypass, laparoscopic Herniorrhaphy, laparoscopic Hiatal Hernia Repair, laparoscopic suturing of the uterus, hemonhoidectomy, thoracoscopic esophagectomy, intrathoracic esophagogastric anastamosis, transvaginal sacrospinous colpopexy, vaginal prolaps, incontinence procedures, bladder neck suspensions, laparoscopic dismembered pyeloplasties, fistula tract closure, and the like.

BRIEF DESCRIPTION OF THE DRAWINGS

FIG. 3 illustrates a cross-sectional view of the distal end of one embodiment of the suture passer device.

FIG. 4 illustrates a close-up, perspective view of the distal end of one embodiment of the suture passer device, wherein the upper jaw is transparent.

FIG. 8 illustrates one embodiment of a tissue penetrator.

FIGS. 9A-9D illustrate one embodiment of the interaction between the suture shuttle and the tissue penetrator.

FIGS. 11A-B illustrate another embodiment of the suture clip, split into two pieces.

FIG. 12 illustrates the suture clip of FIGS. 11A-B, but combined to form the complete suture clip.

FIG. 13A-13B illustrates another embodiment of the suture clip.

FIG. 14 illustrates yet a further embodiment of the suture clip.

FIG. 15 illustrates the suture clip of FIG. 14 in use with a suture and suture passer device.

FIG. 16 illustrates another embodiment of a suture linkage wherein the linkage forms a FIG. 8.

FIGS. 17A-17B illustrates a first embodiment of the shuttle retainer seat.

FIG. 18 illustrates a second embodiment of the shuttle retainer seat.

FIG. 19 illustrates one embodiment of the interaction of the suture shuttle and shuttle retainer seat.

FIG. 33 illustrates a first embodiment of a jaw control mechanism.

FIGS. 34A-34C illustrate another embodiment of a jaw control mechanism.

FIGS. 39A-39B illustrate further detail of retainer pin control layer, specifically the communication from the actuator control to retainer pin.

FIGS. 40A-42B illustrate the interaction of one embodiment of the tissue penetrator control layer and one embodiment of the retainer pin control layer.

FIGS. 57A-57C illustrate one example of a dural tear repair using the suture passer device of the present invention.

FIG. 58 illustrates one example of an annulus repair using the suture passer device of the present invention.

FIGS. 64C and 64D show a meniscus repair suture passer from two different side perspective views in which the upper (bent) arm extended and the lower (straight) arm retracted.

FIGS. 64E and 64F show a meniscus repair suture passer after the lower (straight) arm has been extended.

DETAILED DESCRIPTION

Described herein are various embodiments of suture passers for passing a suture through tissue, and components of suture passers that particularly enhance use. In general, the suture passers described herein are continuous suture passers that are configured to pass a suture back and forth through a tissue without having to reload the device. Thus, these devices may be used for continuous stitching of tissue.

Figure 1A:
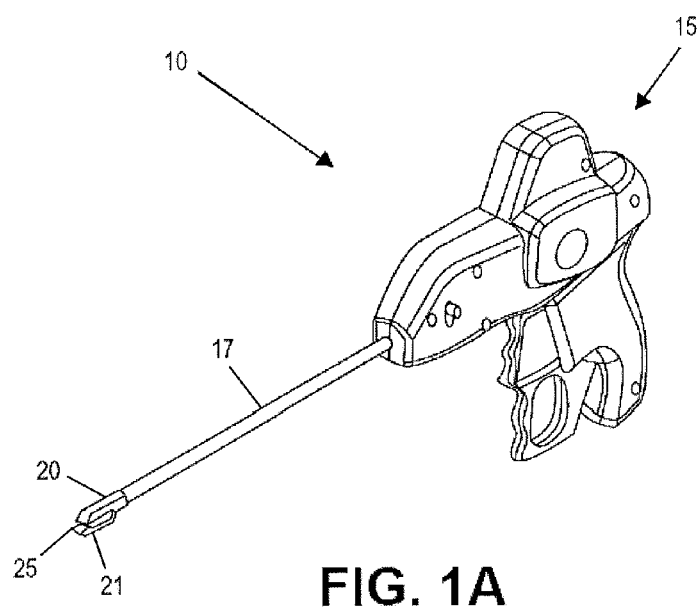
FIG. 1A is a perspective view of a first embodiment suture passer device.
Figure 1B:
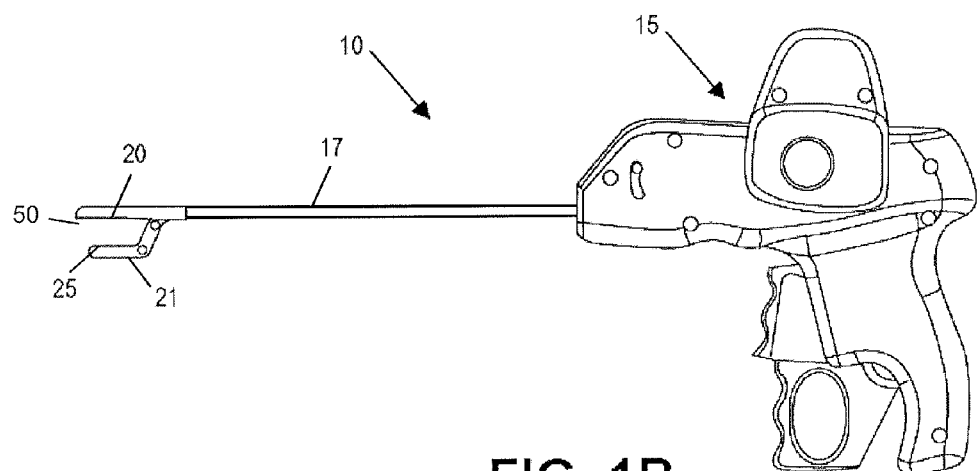
FIG. 1B illustrates a planar view of the suture passer device of FIG. 1A.

FIG. 1A illustrates a first embodiment of a continuous suture passer 10, including some of the enhanced features described herein, which may include, but is in no way limited to, a tissue penetrator (not shown), shuttle (not shown), reciprocating parallel-opening first and second jaws 20 and 21, jaw lock (not shown), and lower-jaw shuttle retainer seat 25. FIG. 1B shows a planar view of the device 10, including the parallel-opening jaws 20 and 21, tissue penetrator 50, and lower-jaw shuttle retainer seat 25.

Figure 2:
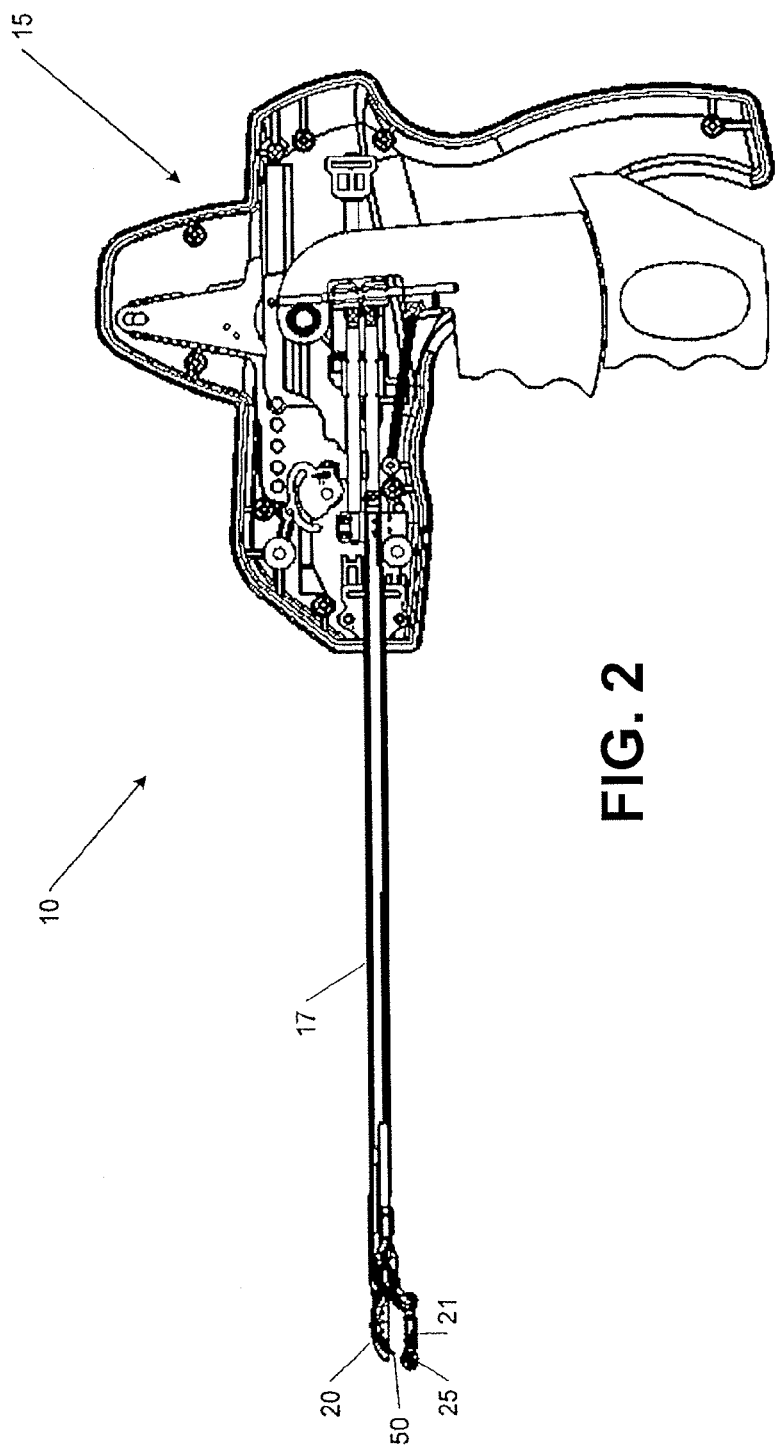
FIG. 2 illustrates a cross-sectional view of one embodiment of the suture passer device.

FIG. 2 illustrates a cross-sectional view of a first embodiment device 10. An actuator portion 15 of device 10 may include the mechanical elements which operate the entire device 10. For example, the actuator 15 includes mechanical elements for movement of at least one of the jaws 20 and 21, movement of the tissue penetrator 50, and retainer pin 30 (not shown), and associated equipment. Actuator 15 may be, in one embodiment, a handle. However, actuator 15 could also be any other type of mechanism to interface the device 10 with a user, such as, a keyboard or remote control for electronic embodiments of the device 10.

FIGS. 3 and 4 show enlarged sectional views of the distal end of device 10. In FIG. 3, one embodiment of the distal portion of device 10 is shown in cross-section. Tissue penetrator 50 is retracted within upper jaw 20, and shuttle retainer seat 25 is positioned near the distal end of lower jaw 21. Tissue penetrator 50 may move from a retracted position, as shown, to an extended position whereby tissue penetrator 50 may move out of the distal end of upper jaw 20 and towards lower jaw 21 and shuttle retainer seat 25.

FIG. 4 illustrates another embodiment of the relationship of tissue penetrator 50 with a shuttle 70. The upper jaw 20 is shown as translucent to uncover detail of tissue penetrator 50 and shuttle 70. Shuttle 70 engages the tissue penetrator such that it can extend from upper jaw 20 along with tissue penetrator 50 towards lower jaw 21 and shuttle retainer seat 25.

FIGS. 5A-7 illustrate various embodiments of shuttle 70, 170 and 270. Shuttle 70, 170 and 270 may be any shape such that it may be releasably attached to tissue penetrator 50. While the shape of shuttle 70, 170 and 270 may correspond to the shape of at least a portion of the tissue penetrator 50 for attachment purposes, it may be of any suitable shape. In these illustrative examples, the shuttle is generally triangular in shape, which may correspond to a tissue penetrator 50 having a generally triangular cross-sectional shape. The illustrated examples of suture shuttles are "channel shuttles" which may engage a tissue penetrator 50. For example, a triangular or cylindrical tissue penetrator 50 may be used, as illustrated in FIGS. 8-9D, to which the suture shuttle 70, 170 and 270 is adapted to connect. Tissue penetrator 50 may be, for example, a needle or any like instrument capable of puncturing through tissue. Shuttle 70, 170 and 270 may be substantially hollow within the triangular shape, and may further have a channel 71, 171 and 271, or opening, along a portion of the triangular body. This channel 71, 171 or 271 may serve as an entry way for tissue penetrator 50 to engage the shuttle 70, 170 and 270. Thus, in these embodiments, the shuttle 70, 170 and 270 wraps around a portion of the tissue penetrator 50, which is positioned within the body of the shuttle.

Figure 5A:
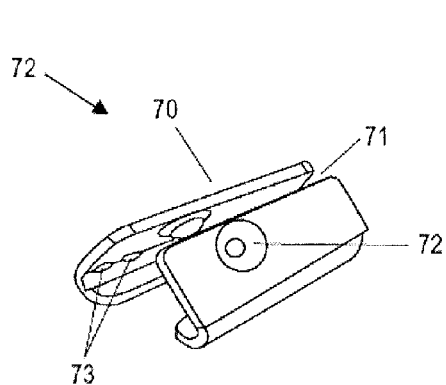
FIGS. 5A and 5B illustrate one embodiment of a suture shuttle.
Figure 5B:
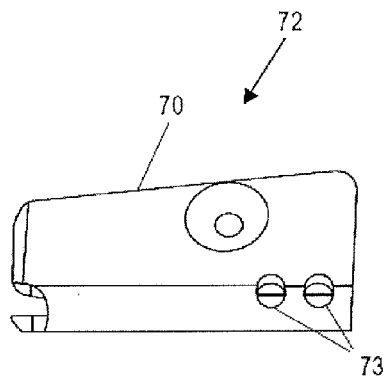
Figure 6A:
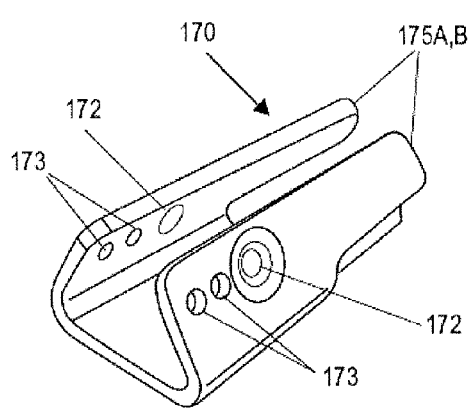
FIGS. 6A and 6B illustrate another embodiment of the suture shuttle.
Figure 6B:
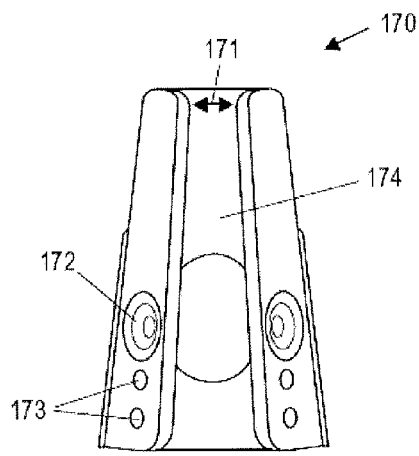
Figure 7:
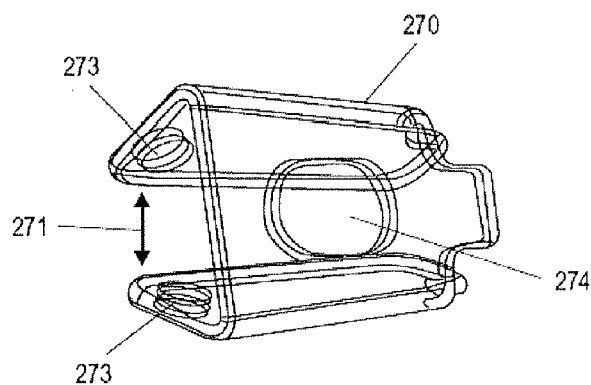
FIG. 7 illustrates yet another embodiment of the suture shuttle.

For example, in FIGS. 5A-B, the channel 71 may be positioned on any portion of the shuttle 70. In the illustrated examples, the channel is positioned along an apex of the triangular shape. However, a channel may also be placed along a side of triangular shape or in any other appropriate place.

Some embodiments of shuttle 170, 270 may also contain openings 74 which may make the shuttle lighter, and may also facilitate flexing of the shuttle so that it can readily attach/detach from the tissue penetrator 50. Further, opening 74 may provide an area through which a retaining mechanism, such as a retainer pin 30, may pass to secure shuttle 170, 270.

Some embodiments of shuttle 70, 170 of the present invention may include additional features which may provide controllable, positive, robust, repeatable, and manufacturable retaining structures. Such features may include, for example, protrusions, such as dimples 72, 172 or the like, and finger springs 175*a* and *b*, both of which may help to retain shuttle 170 on the tissue penetrator 50.

The protruding dimples 72, 172 may interact with divots 52, 152 located within a cut-out 51, 151, or recessed portion, of the tissue penetrator 50. The dimples 72, 172 allow for controllable, repeatable retaining of the shuttle 70, 170 on the tissue penetrator 50, whereby the shuttle may, in a preferred embodiment, snap on and off the tissue penetrator repeatedly, as necessary. In a preferred embodiment, the position of shuttle 70, 170 on the tissue penetrator 50 may be the same given an additional feature such as the dimples and divots. In an alternative embodiment, dimples 72, 172 may be located on the tissue penetrator 50, while the divots 52, 152 may be located on the suture shuttle 70, 170.

In a further embodiment, the cut-out 51, in FIGS. 8-9D, may be configured to seat the shuttle against the outer surface of the tissue penetrator, thereby allowing the tissue penetrator to present a uniform outer surface as it penetrates the tissue; meaning the shuttle does not "stick out" from the tissue penetrator, but is flush with the outer surface of the tissue penetrator. This helps keep the shuttle on the tissue penetrator as it extends from upper jaw 20 and penetrates tissue.

Additionally, in yet a further embodiment, the upper edge 54 of tissue penetrator 50 may be sharpened to provide additional cutting surface on tissue penetrator. In this variation, the shuttle 70 should not interact with the upper edge 54 such that upper edge 54 is exposed to assist in the piercing action of tissue penetrator.

In a further preferred embodiment, tissue penetrator 50 may include an additional cut-out 51' along a portion of tissue penetrator 50 within cut-out 51. Cut-out 51' may allow additional room for a linkage 85 (see FIG. 15, for example). Cut-out 51' may reduce the chance of damage to linkage 85 during tissue penetrator 50 insertion into shuttle 70, since cut-out 51' may provide additional clearance for linkage 85.

In one embodiment, for example in FIGS. 6A-B and 9A-D, finger springs 175*a* and 175*b* may interact with a ramp 153 within the cut-out 151 of the tissue penetrator 150. The finger springs, and even the entire sides of the shuttle 170, may be sloped inwardly towards one end of the shuttle. Thus, in this embodiment, the finger springs are located at the narrowest portion of the shuttle. This slope of the finger springs may interact with the slope of the ramp 153 of the cut-out portion 151. The interaction of these two slopes may regulate the holding force of the shuttle 170 on the tissue penetrator 150 prior to the dimples 172 interacting with the divots 152 to firmly secure the shuttle to the tissue penetrator. Likewise, the holding force is regulated as the shuttle is removed from the tissue penetrator in a similar manner. Thus, when a force is applied to shuttle 170 to pull shuttle 170 off tissue penetrator 150, the finger springs may be forced along the ramp, towards the tip of tissue penetrator, to engage the ramp, causing the finger springs, and thus the sides of the shuttle, to flex apart from one another, and disengage the dimples from the divots.

Continuing with this embodiment, in FIG. 9A, for example, the dimple 172 of the shuttle is engaged with the divot 152 on the tissue penetrator 150. At this point, the finger springs may only be slightly engaged to the tissue penetrator. FIG. 9B illustrates the shuttle 170 beginning to be removed from tissue penetrator. The dimple is no longer in the divot and is instead moving along the surface of the tissue penetrator. The finger springs 175*a* are increasingly engaged onto the tissue penetrator as they move along ramp 153 within cut-out on tissue penetrator. In FIG. 9C, the finger springs are shown as fully engaged with tissue penetrator, particularly at the point where the ramp ends (at the distal end of cut-out portion). This full engagement may, in a preferred embodiment, cause the shuttle to flex, and as a result widen, such that the dimples are no longer in contact with the cut-out portion of the tissue penetrator. FIG. 9D illustrates the final step wherein the dimple and finger spring are no longer touching the tissue penetrator at all, and the tissue penetrator may be retracted, leaving the shuttle 170 free.

Thus, in various embodiments, the tissue penetrator 50 may be adapted to mate with one or more elements on the suture shuttle, whether it is a dimple, or like protrusion, or finger springs, or the like, that can engage with a divot, depression, cut-out or ramp portion on the tissue penetrator.

Shuttle 70, 170 and 270 may be made of any material suitable for use in surgical applications. In a preferred embodiment, the shuttle must have strength, yet also have sufficient flexibility and resiliency to be able to move on and off the tissue penetrator. Such movement requires the shuttle to flex during removal from and addition to the tissue penetrator. Thus, a suitable spring characteristic may be achieved with a high stiffness material, such as steel, by designing the spring such that it has a high preload characteristic when installed relative to the tolerances. For example, one shuttle design illustrated herein may include retention features that are lower spring stiffness & high preload, which may help provide more consistent performance and decrease sensitivity to tolerances. Note that the intrinsic stiffness of the material (Young's modulus) and the spring constant of the shuttle may be related, but may not be equivalent. In addition, these shuttle designs may have significantly reduced tolerance sensitivity, wherein the tolerance is a small percentage of deflection, compared to other shuttle designs. One suitable material may be stainless steel. For example, the shuttle may be composed of 0.004 in. (0.01 mm) thick 17-7 PH stainless steel, Condition CH-900.

Shuttle 70 may be made of material whose hardness is matched to the tissue penetrator 50. Tissue penetrators of a material that is too hard relative to the shuttle may wear the shuttle out. In one example, the tissue penetrator is stainless steel, Rockwell 60C hardness. The shuttle then may be precipitation hardened stainless steel, "17-4 PH", which is also known as stainless steel grade 630. The shape of the shuttle is matched to the shape of the tissue penetrator, and the shuttle clips onto a portion of the tissue penetrator, and can be slipped on and off repeatedly.

The shuttle 70 may be made of a material having a hardness, stiffness and elasticity sufficient so that it may partially elastically deflect to clamp onto the tissue penetrator 50. In particular, we have found that matching the hardness of the shuttle to the hardness of the tissue penetrator may be particularly important for repeated use. For example, the shuttle may be made of Nitinol, beryllium copper, copper, stainless steel, and alloys of stainless steel (e.g., precipitation hardened stainless steel such as 17-7 PH stainless steel), cermet (ceramic and metal), various polymers, or other biocompatible materials. The material chosen may be matched to the material of the tissue penetrator for various properties including, for example, hardness and the like. The shuttles may be formed in any appropriate manner, including punching, progressive die, CNC, photolithography, molding, etc.

In the above examples, a pull-out force, or the force required to remove the shuttle 70 from the tissue penetrator 50, may be more than about 2 pounds of force. Preferably, the force may be about 2 to about 5 pounds. The force may be from, for example, the pulling of a suture, or suture clip or connector, attached through one of the bore holes 73 located on shuttle 70. This force should be from the direction of about the tip of the tissue penetrator.

In a preferred embodiment, illustrated in FIGS. 5A-B, the bore holes 73 are located away from channel 71 and towards the base of the triangle, which may be in a fold in the shuttle, as shown in FIG. 5B. In the other illustrated embodiments, FIGS. 6A-7 for example, the bore holes 173 are adjacent the channel. FIGS. 5A-B illustrate a position of bore holes 73 which may reduce, or even eliminate, the bending forces on the sides of shuttle 70, when suture, or the like, applies a force at bore holes 73. Typically, when bore holes 73 are located adjacent channel, as in FIG. 6A, the bending force on the side of the shuttle may peel the shuttle from the tissue penetrator 50 at a force lower than the desired removal force, due to the advantage of the force being applied to a corner of the shuttle 70. However, bore holes 73 located as shown in FIG. 5B limits this bending force, or torque, and thus prevents removal of shuttle 70 from tissue penetrator 50 at a premature time and at a force less than is desired for removal of shuttle 70.

In another embodiment, the shuttle 70 may be in the shape of a spiraled wire, or the like, such as a "finger torture" type device, whereby as the shuttle is pulled by the tissue penetrator 50, the shuttle may tighten around, thereby securing itself to the tissue penetrator. The stronger the force of the pull, the tighter the spiraled wire secures to the tissue penetrator. When the shuttle is to be transferred from the tissue penetrator, for example, to the shuttle retainer seat 25, the shuttle may be twisted, or the like, to "unlock" the shuttle from the tissue penetrator.

Other examples of shuttles 70, which may be able to clamp onto the tissue penetrator to secure itself, may be torsion springs, snap rings, a portion of wire, elastically deformable shapes, conically tapered shapes, and the like. Elastically deformable shapes may be any shape desired, such that it can be deformed to wrap around at least a portion of the tissue penetrator. Useful shapes may include, but are not limited to, cylinders, triangles, overlapping rings, and any partial portion of a shape such as a semi-circle. Once the tissue penetrator is in position, the shape of the tissue penetrator receiving area allows the elastically deformable shape to return to its original configuration while being securely attached to the tissue penetrator. Of course, the cut-out 51, or recess, or receiving area, on the tissue penetrator may in a preferred embodiment be shaped such that it coincides with the shape of the shuttle. For example, if a conically tapered shuttle were used, the tissue penetrator may include a conically tapered cut-out on a portion of the surface. The conically tapered shuttle may be deformable, and may deform upon being moved into the cut-out. Once completely within the cut-out, the conically tapered shuttle would return to its original shape and secure itself within the cut-out. The cut-out may include, for example, a lip, or the like, to assist in securing the shuttle, fully or partially, within the cut-out.

In other embodiments, the shuttle may constitute the tip of the tissue penetrator 50 itself, such that the tip may be releasably coupled on the end of the tissue penetrator. Thus, the tip of the tissue penetrator may be passed between jaws of the suture passer device to pass the suture, which suture is attached to the tip, back and forth through the tissue.

Suture 90 may, in one embodiment, be attached directly to shuttle 70 at bore hole 73, or other like retention location. Of course, suture need not be secured only by a bore hole. Instead, suture may be secured to shuttle by adhesive, a clamp, by being ties or engaged to a portion of the shuttle, or in any other suitable manner.

Additionally, suture 90 may be secured to shuttle 70 via an intermediary device, such as the various examples in FIGS. 10-15. One such intermediary device may be a suture clip, or suture retainer, 80, 180, 280 or 380. A suture clip allows for simple and efficient releasable connection of a suture to a shuttle. A suture clip may be used for continuous suture passing, or alternatively for single passing of a suture.

In operation, suture clips 80, 180, 280, or 380, some examples of which are illustrated in FIGS. 10-15, may be used as part of a system for suturing tissue, particularly when used with a continuous suture passer 10. For example, a suture 90 may be passed from the first jaw 20 to the second jaw 21 and/or back from the second jaw to the first jaw of a suture passer. This may be accomplished using an extendable tissue penetrator 50 that is connected to the first jaw. The extendable tissue penetrator can pierce the tissue, and can also engage a suture shuttle 70, to which a suture is attached through the suture clip 80, 180, 280, 380. The suture may then be pulled through the passage that the tissue penetrator forms in the tissue. Extending the tissue penetrator forms a passage through the tissue, which may also pass the suture between the first and second jaws. For example, the tissue penetrator may include a suture shuttle engagement region which may be, for example, a cavity within the tissue penetrator, along the outside of the tissue penetrator, or the like, to which the suture shuttle can be releasably attached. The suture can be passed from the tissue penetrator in the first jaw to or from a suture shuttle retainer seat 25 connected to the second jaw. Thus, in a preferred embodiment, both the tissue penetrator and the suture shuttle retainer seat are configured to releasably secure the suture, which may be attached to a suture shuttle.

In some variations, the suture clip 80, 180, 280, 380 described herein may include an attachment linkage 85 to a suture shuttle 70, for example a tether, leash, lead wire, or the like, which may be configured to connect the suture clip to the shuttle. In some examples, the suture clip includes a bias, for example, a spring, for securing a linkage 85 within a snap-fit element. Alternatively, the suture clip may include a central opening through which a linkage may be threaded. This linkage can act as a spacer. In one embodiment, the linkage may be stiffly attached to the shuttle 70 such that it both spaces the shuttle from the suture and also controls the position of the shuttle based on a force exerted on the linkage. The linkage will also control the position of the suture as the shuttle is passed from one jaw to the other.

Similarly, the linkage 85 may be a stiff metallic wire, a portion of suture, a flexible polymeric strand, or the like. In the example of a stiff metallic wire, the wire may be welded to the shuttle such that it may project from the shuttle in a predictable manner.

Figure 10:
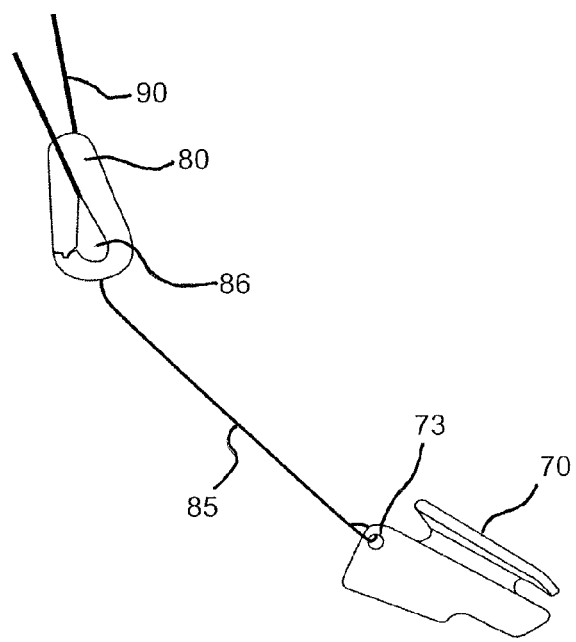
FIG. 10 illustrates a first embodiment of a suture clip.

In one embodiment, illustrated in FIG. 10, the shuttle 70 may be connected to a suture clip 80 that may be a compressed loop, in which the compressed loop has an inner, generally "teardrop" shaped opening 86 that is wider in one end than the other. The suture 90 may then be threaded through the inner loop 86 such that it becomes wedged within the narrow portion of the teardrop shape. The suture may then be secured by any method known in the art such as by tying a knot or bringing the end outside of the body. The suture may also be secured solely by being wedged within the teardrop shape, which may be sufficient to secure the suture within the suture clip.

In an alternative embodiment, the suture clip may be a ring, which may have a circular outer shape and a circular inner opening. In this example, the suture would be passed through the circular inner opening and secured by any method known in the art such that the suture is not easily separable from the suture clip.

In another embodiment, the suture clip 180, illustrated in FIGS. 11-12, may be a two-piece assembly that snaps together. The first piece 181 may include a connector 186 for one of the suture 90 or linkage 85, while the second piece 182 may include a connector for the other of the suture 90 or linkage 85. For example, a suture may be formed onto the second piece 182, or knotted onto the second piece, or the like. The first and second pieces are configured to be secured together. In some variations, the first and second pieces are configured to be releasably secured together. For example, the first and second piece may be snapped together, but may include a releasable securing element 183, such as a button or the like, for separating them.

In FIGS. 11A-B, the suture clip 180 is shown with the first and second pieces 181 and 182 forming the clip 180 when connected together. The clip 180 may be configured so that it may readily pass through tissue. For example, the shape may be smooth, and may be tapered along the axis of its length. The surface may be lubricious or otherwise coated. Other shapes are possible.

This "snap-fit" example of a suture clip also may include a suture retaining location on either of the pieces, or, alternatively, in between the two pieces. A lead wire, or other extension, may be secured within the eyelet 186, or alternatively on the tip of the second piece 182, or also secure in between the two pieces.

The clip 180 may be separated into the first and second pieces by releasing the securing element 183 between the two pieces. The first and second pieces of the assembly may also be referred to as "male" and "female" components. In the example shown in FIGS. 11A-B, the pieces may be separated by applying pressure through the window region 184, releasing the securing element that holds the two pieces together. Snapping the first and second pieces together to from the assembly shown in FIG. 12 causes the securing element to engage and hold the first and second pieces together. The securing element may be disengaged by applying pressure. For purposes of simplicity, in a preferred embodiment, the first and second pieces do not include either a suture or an attachment linkage to the shuttle. It should be understood that these components may be included.

For example, the securing element 183, and the clip 180 as a whole, may be made of a plastic polymeric material, a metal, or the like. Although the latch is shown extending from the first piece 181, it may alternatively extend from the second piece 182. More than one latch may be used. Also, alternative variations of the latch may also be used.

The suture 90 and/or linkage 85 may be glued, heat-staked, or otherwise attached permanently or semi-permanently to the second piece 182. In some variations the suture may be knotted. For example, the suture or linkage may be attached to the second piece 182 by first threading the end of the suture through the hollow second piece and then knotting the suture; the larger-diameter knot will be retained by the second piece since the suture knot cannot pass through the tapered or smaller-diameter opening or passage in the second piece. In some variations the second piece may be pre-threaded with a suture.

In use, a surgeon can easily snap the two pieces together, and the assembly may pass through the tissue with minimal drag. As mentioned, the assembly can be separated back into the first and second pieces by releasing the latch, if necessary. The latch may be released manually, or by using a special tool configured to disengage the latch. For example, a disengaging tool may be used to clamp on the assembly in the proper orientation and to apply pressure to release the latch.

In a further embodiment, illustrated in FIG. 13A-B, the clip 280 may be a piece of tubing which has been laser cut to accommodate suture 90 and linkage 85 connections. In a preferred embodiment, clip 280 may be crimped securely to suture at suture-attachment element 286. Linkage 85 may be secured within the laser cut path 287. Additionally, suture 90 may protrude into central region of clip 280 to interact with linkage 85, which may also secure linkage 85 within laser cut path 287. Epoxy, or the link, may also be used to secure linkage in clip 280. The laser cut path 287 need not be formed by a laser, but may be machined in other ways known in the art. Alternative embodiments may exist where the linkage 85 is connected to position 286 and suture is connected to position 287. Additionally, linkage 85 may include a second portion of a suture.

In yet another embodiment, the suture clip 380 may include a flexible planar structure that is looped back on itself. This type of clip may be attached to an end of the suture, as illustrated in FIGS. 14-15. One end of the clip, which may include a suture-attachment element 386, may be secured to the end of the suture 90. The suture-attachment element may be crimped to the suture and may be polymeric tubing, such as cyanoacrylate and polyester, for example. The opposite end of the clip may be folded over itself to form a latch 387 within which a suture, wire or the like may be placed. The clip is secured to the suture at the suture-attachment element, and is latched to a wire loop 85 which is attached to the shuttle. Of course, the clip may be reversed such that the clip engages the suture rather than the wire loop. Alternatively, of course, the wire may be replaced by an additional suture or the like.

In yet another embodiment, illustrated in FIG. 16, the linkage 85 may be a wire loop. The wire may include nitinol. For example, FIG. 16 shows a wire loop linkage 85 bonded in the middle to form a double-loop construction, having at least two loops, or in a preferred embodiment, a "Figure-8" shape. A double-loop or a Figure-8 shape may provide additional safety in that if any portion of the wire loop linkage 85 fails, the linkage remains fixed to at least one of the suture clip 80 or the shuttle 70. Conversely, a wire loop linkage looped through both the clip 80 and shuttle 70, as a mere loop of wire, may fall into the body upon failing. In arthroscopic applications, this may create a dangerous situation for the patient.

One embodiment of suture passer devices 10 may include a seating region 25 into which the tissue penetrator engages. This region may be referred to as a seat, a tissue penetrating engagement region, or a shuttle retainer seat. For example, the suture passers described in the Ser. No. 11/773,338 patent application (previously incorporated by reference) as well as provisional patent application U.S. Ser. No. 60/985,543 (herein incorporated by reference in its entirety) form a cavity or opening into which a tissue penetrator 50 can be inserted. In these devices, in a preferred embodiment, a suture shuttle 70 is passed between the tissue penetrator 50 and the seat 25, although shuttleless variations (as described below) may also include a seat region for engaging the tissue penetrator and suture 90.

FIGS. 17-19 illustrate various embodiments of the shuttle retainer seat 25, 125. The shuttle retainer seat may be positioned with respect to the tower jaw 21, and in a preferred embodiment, within the lower jaw 21 as shown. Hole and pin 126, 26, respectively, may be for the attachment of a stiff member 32' which may rotate the shuttle retainer seat to substantially match the motion, or angle of approach, of the tissue penetrator 50, such that the shuttle retainer seat is moved to substantially match the angle of penetration of the tissue penetrator into the shuttle retainer seat. The amount of motion required may be dependent upon the distance the jaws 20 and 21 are spread apart. Thus, no matter the distance between jaws 20 and 21, the shuttle retainer seat may move complimentary to any direction from which the tissue penetrator 50 is extending from jaw 20 towards jaw 21 and shuttle retainer seat 25, 125. Opening 28, 128 in the suture retaining seat provides a throughway for a set screw or a retaining pin, for example, which may secure the shuttle 70 within the suture retaining seat.

FIG. 19 illustrates, in one embodiment, an example of the interaction of the shuttle 70 and the shuttle retaining seat 125. The shuttle is lodged within the central cavity of shuttle retaining seat. The tissue penetrator may then enter through the central bore of both shuttle and shuttle retainer seat to retrieve the shuttle.

In another embodiment, illustrated in FIGS. 17A-B, the shuttle retainer seat 25 may include flexible seat portions 27, which may contact two sides of shuttle 70, while providing additional clearance for shuttle and tissue penetrator during insertion and removal. The flexible seat portions 27 may provide dynamic clearance for expanding shuttle sides, during release from tissue penetrator 50, thus accommodating shuttle flexure. Further, the device 10 may be more reliable because the flexible seat portions may lessen any effects of high forces during the seating process.

When these devices are used with some tissue, especially softer, tissue may prolapse into the seat as the tissue is secured between the jaws. This prolapsed tissue may prevent complete penetration by the tissue penetrator, and may also interfere with the operation of the suture passer. In order to prevent the tissue from entering the inner portion of the seat, the shuttle retainer seat 25 may include prominent side walls against which the tissue may be pressed by the collapsing of jaws 20 and 21 around the tissue. The side walls may stretch the tissue, or assist is pulling it taught, to prevent the tissue from prolapsing into the seat where the shuttle is retained. Maintaining pressure on the tissue during puncturing with the tissue penetrator may also form a cleaner cut by the tissue penetrator. These anti-prolapse features may also be incorporated into the non-moving lower jaw component 21 or on the upper jaw 20, rather than on the shuttle retainer seat 25, with spreading features disposed on each side of the shuttle retainer seat.

Figure 20A:
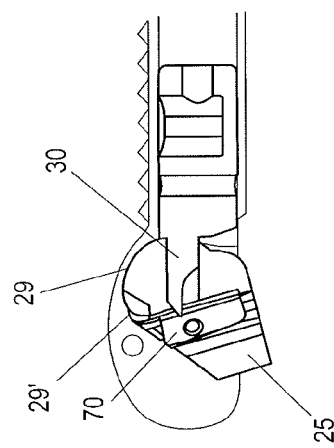
FIGS. 20A-20B illustrate, in cross-section of a lower jaw, one embodiment of the interaction of the suture shuttle, shuttle retainer seat, and a retaining pin.
Figure 20B:
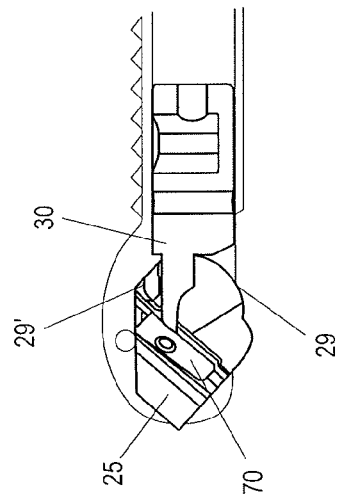

FIGS. 20A-B illustrate one embodiment of the mechanics within lower jaw 21 concerning the shuttle retainer seat 25 and retaining pin 30. As the figures suggest, in a preferred embodiment, shuttle retainer seat 25 may pivot within lower jaw 21, and retaining pin 30 may remain in contact throughout the seat's range of motion.

Retaining pin 30 may be moveable in the forward and rearward direction along its longitudinal axis, and may further be spring loaded to provide a force in at least one of the distal or proximal directions, as required.

Shuttle retainer seat 25 may, in a preferred embodiment, include a cam surface 29 on which retaining pin 30 may at least partially interact. The cam surface 29 may limit retainer pin 30 movement, or depth, into the central bore of seat 25, thereby eliminating interference of retaining pin with tissue penetrator 50. Additionally, cam surface 29 may provide spring loaded rotation of shuttle retainer seat to the position needed to interact with the tissue penetrator. For example, the retaining pin 30 may be adjusted dependent upon the distance the jaws 20, 21 are apart. The adjustment of retaining pin applies a force on the cam surface 29 of seat 25, thereby rotating the seat to the desirable position. In a preferred embodiment, the cam surface 29 may maintain a precise retaining pin protrusion distance into the seat for any seat rotation angle. This may prevent the tissue penetrator from adversely interacting with the pin, aside from any proximal deflection of the retainer pin caused by the tissue penetrator contacting the pin radius 31, as the tissue penetrator enters the seat. Further, a second portion of cam surface 29 (labeled as seat radius 29') may interact with tissue penetrator 50 as tissue penetrator 50 extends into shuttle retainer seat 25. This interaction may provide further alignment of shuttle retainer seat 25 and tissue penetrator 50 for tissue penetrator 50—shuttle 70 interaction.

Additionally, once tissue penetrator 50 exits from shuttle retainer seat 25, seat may return to its original position. This may occur once tissue penetrator terminates contact with seat radius 29', allowing seat to return to its starting position. Upon withdrawal of tissue penetrator, retainer pin 30 returns to its distal position. Retainer pin may then also interact with cam surface 29 to return the seat to its original position.

Figure 21:
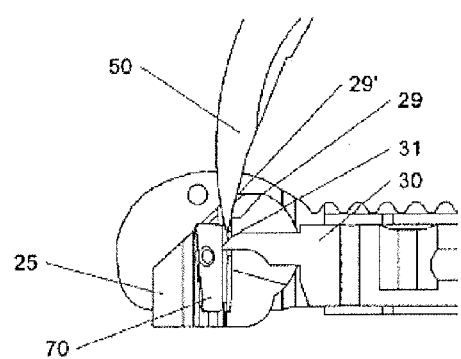
FIG. 21 illustrates, in cross-section of a lower jaw, one embodiment of the interaction of the suture shuttle, shuttle retaining seat, tissue penetrator, and retaining pin.

In a further embodiment, shown in FIG. 21, retainer pin 30 may be considered passive, wherein the spring, which pushes the pin distally, is not displaced dependent upon the other factors, such as the distance between jaws 20 and 21. As such, passive retainer pin 30 is held in a distal position in lower jaw 21, which also therefore holds shuttle retainer seat 25 in a distal position as well. In this embodiment, shuttle retainer seat 25 includes a seat radius 29', which is the radius of a portion of cam surface 29, and retainer pin includes a pin radius 31. Seat radius and pin radius may interact with tissue penetrator 50 upon extension of tissue penetrator from upper jaw 20 towards lower jaw 21. As tissue penetrator 50 comes into contact with shuttle retainer seat 25, it may contact both seat radius 29' and pin radius 31, thereby rotating seat 25 to the desired position (which is dependent upon tissue penetrator angle of entry, which is dependent upon the distance between the jaws), for tissue penetrator entry and collection of shuttle 70. Similarly, the entry of tissue penetrator, upon contact pin radius 31, pushes against pin 30 and pushes pin, against its spring force, in the proximal direction. In this embodiment, the lower jaw 21 mechanics are passive, and are adjusted to proper angles and positions by the tissue penetrator contacting the pin and seat radii to create the adjustment necessary for proper tissue penetrator-seat alignment for precise collection of shuttle 70.

Figure 22:
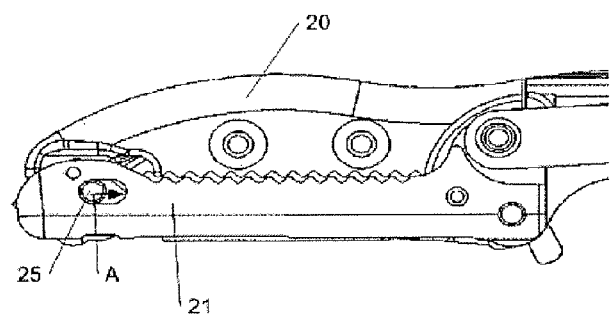
FIG. 22 illustrates a further embodiment of a shuttle retainer seat within the jaw.

In yet another embodiment, FIG. 22 illustrates a shuttle retainer seat 25 which may include a further degree-of-freedom aside from the aforementioned rotational degree-of-freedom. In one example, seat 25 may have a translational movement in the distal-proximal direction through at least a portion of the longitudinal length of lower jaw 21. Arrow A illustrates the translational motion in the proximal direction, from the initial distal position of seat 25. This added degree-of-freedom may provide further optimal alignment of seat with respect to tissue penetrator 50. Further, it may provide a more compliant landing area for tissue penetrator, accommodating any tissue penetrator targeting errors which may occur. As such, seat 25 is not constrained to its exact mounting location on lower jaw 21.

Figure 23:
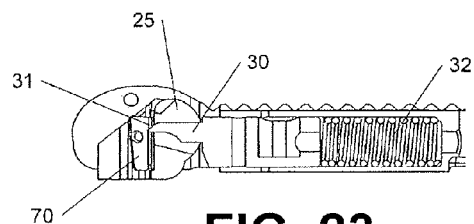
FIG. 23 illustrates, in cross-section of a lower jaw, one embodiment of a retaining pin, including a spring.

FIG. 23 illustrates a first embodiment of the initial set-up of suture passer device 10, prior to use. In this example, shuttle 70 may be initially positioned within shuttle retainer seat 25. Shuttle retainer seat may include a stop within its core to regulate the depth to which shuttle 70 may be positioned. Also, since inner core of seat 25 may be tapered, the stop would prevent jamming of the shuttle 70 within the taper.

Spring 32 of retainer pin 30 may be used to preload shuttle 70. As shuttle is inserted into seat 25, retainer pin 30 moves proximally as shuttle engages pin radius 31. Once the shuttle is in place, retainer pin 30, through a force from spring 32, returns to its distal position. In this position, retainer pin 30 may pass through a U-shaped notch 76 on shuttle 70 (see FIG. 24), thereby securing shuttle within seat 25. Upon retainer pin 30 returning to its distal position, spring 32 illustrates its function in lower jaw 21. For example, in a preferred embodiment, the spring's 32 distal force has several functions including, but not limited to: pushing retainer pin 30 distally to capture shuttle, pushing the seat distally into a receptive position for tissue penetrator insertion, providing rotational torque to rotate seat into an optimal angle for tissue penetrator insertion based on the interaction of cam surface 29 and retainer pin 30.

Figure 24:
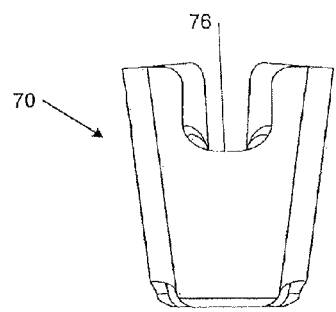
FIG. 24 illustrates another embodiment of a suture shuttle.
Figure 25:
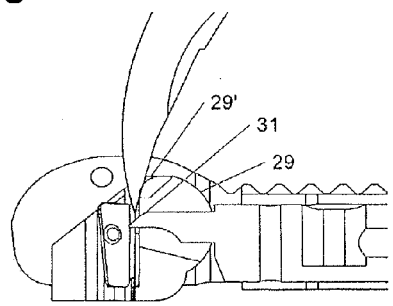
FIG. 25 is a close-up cross-section illustrating the interaction of a retaining pin, shuttle retainer seat, tissue penetrator and lower jaw.

FIGS. 24 and 25 further illustrate the interaction of shuttle 70 and retaining pin 30 in this embodiment. The U-shaped notch 76 is similar to the oval slot, or opening, 174 and 274 of other shuttle embodiments (see FIGS. 6B and 7). However, unlike the oval slot, the U-shaped notch, of a preferred embodiment, provides easier access into the area by the tissue penetrator, as well as allowing tissue penetrator to rotate seat 25 without portions of shuttle 70 interfering with process.

Similarly, in a preferred embodiment, when shuttle 70 is located on tissue penetrator 50, and tissue penetrator 50 extends from upper jaw 20 towards lower jaw 21 and seat 25, the tip of tissue penetrator acts on seat and retainer pin 30 in much the same way as when shuttle is located within seat 25. Therefore, as tissue penetrator 50 moves into the central bore of seat 25, the tip of tissue penetrator 50 engages the seat radius and pin radius 29' and 31 which may properly align seat 25 with tissue penetrator 50, as well as push retainer pin 30 proximally and away from seat 25. Once tissue penetrator 50 is extended fully into seat 25, shuttle 70 may be within seat as well, and may further be in the proper position within seat for securing itself therein. Thus, retainer pin 30 may move distally once the U-shaped notch 76 passes through the longitudinal path of retainer pin 30. As retainer pin 30 moves distally, it may pass at least partially through U-shaped notch, thereby securing shuttle 70 within seat 25. The tissue penetrator 50 may then be retracted, leaving shuttle 70 within seat 25. Tissue penetrator 50 may then extend once again into seat 25 to collect shuttle 70, in which the reverse occurs and tissue penetrator 50 pushes retainer pin 30 proximally and shuttle 70 may then be collected.

Figure 26:
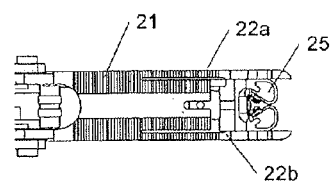
FIG. 26 is a top plan view of one embodiment of a lower jaw and shuttle retainer seat.
Figure 27:
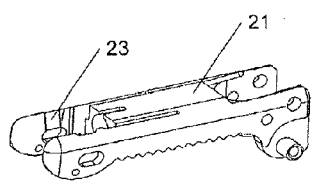
FIG. 27 is a perspective view of a further embodiment of a lower jaw.

In one embodiment, shuttle retainer seat 25 may be press-fit into lower jaw 21. In a first example, as shown in FIG. 26, lower jaw 21 may include flexible, side members 22 a and b, which flex as shuttle retainer seat 25 is inserted into place. Once in place, flexible side members 22 a and b return to their original position, securing seat in between them. As such, flexible side members may include a groove on the inner surfaces, or the like, so that the inner width in between the flexible side members is wider than on the edges. In a second example, as in FIG. 27, the side members of lower jaw 21 may include a tapered lead-in element 23 such that seat may be wedged within the taper. Other similar features may also be used to secure seat within lower jaw member 21.

Figure 28:
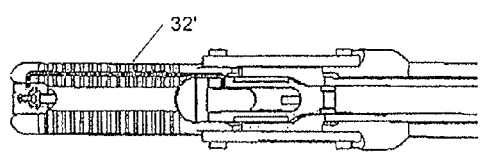
FIG. 28 illustrates a top plan view of a lower jaw wherein one embodiment of the shuttle retainer seat and stiff member is positioned.

In an alternative embodiment, in FIG. 28, shuttle retainer seat 25 may instead be controlled by a stiff member 32'. Stiff member 32 may rotate shuttle retainer seat, as the upper and lower jaws 20 and 21 move relative to one another, to maintain the proper angle with the tissue penetrator. The stiff member 32' is controlled via mechanisms in the actuator 15 of device 10 to ensure proper alignment.

FIGS. 29A-29K illustrate cross-sectional views of a preferred embodiment of the interaction of shuttle 70, shuttle retainer seat 25, retainer pin 30 and tissue penetrator 50 at lower jaw 21. Many of the operations discussed above would be used in this illustrated series of actions.

Figures 29A, 29B:
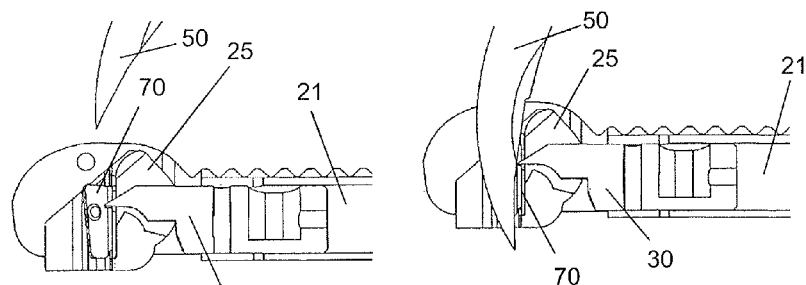
FIGS. 29A-29K illustrate an embodiment of the interaction of the shuttle, shuttle retainer seat, retainer pin and tissue penetrator as the shuttle is passed between the shuttle retainer seat, the tissue penetrator, and back again.

In FIG. 29A, shuttle 70 may be secured within shuttle retainer seat 25 by retainer pin 30 in lower jaw 21. Tissue penetrator 50 is shown to be above lower jaw 21.

In FIG. 29B, tissue penetrator 50 may pass through shuttle retainer seat 25, where shuttle 70 may be located, and may push retainer pin 30 proximally. As discussed earlier, the shuttle retainer seat 25 may be movable to accommodate the entry angle of tissue penetrator 50.

Figures 29C, 29D:
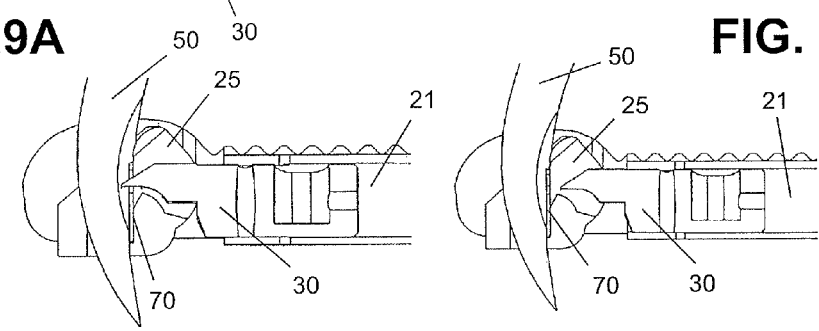

In FIG. 29C, tissue penetrator 50 may extend fully into shuttle retainer seat 25, engaging the shuttle 70. Retainer pin 30 may move distally again, back to its original position, and into groove on the back portion of the tissue penetrator (as well as through the U-shaped portion of the shuttle 70, not shown), due to the spring force pushing the retainer pin distally.

FIG. 29D illustrates the retainer pin 30 being manually retracted proximally, through use of the actuator 15 (discussed below), to disengage the retainer pin from the shuttle 70.

Figures 29E, 29F:
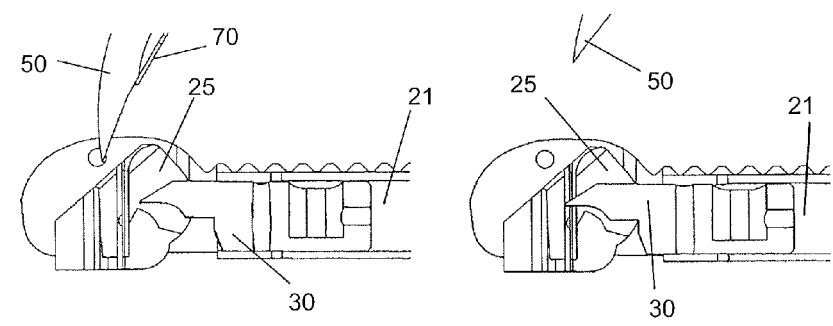

In FIG. 29E, the tissue penetrator 50, with shuttle 70 engaged, may be retracted out of the lower jaw 21 and back towards upper jaw 20. The shuttle 70 may be removed from the shuttle retainer seat 25 when the retainer pin 30 is retracted proximally, as shown. FIGS. 29A-29E illustrates one example of the tissue penetrator 50 engaging shuttle 70, located in the shuttle retainer seat 25, and retracting shuttle 70 up to upper jaw 20.

In FIG. 29F, the tissue penetrator 50, with engaged shuttle 70, may be retracted back to upper jaw 20, and actuator 15 is released such that retainer pin 30 may move back to its original, distally located, position. This may be considered to be one pass of the shuttle 70, which may have suture and/or suture clip attached.

Figure 29G:
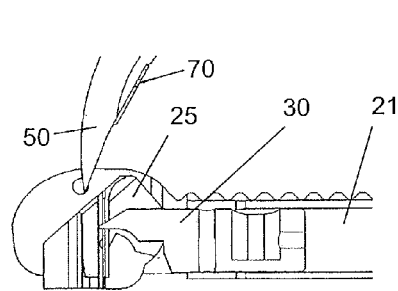

In FIGS. 29G-29K, an example of a second pass is illustrated where the shuttle is passed from the tissue penetrator 50 to the shuttle retainer seat. In FIG. 29G, the tissue penetrator is extended from upper jaw 20 towards lower jaw 21. Shuttle 70 may be engaged on tissue penetrator 50. Retainer pin 30 may be in a distal position.

Figure 29H:
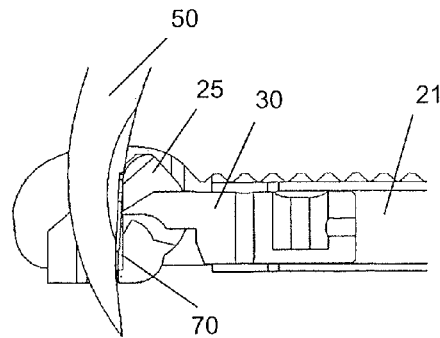

In FIG. 29H, the tissue penetrator 50 and engaged shuttle 70 enter into shuttle retainer seat 25. Retainer pin 30 may be pushed proximally by the tissue penetrator 50 and/or engaged shuttle 70.

Figure 29I:
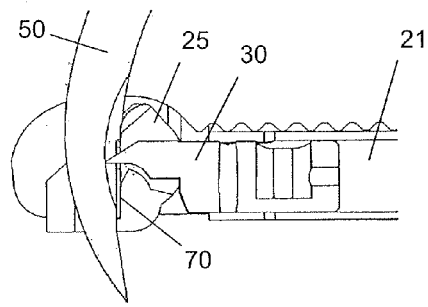

In FIG. 29I, the tissue penetrator 50 may be extended completely such that retainer pin 30 may return to a distal position, thereby passing through, for example, the U-shaped opening (not shown) on shuttle 70 and the groove within tissue penetrator 50. Shuttle 70 may now be secured within shuttle retainer seat 25, and may even still be engaged on tissue penetrator 50.

Figure 29J:
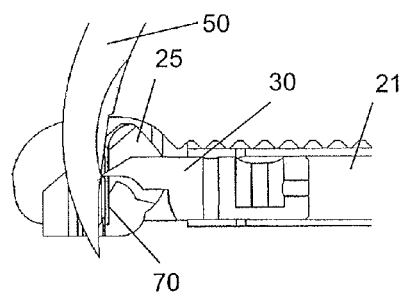

FIG. 29J illustrates tissue penetrator 50 retracting from shuttle retainer seat 25 and lower jaw 21. Retainer pin 30, though pushed proximally, once again, by the movement of tissue penetrator 50, the spring (not shown) within retainer pin 30 may still be sufficient to maintain the retainer pin 30 in a position as distal as possible such that shuttle 70 may still be retained within shuttle retainer seat 25 by retainer pin 30. The force on the shuttle 70, applied by retainer pin 30, and against the movement of tissue penetrator 50, may cause a retaining structure, such as the dimple/divot structures discussed above, to disengage such that tissue penetrator and shuttle disengage from each other. Shuttle 70 is thus retained within shuttle retainer seat 25.

Figure 29K:
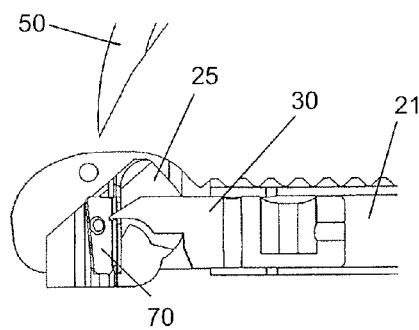

In FIG. 29K, the tissue penetrator 50 may retract completely away from shuttle retainer seat 25, and retainer pin 30 may then move distally to return to its original position. Shuttle 70 is therefore secured within shuttle retainer seat 25 by retaining pin 30. Tissue penetrator 50 may retract completely back to upper jaw 20.

Thus FIGS. 29A-29K illustrate one embodiment of the interaction of the tissue penetrator 50, shuttle 70, shuttle retainer seat 25 and retainer pin 30. This interaction may include the various mechanisms, structures and operations discussed throughout.

The jaws 20 and 21 can be moved totally independently of the tissue penetrator 50. The jaws may be used to grasp and manipulate tissue prior to suture passage. As described below, since the tissue penetrator and jaws operate independently of one another, the jaws may be used as graspers without having to expose the tissue penetrator.

Figure 30A:
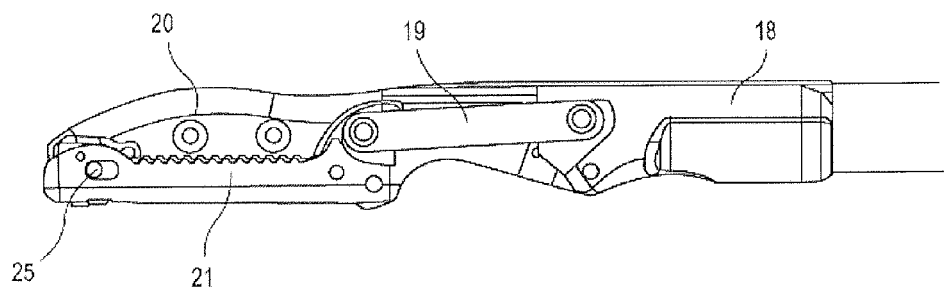
FIGS. 30A-30B illustrate one embodiment of a distal portion of a suture passer device including first and second jaws.
Figure 30B:
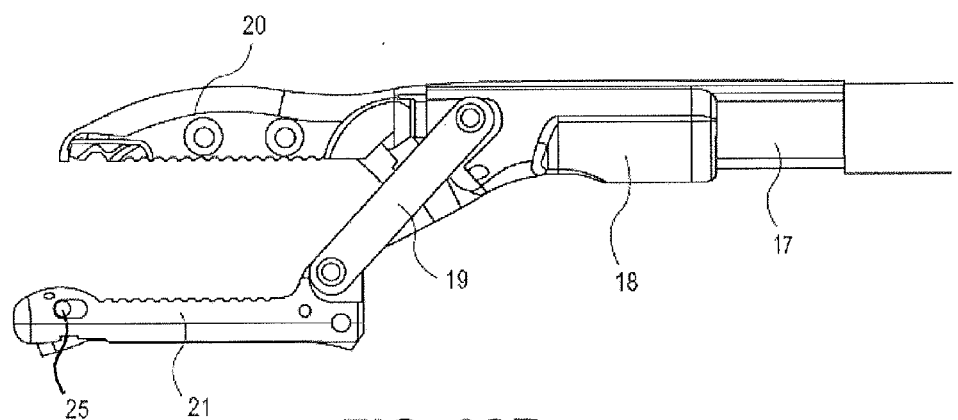

In one embodiment, the upper and lower jaws 20 and 21 may move kinematically in that they may remain substantially parallel to one another when the lower jaw is brought away from the upper jaw. For example, in FIGS. 30A-B, illustrating a preferred embodiment, lower jaw is pivotally attached to pivot arm 19. Pivot arm 19 is then attached to sliding element 18 which may slide along the outer surface of shaft 17. In this example, when lower jaw is moved away from upper jaw, sliding element 18 moves distally along shaft 17 such that lower jaw may remain parallel to upper jaw. This sliding movement compensates for the tracking error of the pivot arm, also known as a 4-bar linkage, such that the lower jaw may track the arc traversed by the tissue penetrator 50. Additionally, this movement of the sliding element 18 allows the lower jaw 21 to remain substantially directly opposite the upper jaw 20 throughout the range of motion of the lower jaw. As a further example, if the lower jaw were not attached to the sliding element, the lower jaw, as it moves away from the upper jaw, would also move proximally, relative to the upper jaw, and thus be out of alignment with upper jaw.

Aside from the sliding pivot arm example above, other mechanisms such as, for example, gear drives, linkages, cable drives, and the like, may be used to ensure proper alignment of top and bottom jaws 20 and 21 during jaw actuation.

The upper jaw 20 may be fixed in place as to shaft 17. The fixed upper jaw may provide many advantages to a moveable upper jaw, such as providing a reference point for the surgeon, allowing for independent adjustability of the jaws and tissue penetrator engagement position, and the like.

The parallel relationship of the upper and lower jaws 20 and 21 of this embodiment allow for easier manipulation of tissue, while also preventing the jaws from overly impinging any portion of the tissue. For example, if the jaws opened as a typical V-shaped pattern, then the proximal tissue, deeper into the V shape, would have excess force on it than the distal portion of the tissue, within the jaws. The parallel relationship ensures that the force of the jaws is spread equally throughout the tissue in between the jaws.

In an alternative embodiment, the upper jaw 20 may slide distally and proximally, while the attachment point of pivot arm 17 remains stationary. Thus, as the lower jaw moves away from the upper jaw, the upper jaw moves proximally to maintain alignment with the lower jaw. FIGS. 31 and 32A-C illustrate this embodiment.

Figure 31:
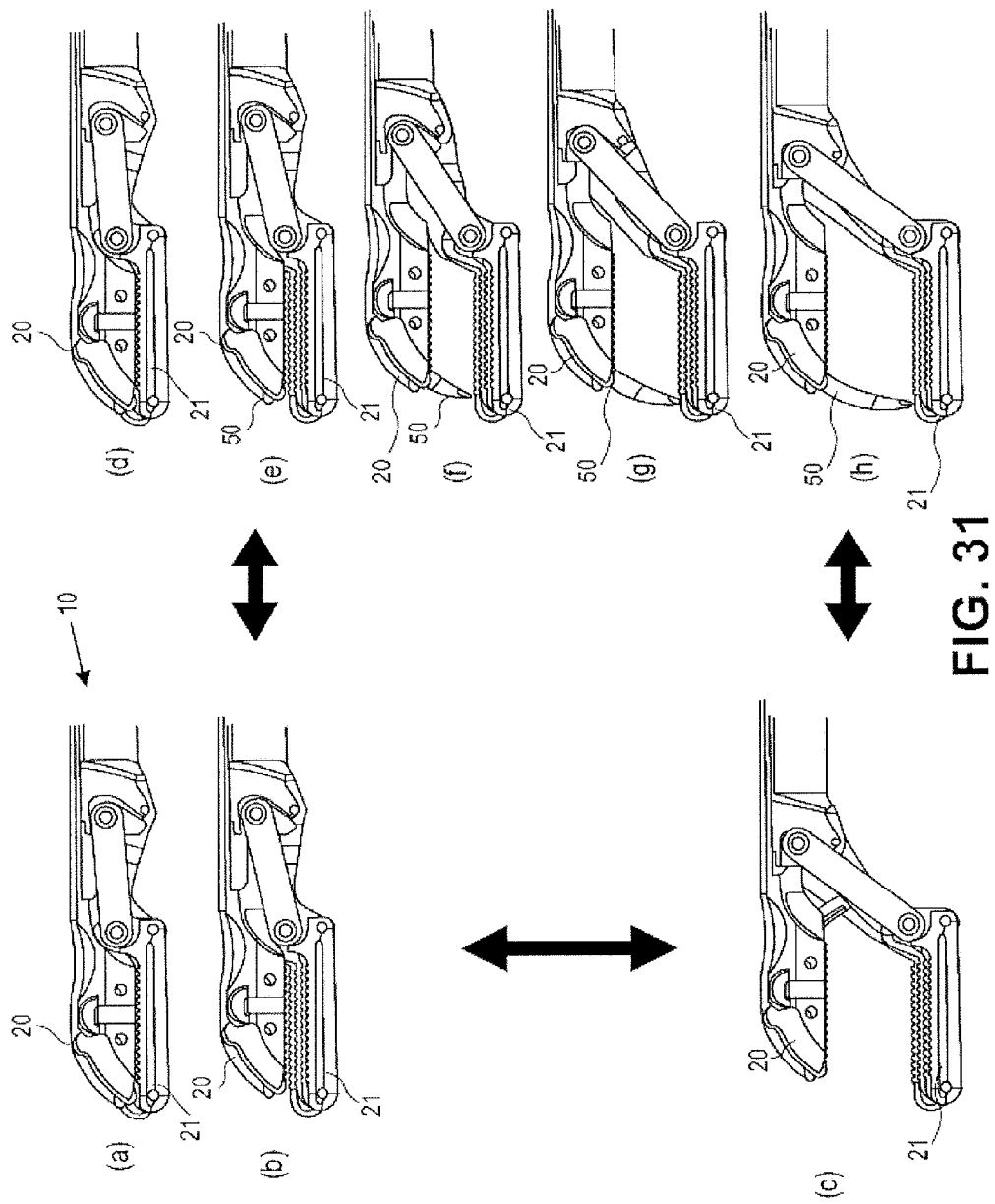
FIGS. 31(*a*) to 31(*h*) illustrates another embodiment of a distal portion of a suture passer device.

Also illustrated in FIG. 31 are the various entry angles of the tissue penetrator when the upper and lower jaws are at various distances from one another. For example, the tissue penetrator will meet the shuttle retainer seat, located in the lower jaw, no matter the separation between the upper and lower jaws. Thus, the jaws may be clamped to tissue of any depth, and the tissue penetrator will pass through the tissue and hit the lower jaw directly at the shuttle retainer seat.

Figure 32A:
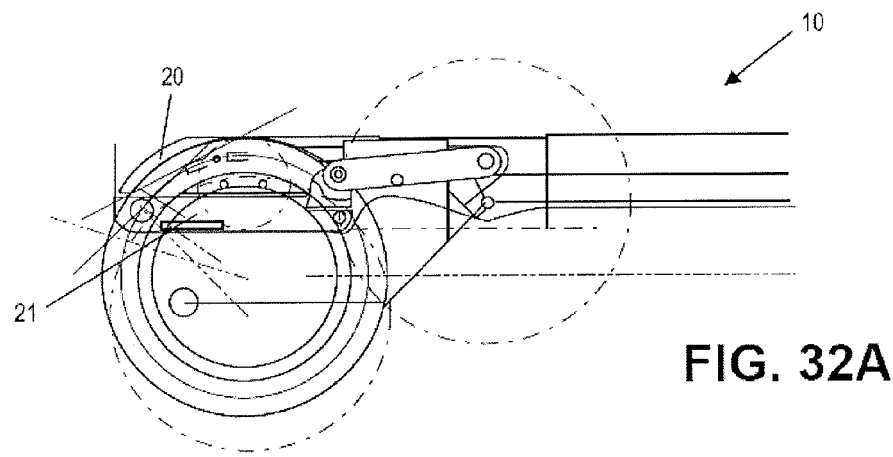
FIGS. 32A-32C show yet another embodiment of a distal portion of a suture passer device.
Figure 32B:
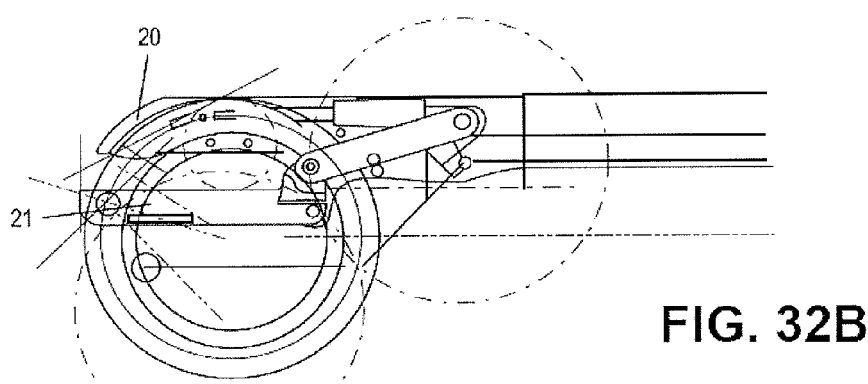
Figure 32C:
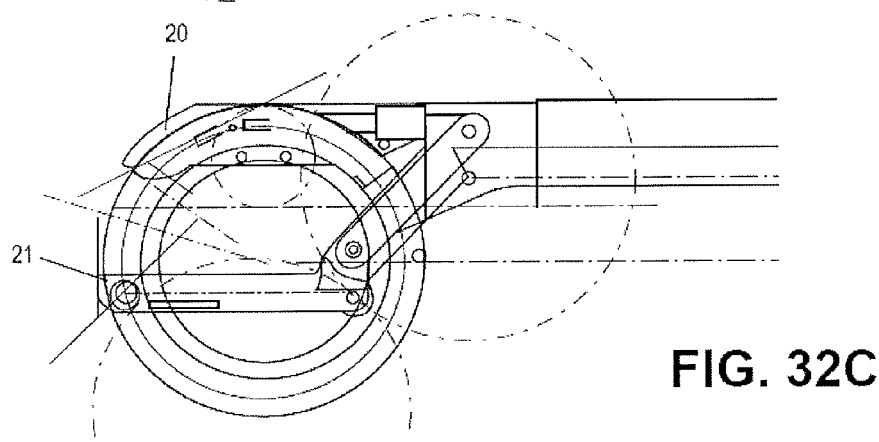

For example, in FIG. 31, upper and lower jaws 20 and 21 may have an initial position (a). The expansion of the jaws, illustrated by positions (a)-(c), may occur by the lower jaw 21 pivoting away from upper 20, while upper jaw 20 slides proximally to maintain a functional relationship between the jaws as the lower jaw 21 pivots. FIG. 31 also illustrates the extension of tissue penetrator 50 from the upper jaw 20 to the lower 21, in positions (a) and (b) to (d) and (e). Positions (d)-(h) of FIG. 31 illustrate a further method wherein the simultaneous expansion of jaws 20 and 21 and extension of tissue penetrator 50 may occur. Additionally, FIG. 31 illustrates in positions (c) to (h), the extension of the tissue penetrator 50 when jaws 20 and 21 are expanded. As such, FIG. 31 illustrates one embodiment of the device 10 in which the lower jaw 21 may track the arcuate path of tissue penetrator 50, such that tissue penetrator 50 may engage the lower jaw 21 at the substantially same position regardless of the position of the lower jaw 21. FIGS. 32A-C further illustrate the arcuate path the lower jaw 21 may travel.

The size of the suture passer device 10 may be any size useful in performing surgery on the body. For example, for many arthroscopic joint surgeries, the upper and lower jaws may be around 16 mm in length, though a length of up to about 25 mm is obtainable. This may be significantly scaled down for a device for use in, for example, wrist surgery. Alternatively, a larger device, with larger jaws, may be useful for hip or torso surgery.

In further examples, the suture passer device may, for example, be able to pass suture through any tissue up to about 10 mm, though a scaled up version of the device may allow for greater amounts of tissue. Moreover, in most embodiments, the device may pass through a standard 8 mm cannula.

Actuator Mechanism Examples

The suture passer devices 10 described above may include, for example, three types of controlled motion: (1) the open/close movement of the jaws, whereby at least one jaw moves relative to the other; (2) the extension/retraction of the tissue penetrator; and, optionally, (3) the retention/release of the shuttle retaining pin 30 from the seat 25 on the second jaw. Although there are numerous ways in which these motions may be accomplished, including those described in the Ser.

No. 11/773,338 application, and various provisional applications already incorporated by reference herein, described below are mechanical assemblies (also referred to as "layers") that may be used to precisely control these three types of motions of the suture passer. These layers are referred to as the jaw motion control layer or the conjugate motion control layer (controlling the relative motion of the jaws), the tissue penetrator control layer (controlling the motion of the tissue penetrator), and the retaining pin control layer (controlling the motion of the shuttle retainer seat and/or retaining pin).

Although these layers are described here in the context of a suture passer, it should be clear that the techniques and principles described herein may be applicable to other devices, particularly those having movable jaws and/or other movable features. For example, the conjugate motion control layer may be used to control a forceps, clamp, or other device. Thus, the invention should not be limited to the figures described herein, or the specific embodiments.

1. Jaw Motion Control Layer

The jaws 20 and 21 move to open and close in parallel. This means that the inner surfaces of the jaws (e.g., the downward-facing surface of the upper jaw and the upward-facing surface of the lower jaw) open and close so that they are substantially parallel. The jaws also move so that the tissue penetrator 50 extending from the first jaw contacts roughly the same position on the second jaw, for example, the shuttle retainer seat 25, when the tissue penetrator is extended, regardless of how open or how closed the jaws are relative to each other.

It should also be pointed out that the conjugate motion of the jaws may also be semi-parallel. For example, in one variation, the device may have a non-parallel 4-bar linkage by changing the length of the links, resulting in a semi-parallel motion. This may be beneficial for some surgical procedures.

In a first embodiment, illustrated in FIG. 33, the lower jaw control mechanism may control both the tower jaw 21 opening and closing, as well as the movement of sliding element 18. While two separate mechanisms may perform the same function overall, the present invention is capable of using a single lower jaw control mechanism to perform both movements with a single mechanism. The coordination of these two motions allow lower jaw 21 to accurately track the arcuate path of the tissue penetrator 50 extending from upper jaw 20, which in this example, is stationary.

In this example, the actuator 15 encloses a jaw trigger 304 which may serve as the manual interface for the user. The trigger 304 may be pushed or pulled, along arc B, depending on the desire of the surgeon to open or close the lower jaw 21. The mechanism may include two linear bushings 302, which drive the respective control rods and links 301 to activate the sliding element 18 and the tower jaw 21 and pivot aim 19. Each bushing is responsible for the movement of one of the lower jaw 21 and pivot arm 19 or the sliding element 18. The pivot point 303 of the trigger 304 is at different distances from the two linear bushings 302. Thus, the bushings drive the control rods and links 301 at relatively different rates and distances. Thus, the actual traveling distances of the lower jaw 21 and sliding element 18 may be different. These distances may be determined and set so that the lower jaw 21 travel approximates the same arcuate path as tissue penetrator 50.

This mechanism may be rigid in order to minimize errors as to clamping pressure and location during use.

The jaws 20 and 21 may also be locked in any position by a lock, such as a valve, latch, pin or the like. This is important because it allows leverage for penetrating the tissue, such that one may bear down on the trigger for the tissue penetrator without worrying about damaging the tissue.

In a preferred embodiment, illustrated in FIGS. 34A-C, a locking mechanism may be a ratchet mechanism 309. Ratchet 309 may be positioned on trigger 304, and may further have an interface portion 306 placed on finger spaces of trigger 304, which allows for convenient use by a user. A pawl 305 includes the ratchet 309, interface portion 306 and a pivot 307. A spring 308 may be included to provide a set position of pawl 305. In the illustrated example, the spring 308 provides a set position of the ratchet being engaged, however, any configuration may be used.

In operation, this exemplary lock may allow the user to lock the jaws 20 and 21 at a set distance from one another. The user may pull trigger 304 backward, using a first finger at location 304a, until the jaws are at the desired clamped position around tissue. While the trigger is pulled, the ratchet, in the engaged set position, allows the trigger to move backward, but will not allow the trigger to move forward. Spring 308 maintains a force on pawl 305 to ensure ratchet remains engaged. Thus, the trigger moves from a first position, FIG. 34A, to a second position, FIG. 34B, and is secured by ratchet 309.

The user may then proceed to do other procedures, such as extending the tissue penetrator or the like. This mechanism may assist the user in maintaining jaw position during tissue penetrator deployment, as well as maintaining constant pressure on the tissue to increase tissue penetrator targeting accuracy. Of course, engaging the ratchet and locking the jaws in place may solely be used as a grasper, without deploying the tissue penetrator. Once the user has completed the task, and is ready to disengage the jaws 20 and 21, the user may press the trigger at the second position 304b, using a second finger, thereby also pressing on interface portion 306 which may disengage the ratchet 309. The interface portion 306 is pressed hard enough to disengage the ratchet, but light enough to allow the trigger 304 to move forward and open the jaws, as illustrated in FIG. 34C.

In a preferred embodiment, the pawl 305 is attached to trigger 304 at pivot 307, and the ratchet portion 309 may be secured to the actuator shell (15, generally) such that is in a fixed position.

2. Tissue Penetrator Control Layer

Figure 35A:
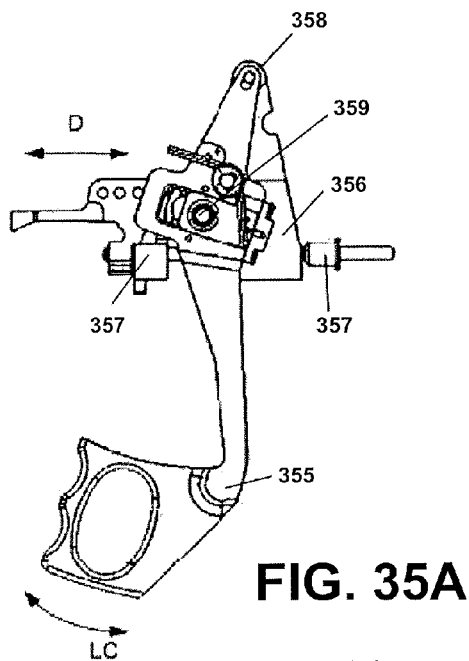
FIGS. 35A-35B illustrate a first embodiment of a tissue penetrator control mechanism.
Figure 35B:
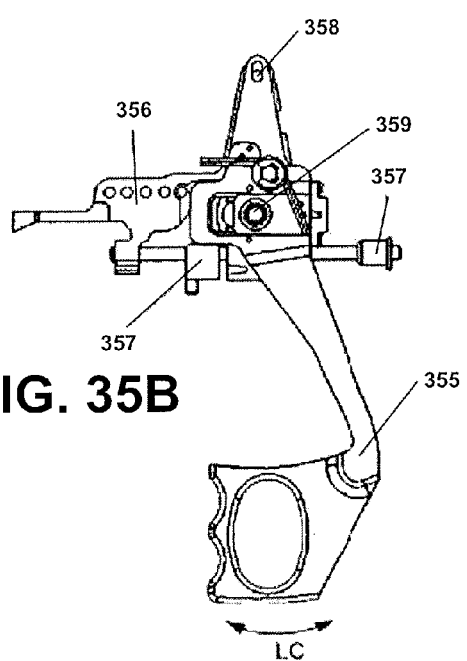

As illustrated in FIGS. 35A-B, one embodiment of the components that make up the tissue penetrator control layer may include at least the tissue penetrator 50, coaxial tissue penetrator push/pull rod (not shown, but connects drive block 356 with tissue penetrator 50), and the subassembly linking the push/pull rod to the tissue penetrator control trigger 355. The tissue penetrator control trigger 355 may act directly on the tissue penetrator.

In a preferred embodiment, the trigger 355 is a push/pull system, meaning the trigger can be either pushed or pulled, along path LC, to direct the tissue penetrator in or out of upper jaw 20. The trigger 355 may be spring loaded, such that, for example, the trigger is biased such that the tissue penetrator 50 is retracted, within the upper jaw 20.

The trigger 355 may further include a first pivot 359, wherein the rotational motion of the trigger 355 is turned into linear motion of the drive block 356, along path D, through the connection at a pin and slot interface 358. The drive block is limited to linear motion by the use of at least one linear bearing 357. The linear motion of drive block 356 applies a force directly on the tissue penetrator 50 to push and pull the tissue penetrator as desired by the manual motions of the surgeon.

Figure 38A:
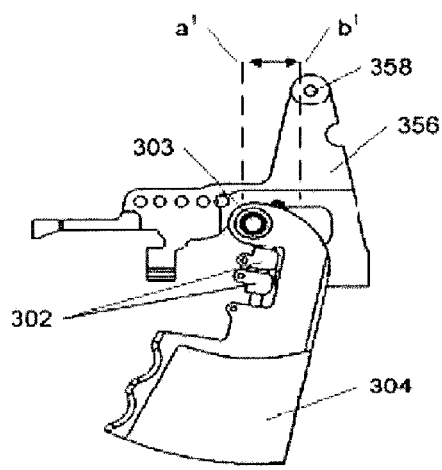
FIGS. 38A-38C illustrate the interaction between one embodiment of the tissue penetrator control layer and one embodiment of the jaw control layer.
Figure 38B:
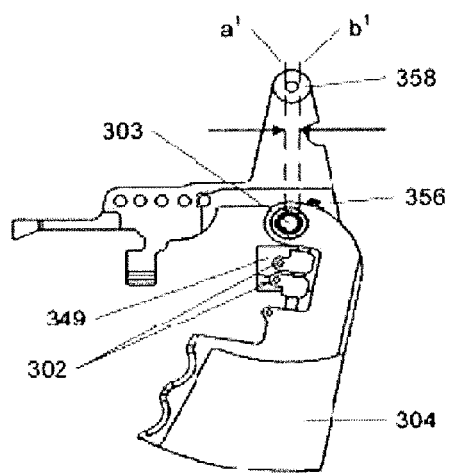
Figure 38C:
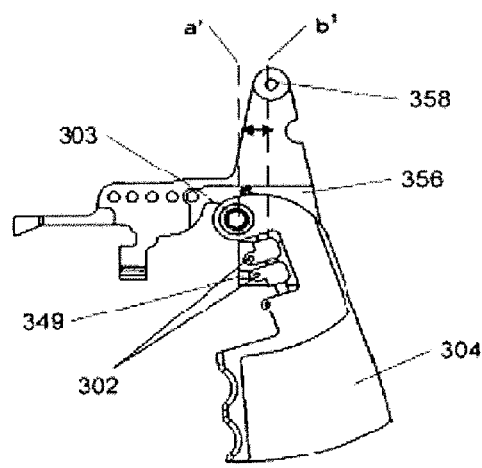

As illustrated in FIGS. 38A-C, the tissue penetrator control may further include limit stop capabilities to prevent tissue penetrator from advancing too far into shuttle retainer seat 25.

Further, the limit stop 349 is correlated to the amount the jaws 20 and 21 are open, such that for example, the limit stop 349 allows a wide range of motion when the jaws are spread far apart, and a narrower range of motion when the jaws are closer together.

The limit stop 349 may be directly correlated such that the stop occurs precisely when the tissue penetrator 50 is in the correct location within the seat 25. Furthermore, this limit stop 349 may be related to limit stop 335 in retainer pin 30 actuator (FIG. 37A), such that retainer pin 30 only actuates when tissue penetrator is within seat 25 in a location wherein it may collect shuttle 70.

Limit stop 349 may be located on drive block 356, but interacts with the jaw control layer, discussed above, such that it may provide a proper limit stop customized to the position of lower jaw 21 in relation to upper jaw 20.

Limit stop 349 operates to limit the motion of drive block 356 to a certain distance required. This certain distance is determined by the distance the jaws are spread apart. For example, in FIGS. 38A-B, the trigger 304 is positioned such that the jaws are fully open. Thus, the tissue penetrator, if activated at the point as shown in FIG. 38A, the tissue penetrator would have to travel a long distance, to the position shown in FIG. 38B, to span the gap between the upper and lower jaws. Thus, as can be seen by the change in distance between the two reference lines a' and b', from FIG. 38A to FIG. 38B, the drive block 356 travels a large distance, denoting a large distance the tissue penetrator has moved. Conversely, in FIG. 38C, the trigger is positioned such that the jaws are in a closed position. Comparing the reference lines a' and b' in FIGS. 38A and 38C illustrate that the drive block would travel a much shorter distance in FIG. 38C, than in FIG. 38A to FIG. 38B. The distance the drive block can travel is in direct relation to the change in position of trigger 304 altering the distance between it and the stop limit 349.

3. Retaining Pin Actuator Control Layer

Figure 36A:
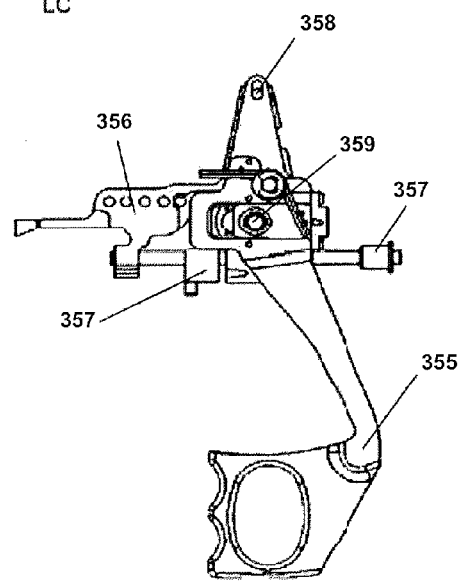
FIGS. 36A-36B illustrate further features of the first embodiment tissue penetrator control mechanism of FIGS. 34A-34B.
Figure 36B:
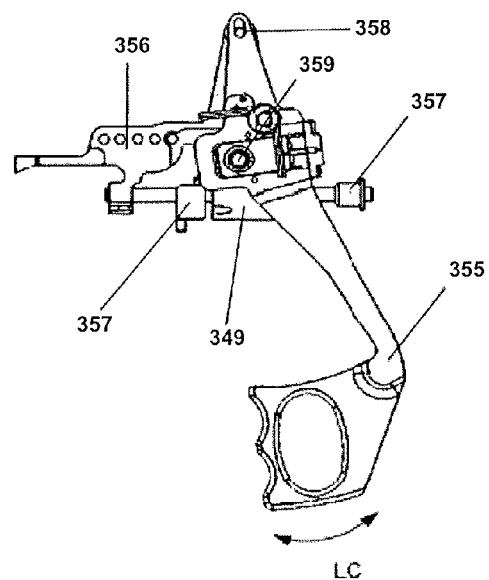

In one embodiment, the retaining pin actuator control may be located within and incorporated into the tissue penetrator control layer, previously discussed. Such a relationship between the tissue penetrator and actuator pin may be beneficial in achieving accurate communication between both elements in the jaws 20 and 21. FIGS. 36A-B illustrate two pivot points 358 and 359 within the tissue penetrator control layer, which may work consecutively. Pivot point 358 is the aforementioned pin and slot interface which may interface the trigger 355 with the retainer control layer. Pivot point 359 may control tissue penetrator 50.

In operation of this first embodiment, the trigger 355 is pulled, for example, and may pivot around first pivot 359 to extend tissue penetrator 50. Once tissue penetrator is fully extended, the trigger reaches a stop, at the position illustrated in FIGS. 35B and 36A. If the user continues pulling on the trigger, the trigger may then pivot around the pin and slot interface 358, which may pull the retaining pin 30 proximally, and away from shuttle retainer seat 25 and shuttle 70.

As discussed above, in a preferred embodiment, the retainer pin 30 may be passive, meaning that the tissue penetrator 50 may be inserted into the lower jaw 21 without having to first retract the retainer pin 30. This is possible because of the pin radius 31 and spring 32.

Figure 37A:
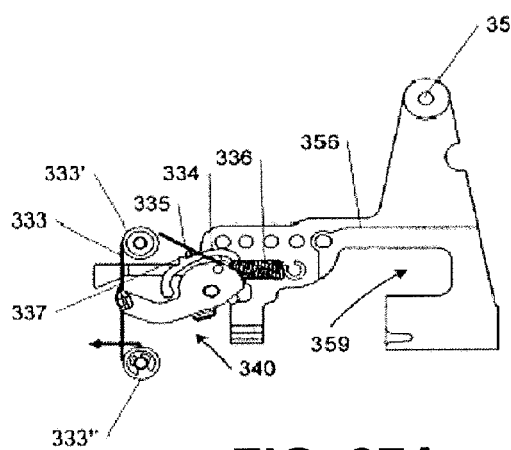
FIGS. 37A-37C illustrate one embodiment of retainer pin control layer.
Figure 37B:
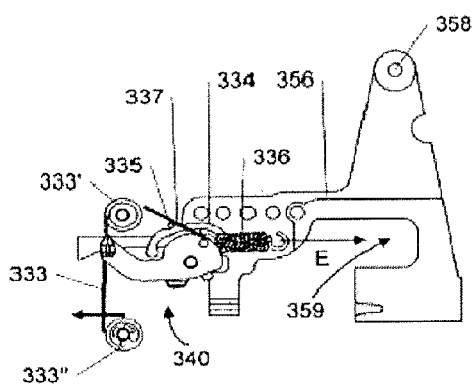
Figure 37C:
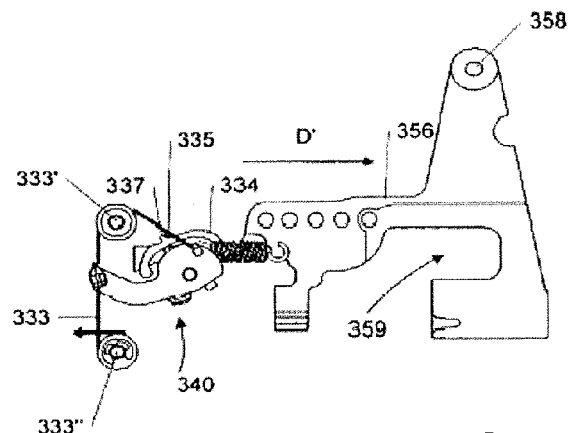

Retainer pin control layer may further include, in a preferred embodiment, a capstan 340, FIGS. 37A-C, which interfaces the retainer pin 30 with trigger 355. Capstan 340 may include a connection with retaining pin 30, such as a wire 333, a spring 336, and a reset interface 334 and stop pin 335. The capstan may be pulled proximally by trigger 355, in the direction shown as line E in FIG. 37B. Capstan moves proximally, as reset interface 334 moves past stop pin 335. A projection 337 on reset interface 334 may move from one side to the other of stop pin. At this point, capstan may be secured in place, thereby securing the retainer pin 30 in place at a position proximal to its normal, passive position adjacent shuttle retainer seat 25. Stop pin 335 may be released when driver block 356 returns to its rest location. Once trigger 355 is released, driver block 356 may return to its starting position, which may release capstan 340 by interfacing with the reset interface 334, to disengage stop pin 335, which then may return retainer pin 30 to its starting position.

Wire 333, as illustrated in FIGS. 37A-C, may connect capstan 340 with retaining pin 30. Wire 333 may run through two pulleys, 333' and 333". At least one of the pulleys, as shown in FIGS. 39A-B, shown as pulley 333, may be positioned within actuator 15 in a stationary position such that does not move relative to the device 10. Pulley 333", however, may be positioned such that it moves with the jaw actuation mechanism layer. For example, in FIG. 39A, the jaws 20 and 21 are open relative to one another, and in FIG. 39B the jaws are closed. When the lower jaw moves to a closed position, it comes in line with shaft 17, in effect, shortening the distance between retainer pin 30, in the lower jaw 21, and pulley 333". As a result, the wire 333 would be too tong. However, if pulley 333" moves backward, as shown in FIG. 39B, it will maintain the same distance between retainer pin 30 and pulley 333", thereby preventing the wire 333 from losing tension as lower jaw 21 closes.

The retainer actuator control layer may further include a bi-modal stroke limiter, or the like. This limiter ensures that the retaining pin 30 is only actuated when shuttle 70 is properly positioned within shuffle retainer seat 25. FIGS. 40-43 illustrate various configurations of the bi-modal stroke limiter.

Figure 43A:
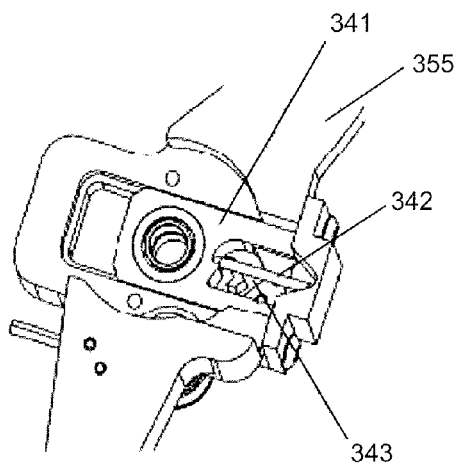
FIGS. 43A-43D illustrate further detail of one embodiment of the slide block of FIGS. 40A-42B.
Figure 43B:
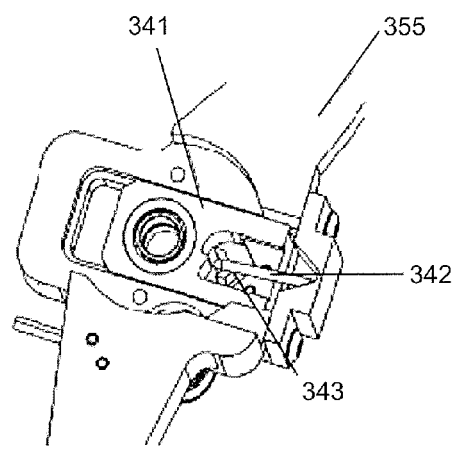
Figure 43C:
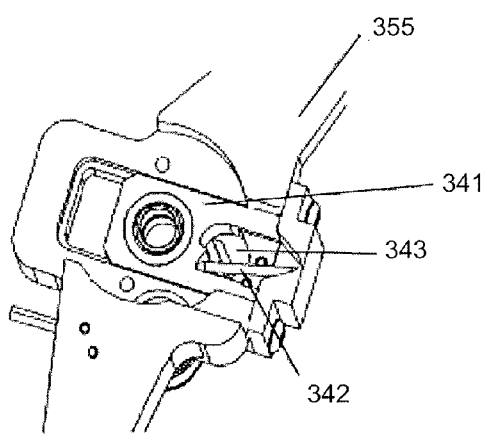
Figure 43D:
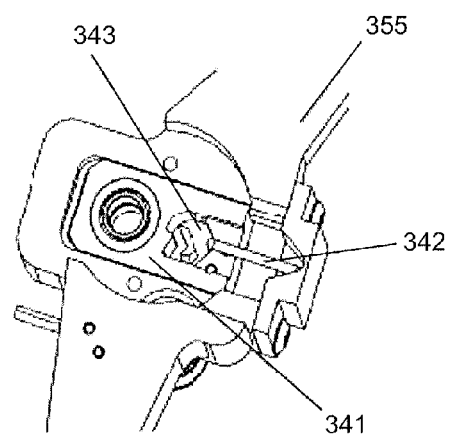

For example, in a typical tissue penetrator operation cycle, the tissue penetrator trigger 355 may pull capstan 340 in the proximal direction, thus pulling retainer pin 30 using wire 333. Spring 336, extending from capstan 340, links with trigger 355. Trigger 355 may include slide block 341, which houses, on its underside, a wire-form pin 342. The operation cycle has, for example, four cycles in which wire-form pin has four positions: 1) stable resting position, 2) short travel position, 3) stable resting position, and 4) long travel position. Position (1) is illustrated in FIGS. 40A-B and 43A. The spring 336 is lax, and trigger 355 is not engaged. Wire-form pin 342 is also at a resting position, against the body of slide block 341. Position (3) is identical to Position (1), except the actual position of wire-form pin 342 may be different, as in FIG. 43C, but still designates a rest position. Position (2), illustrated in FIGS. 41A-B and 43B, is for a short travel, in which only the tissue penetrator 50 is activated. The capstan remains in position, and retainer pin 30 remains in position adjacent shuttle retainer seat. In Position (4), as in FIGS. 42A-B and 43D, long travel takes place in which spring 336, capstan, wire 333 and retainer pin are activated, thereby moving retainer pin proximally.

The wire-form pin 342 is located within a labyrinth 343 on the underside of side block 341. The various cycles are denoted by the various positions of the wire-form pin within the labyrinth.

Undesirable movement within the linkage between the capstan 340 and trigger 355 may be absorbed by spring 336. Once spring is extended, over-travel of mechanism may be handled by the stiff extension property of the spring 336. Spring 336, therefore, operates to absorb shocks and unwanted movements within the mechanism, which may ensure smooth and predictable operation.

In some other embodiments of the device, at least a portion of the device, for example, a control system, may be electronic. For example, hardware, firmware, and/or software may be used to control the motion of the jaws, shuttle retainer/seat, shuttle, and/or tissue penetrator.

For example, a RISC chip, e.g., a PIC (Microchip Corp.) processor may coordinate and control the upper jaw position relative to the lower jaw (conjugate motion), in the embodiment where the upper jaw is movable, by using a potentiometer or similar position encoder on the trigger. A linear or rotational electromagnetic actuator may be used to position the upper jaw. Further, it could also control an electromagnetic brake, if needed, to lock the position of the upper jaw.

Additionally or alternatively, a processor could also handle all of the retainer actuator functions. It could receive input or calculate whether the shuttle is going up or down, and it could control the retainer cable tension by way of another electromagnetic actuator, such as a simple solenoid or length of shape memory alloy actuator wire.

Such devices could trade many machined and molded parts, as previously described, for off the shelf actuators commonly used in high volume consumer devices. This could drastically reduce total cost of goods and allow more precise timing of retainer actuator events.

In a further example, the tissue penetrator and/or shuttle retainer seat relative position could also be monitored with a sensor and thus close the loop, electronically ensuring that the tissue penetrator always finds its target even under severe usage conditions. This kind of closed loop control may be regulated with a microprocessor.

Electronics, or firmware, is very reliable and immune to tolerances. As the device is scaled, for example, shrunk for laparoscopic applications, there may be additional ways to offset the added expense and adapt to the even more severe precision requirements. An embedded/electromagnetic solution is one possibility.

In some embodiments, the suture passer device 110 may pass a suture back and forth through a tissue or tissues without the use of a suture shuttle.

Figures 44A, 44B, 44C:
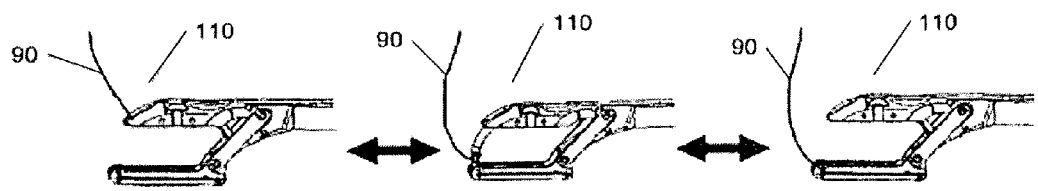
FIGS. 44A-44C illustrates one embodiment of a shuttleless suture passer device.

In general, the shuttleless suture passers may have two jaws that may open and close in parallel and pass a suture between them. A tissue-penetrating member may releasably grasp a suture and hand it off to a suture retainer that can also releasably grasp the suture. FIGS. 44A-44C illustrate one embodiment of a shuttleless suture passer that includes an upper jaw with a suture grasper and a lower jaw with another suture grasper.

In FIG. 44A, the suture 90 is initially held in the upper jaw of the suture passer. The lower jaw and the upper jaw may be opened and closed in parallel to any degree, so that tissue can be secured between them. The tissue penetrator can be extended from within the upper jaw, through any tissue between the jaws, and into the engagement region on the lower jaw. Once in the engagement region, the upper suture grasper (not visible) releases the suture into the lower suture grasper in the lower jaw. After retracting the tissue penetrator, at least part way, out of the engagement region, the device may be repositioned so that the suture can be passed from the lower jaw to the upper jaw. The tissue penetrator including a suture grasper may be extended into the engagement region again, and the suture grasper in the lower jaw can be toggled by, for example, engaging the tissue penetrator, to release the suture into the suture grasper on the tissue penetrator. Retracting the tissue penetrator pulls the suture back through the tissue towards the upper jaw.

As mentioned, any appropriate suture grasper may be used. For example, mechanical suture graspers may releasably secure the suture between two or more surfaces by squeezing the surfaces together. In general, the suture graspers such as the surfaces or jaws may be controlled automatically or manually.

Figures 45A, 45B:
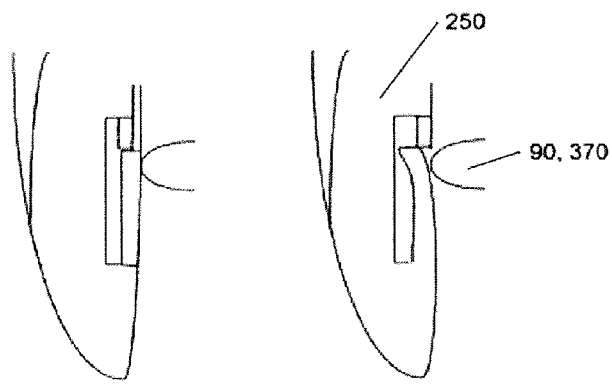
FIGS. 45 A and 45B illustrates a further embodiment of a tissue penetrator and at least one of a shuttle and a suture.

In another embodiment of tissue penetrator, the tissue penetrator 250 may include a carabiner element which may secure the shuttle to the tissue penetrator. For example, the carabiner element pivots on one end and provides an opening on the opposite end, as illustrated in FIGS. 45A-45B. The shuttle 370, or alternatively, the suture 90, may interact with the flexible carabiner element to latch onto the tissue penetrator. Alternatively, one end of the carabiner element may pivot on an hinge, and thus the carabiner element may be rigid.

Figure 46:
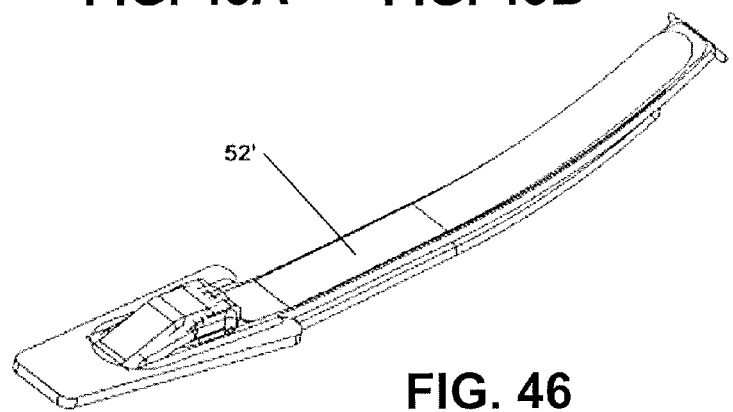
FIG. 46 illustrates a further embodiment of a shuttle retaining device on a tissue penetrator.
Figure 47:
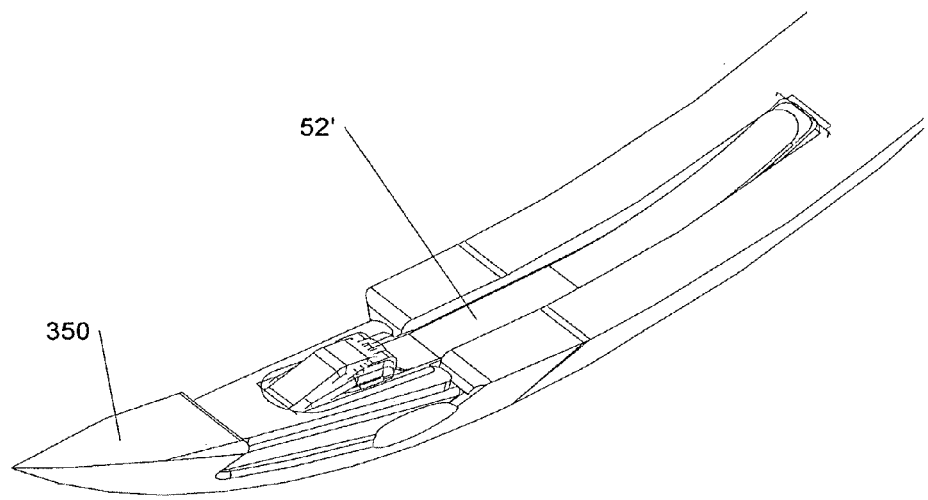
FIG. 47 illustrates one position in which the shuttle retaining device of FIG. 46 may be placed on the tissue penetrator.
Figure 48:
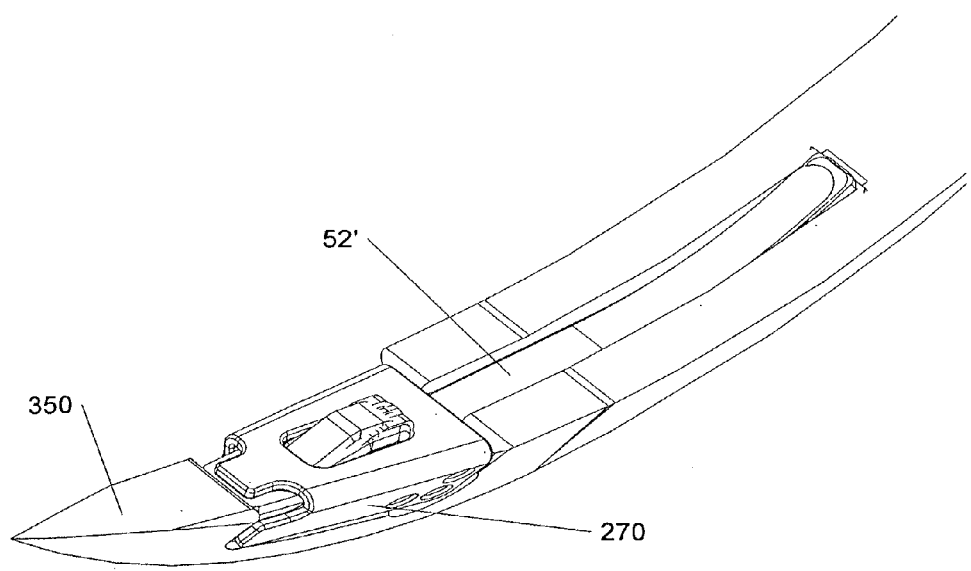
FIG. 48 illustrates the interaction of the suture shuttle, tissue penetrator and shuttle retaining device of FIG. 45.

In some embodiments, there may be additional shuttle retention devices. For example, in FIGS. 46-48, a shuttle retention device may include a passive spring latch 52' that is integral to the tissue penetrator. For example, the passive spring latch may be a small wire-formed or etched spring steel part attached to the tissue penetrator 350 on the backside in the groove for retaining pin clearance. Attachment may be, for example, through welding, gluing, screwing, clipping, or the like. Further, spring latch 52 may be part of tissue penetrator 350, wherein no attachment is necessary since spring latch 52' is integral to tissue penetrator 350. The shuttle retention may be assured with this snap latch feature. This may allow relaxing tolerances on the shuttle and reduce engage/disengagement forces overall. The same retainer pin that is alternately disposed in the shuttle's slot feature 274 to retain it in the lower jaw may still be used. Now, in this example, it may push the new latch beam spring part in distally, thereby releasing the shuttle from the tissue penetrator. As the tissue penetrator is retracted, the retainer pin 30 works as usual to retain the shuttle as it is pulled off the tissue penetrator.

One variation of this embodiment may be a leaf-spring member 52' with a tab/hook on the end which may be laser-welded to the tissue penetrator, and may form a clip that retains the shuttle. The retainer pin 30 would press the tab to release the shuttle at the appropriate time.

Surgical Methods

All of the exemplary methods described herein are best performed with continuous suture passers having jaws that open and close while remaining in an approximately parallel orientation (e.g., relative to the upper and lower tissue-contacting surfaces of the jaws) in addition, the suture passer jaws may lock so that tissue can be secured between them, and the suture passed by means of a tissue penetrator that carries the suture, which may be attached to suture shuttle, between the two jaws. In particular, these methods may be performed using a device that is configured to pass the suture between the jaws regardless of the position of the jaws relative to each other, and thus the jaws are not required to be in a particular position in order to pass the suture therebetween. The following methods are examples only, the present invention is not limited to these explicitly recited examples but may be used in other similar surgical methods.

The present invention is capable of tying numerous types of suture knots known in the art including, but not limited to Modified Mason-Allen stitch, Figure-8 stitch, Margin Convergence Stitch, Incline Mattress Stitch, and Medial Row Modified Mason-Allen Stitch.

1. Medial or Lateral Meniscus Repair

Figure 49:
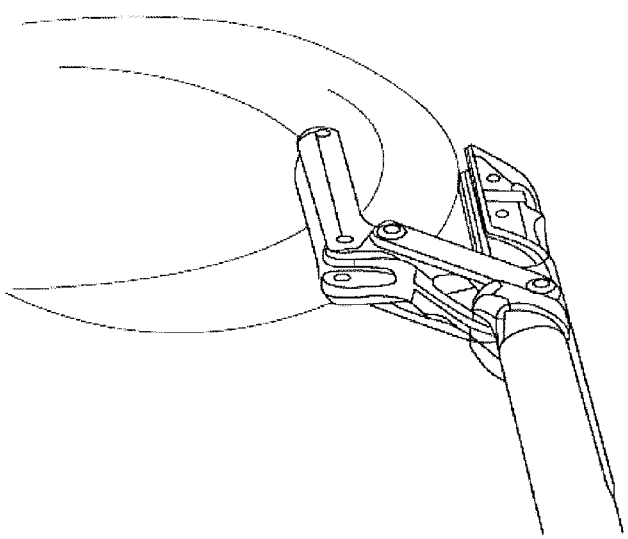
FIG. 49 illustrates one example of meniscus surgery using the suture passer device of the present invention.
Figure 50A:
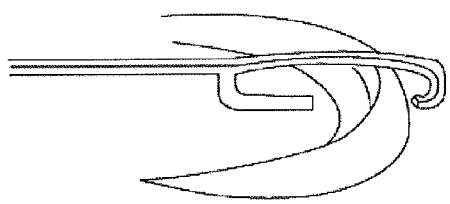
FIGS. 50A-50D illustrate yet another embodiment of meniscus surgery, whereby suture is passed from an anteromedial or anterolateral portal using the suture passer device of the present invention.
Figure 50C:
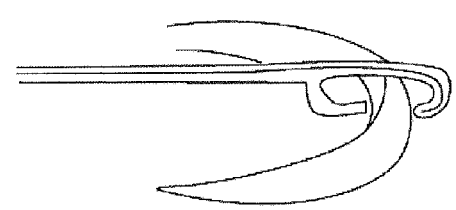
Figure 50B:
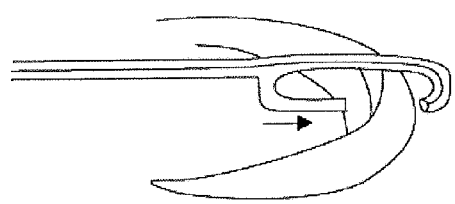
Figure 50D:
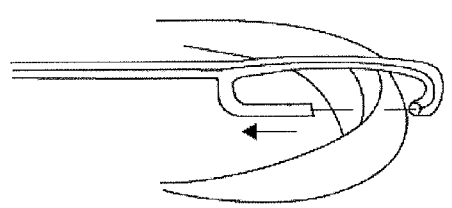

An arthroscope may be inserted through a standard anteromedial or anterolateral portal and the knee joint is distended with saline in standard fashion. A posteromedial posterolateral portal site may be created and the suture passing device may be placed into the joint. The jaws of the suture passing device may open and be placed around the peripherally torn meniscus in such a fashion that the tear is spanned by the jaws in an approximately perpendicular fashion as illustrated in FIG. 49. The meniscus capsule is slightly depressed by the capsular sided jaw to allow good purchase across the tear. The tissue penetrator may be, in one embodiment, passed from the first jaw to the second jaw with the suture. Alternatively, in another embodiment, the suture shuttle may be passed across the meniscal tear via its reversible attachment to the tissue penetrator, while the tissue penetrator is not released from the upper jaw. A knot may then be tied and the meniscus hence repaired. An alternate design embodiment may allow passage of suture from the anteromedial or anterolateral portal, as illustrated in FIGS. 50A-D.

2. ACL Repair and Reefing

Figure 51:
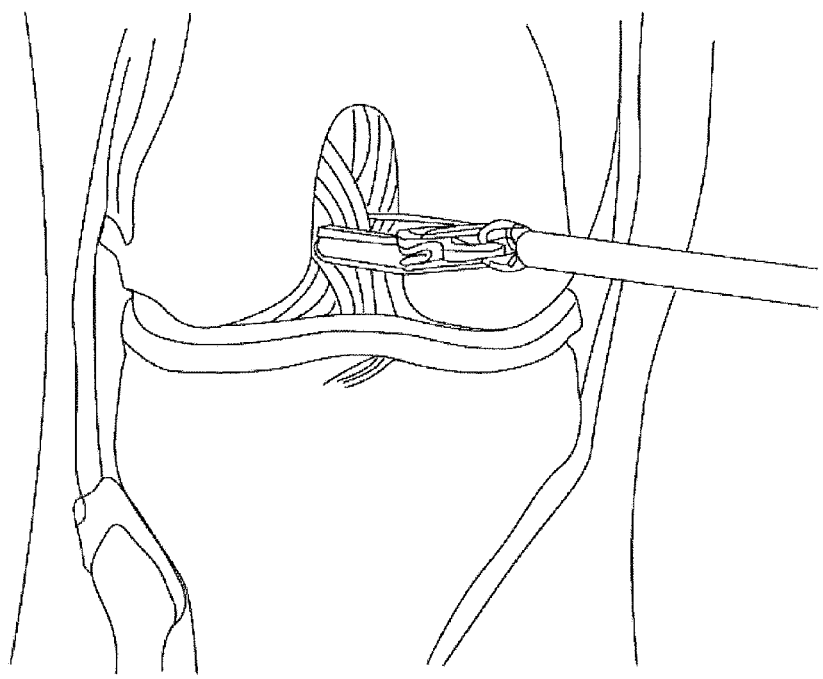
FIG. 51 illustrates one example of anterior cruciate ligament surgery using the suture passer device of the present invention.

Standard anteromedial and anterolateral arthroscopic knee portals may be established and the camera and the suture passing device may be inserted into the joint. The parallel jaws may be open and may be moved into position around the attenuated (post traumatically healed in an elongated state) anterior cruciate ligament, as is illustrated in FIG. 51. The tissue penetrator may then be deployed from the first jaw to interact with the second jaw, thereby passing the shuttle and/or suture across the ligament. The distal end of the suture passer may then be moved to a different position on the ligament and the shuttle and/or suture may then be passed back from the second jaw to the first, thereby contacting the tissue penetrator once again. The suture may be tied by alternating the suture end between the jaws in standard knot tying fashion. The procedure is repeated until the ACL is of the appropriate length and tension.

3. Medial Patellofemoral Ligament Reefing

The arthroscope may be inserted through a standard inferolateral portal and the knee joint is distended with saline in standard fashion. The inferomedial portal is then created and the suture passing device may be inserted into the patellofemoral joint space. The attenuated medial patellofemoral ligament is identified. Sutures may be arthroscopically placed across the length of the ligament with the suture passing device alternating the shuttle and/or suture between the first and second jaws. Knots may be tied with the device by placing the free end of suture between the jaws and passing the shuttle and/or suture from the first to the second jaw. This may be repeated after moving the jaws into standard simple knot forming positions and the knot is cinched by moving the distal end of the passer away from the suture site while holding tension on the opposite suture limb. This may be repeated until about 3-4 hitches are placed, and then the free ends are cut. This process may be repeated as necessary until the ligament is shortened, reefed, imbricated, or the like to the desired length and tension. Lateral patellar glide is then checked and confirmed to be decreased.

4. Medial Patellofemoral Ligament Repair

The arthroscope may be inserted through a standard inferolateral portal and the knee joint is distended with saline in standard fashion. The inferomedial portal is then created and the suture passing device may be inserted into patellofemoral joint space. The edges of the torn medial patellofemoral ligament are identified and the suture passer jaws may be approximated around the medial aspect of the torn leading edge of the ligament. A horizontal mattress or simple type suture pattern, for example, may be passed arthroscopically with the suture passer device by passing the shuttle and/or suture from the first jaw to the second jaw. The lateral leading edge of the torn medial patellofemoral ligament is then identified and the device may be used to pass the shuttle and/or suture from the second jaw back to the first jaw, and the knot is tied to secure the repair. This process may be repeated until the two ends of the ruptured ligament are reapproximated and hence repaired.

5. Minimally Invasive Achilles Tendon Repair

Figure 52:
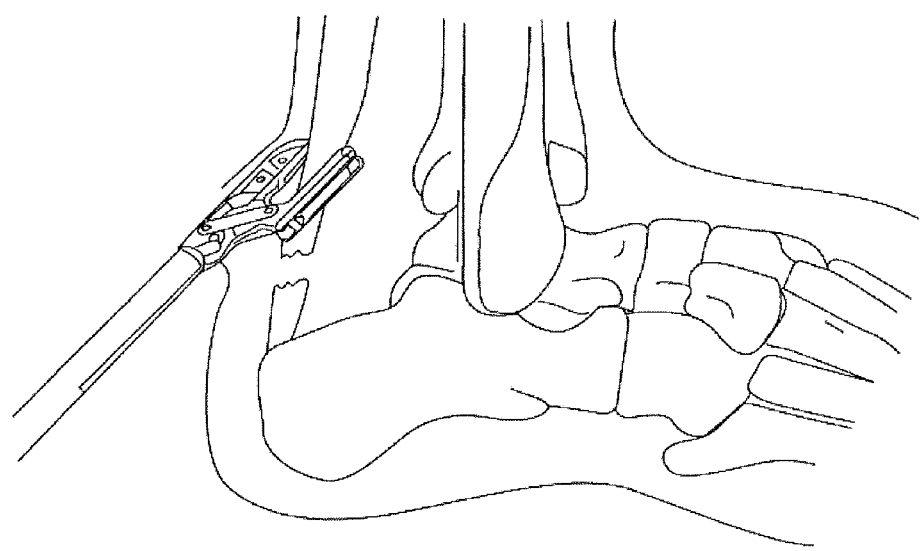
FIG. 52 illustrates one example of Achilles tendon repair using the suture passer device of the present invention.

An about 1-2 cm transverse or vertical incision, for example, may be made in close approximation to the site of rupture of the Achilles tendon. The peritendon is identified and separated from the torn tendon. The edges of the tear are debrided and prepared in standard fashion. The skin and soft tissues may be gently retracted to allow insertion of the suture passing device. The suture passer may be slid underneath the peritendon and the jaws are opened and approximated around the leading edge of the proximal stump of the torn Achilles tendon, as illustrated in FIG. 52. A horizontal mattress or simple type suture pattern, for example, may be passed with the suture passer device by passing the shuttle and/or suture from the first jaw to the second jaw, moving to an alternate location on the same tendon fragment, and then passing from second jaw to first jaw. This process is repeated on the distal tendon stump. The two ends of the ruptured ligament are then reapproximated by tying the placed sutures together at the rupture site.

6. Superior Labrum Anterior Posterior Repair

Figure 53:
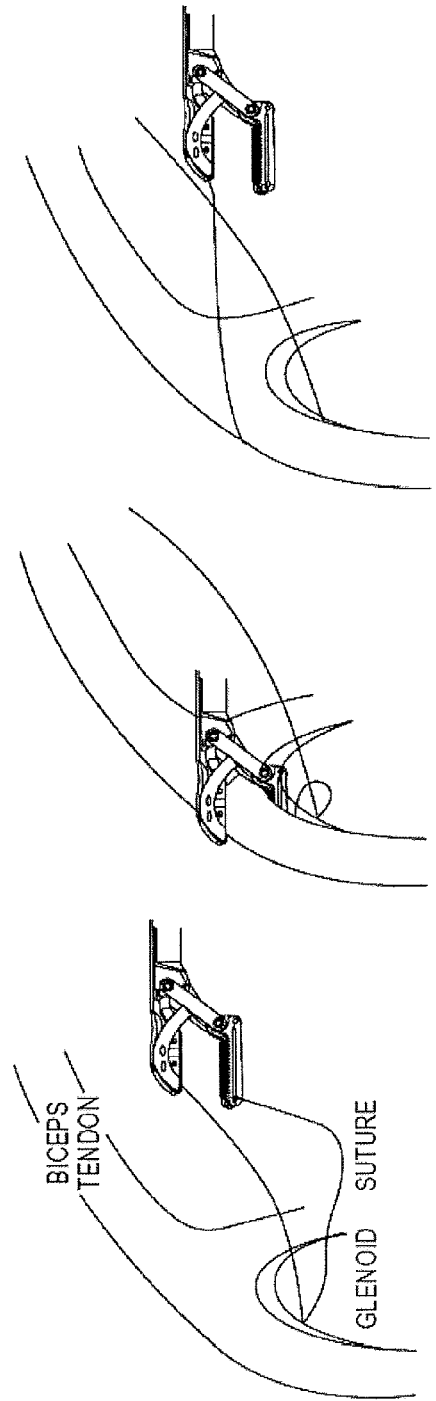
FIGS. 53A-53C illustrates one example of a superior labrum anterior posterior repair using the suture passer device of the present invention.

A posterior shoulder portal may be created for camera placement in standard fashion. A standard anterior portal may be made just superior to the subscapularis tendon and an about 8 mm cannula is placed into the shoulder joint. A standard labral repair suture anchor is placed into the superior glenoid rim in the appropriate position for the repair. One limb of the suture is then brought out of the anterior portal with a crochet hook. The suture passer device may then be loaded with the free end of the suture and inserted through the cannula. The jaws are approximated around the superior labral tear as depicted in FIGS. 53A-C. The suture may then be passed from the first jaw to the second jaw. The suture may then either be tied using the suture passer by alternating the shuttle and/or suture between the jaws or it can be tied using standard sliding knots and a knot pusher.

Figure 54:
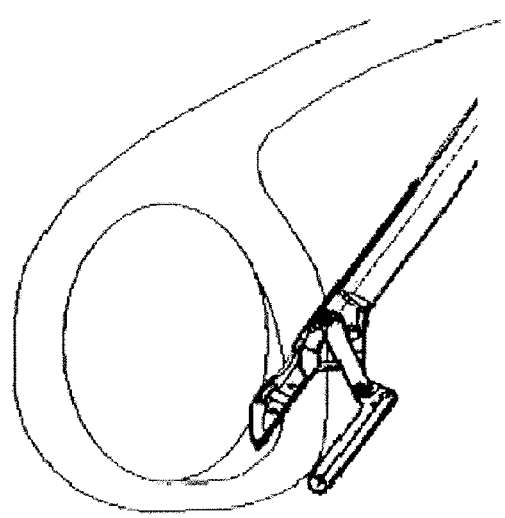
FIG. 54 illustrates one example of labral repair using the suture passer device of the present invention.

7. Arthroscopic Bankart Repair and Capsular Shift for Glenohumeral Labral Repair: Anterior Inferior or Posterior Inferior Standard shoulder arthroscopy portals may be created and the suture passer device may be inserted into the glenohumeral joint. A suture anchor may be placed at either the 7 or 5 o'clock position on the glenoid rim. One limb of suture from this anchor may then be brought out through a cannula and loaded into the suture passer device. The unstable inferior labral tissue and capacious capsule may be grasped by the suture passer device and the tissue penetrator may then be deployed sending the shuttle and/or suture through the desired tissue from the first jaw to the second jaw, as illustrated in FIG. 54. The suture is then tied to the other suture limb in standard labral repair fashion, 8. Arthroscopic Biceps Tenodesis A standard shoulder arthroscopy is performed. The jaws of the suture passer may be placed around the biceps tendon and the shuttle and/or suture is passed back and forth across the tendon. The biceps is then cut from its superior labral attachment and tenodesed in standard fashion.

9. Arthroscopic Hip Labral Repair

Standard hip arthroscopy portals are created. The hip labral tear is evaluated and a portal may be created to maximize positioning of the cannula for insertion of the suture passer. A suture anchor is placed in the acetabular rim at the level of the labral tear in standard fashion. The passer may be loaded with a free end from the anchor and the jaws may be placed around the torn labrum. The shuttle and/or suture may be passed from the first jaw to the second jaw through the labral tissue. The suture ends are tied in standard fashion.

10. Arthoroscopic Brostrom for Ankle Ligament Instability

Standard ankle arthroscopy portals are created. The suture passer device may be inserted into the ankle joint and the attenuated lateral ankle capsule and calcaneofibular ligament are identified. Multiple sutures may then be passed through the ligament and capsule by alternating the shuttle and/or suture from the first jaw to the second jaw and back to the first, as necessary. As standard knots may be tied the CFL and capacious capsule are tightened to the appropriate tension and the lateral ankle hence stabilized.

11. Arthroscopic Triangular Fibrocartilagenous Complex Repair (TFCC Repair)

Standard wrist arthroscopy portals are created and the arthroscope may be inserted into the wrist and directed toward the ulnar side. A small-sized embodiment of the suture passer device may then be inserted into the wrist joint. The tear in the TFCC may then be grasped with the suture passer device and suture may be passed from the first to the second jaw. The distal end of the passer may then be moved to surround the opposite side of the TFCC tear and the tissue penetrator may again be deployed, this time sending the suture from the second jaw to the first. The suture is tied in standard arthroscopic knot tying fashion. This pattern is repeated until the TFCC tear is completely repaired.

12. Medial Row Modified Masson-Alien Double Row Rotator Cuff Repair

Figure 55A:
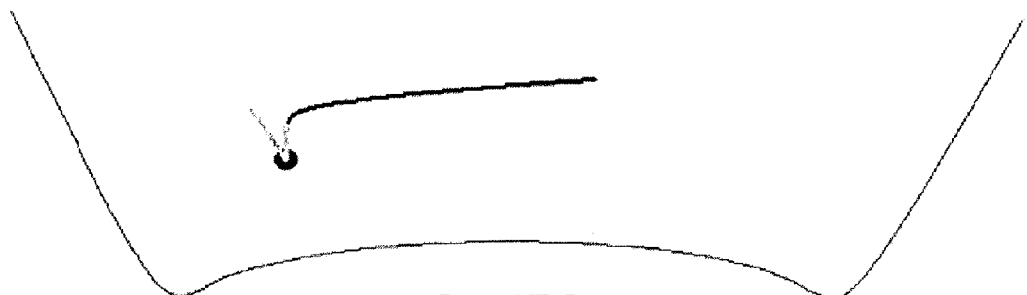
FIGS. 55A-55E illustrate a modified Masson-Allen Double Row suture knot for rotator cuff repair using the suture passer device of the present invention.
Figures 55B, 55C:
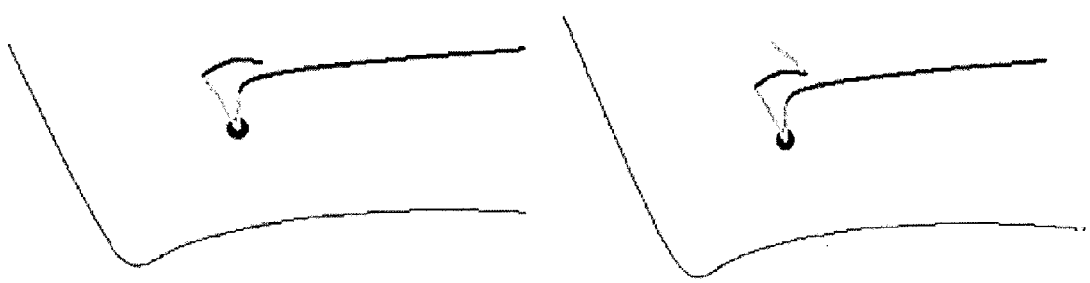
Figures 55D, 55E:
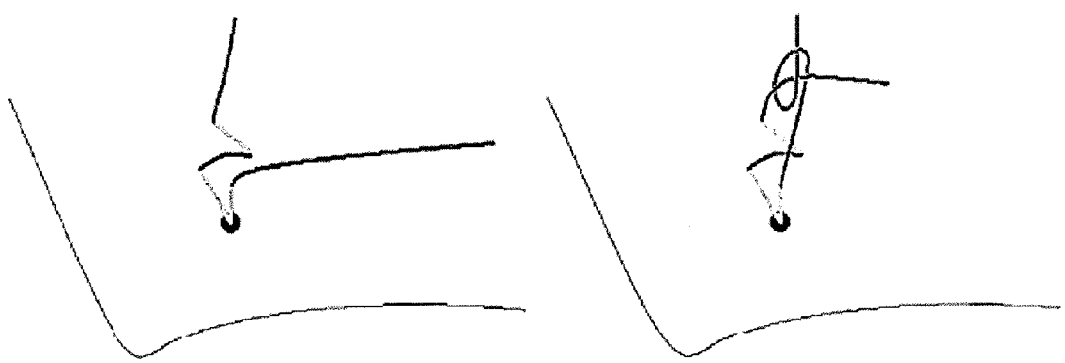
Figure 56A:
FIGS. 56A-56C illustrate a further step, following FIGS. 55A-55E, in which the remaining strands of suture are tied to at least one knotless suture anchor.
Figure 56B:
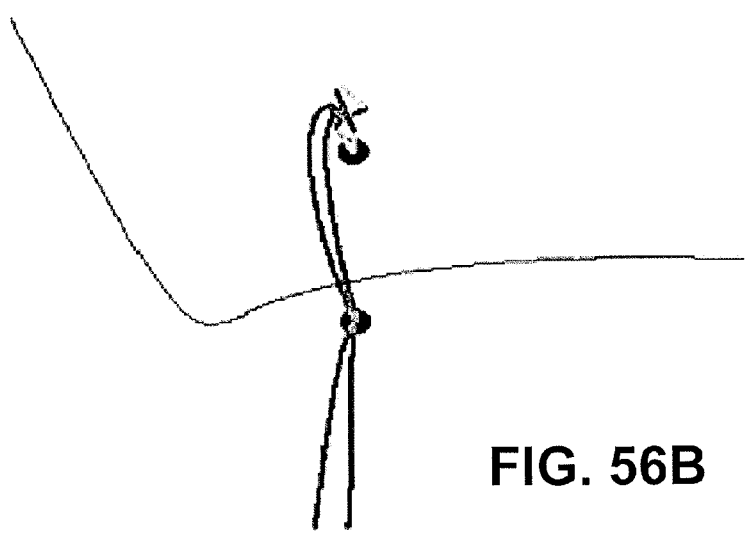
Figure 56C:
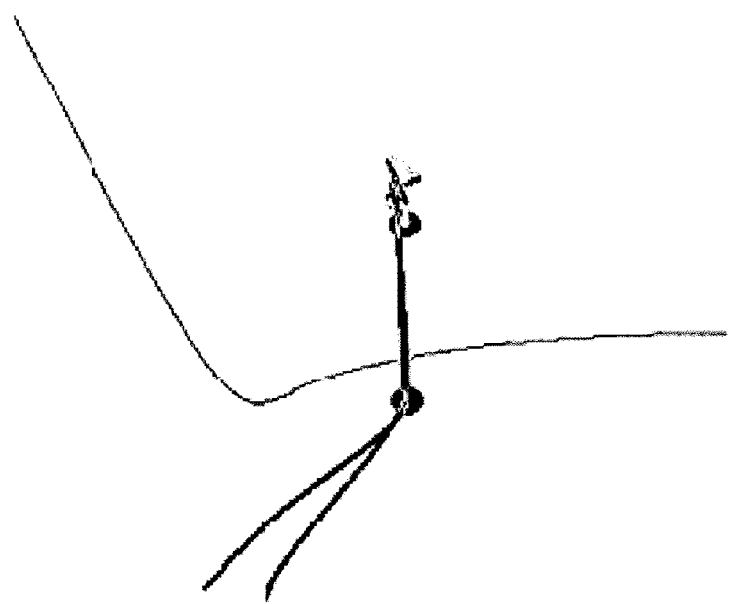
Figure 59B:
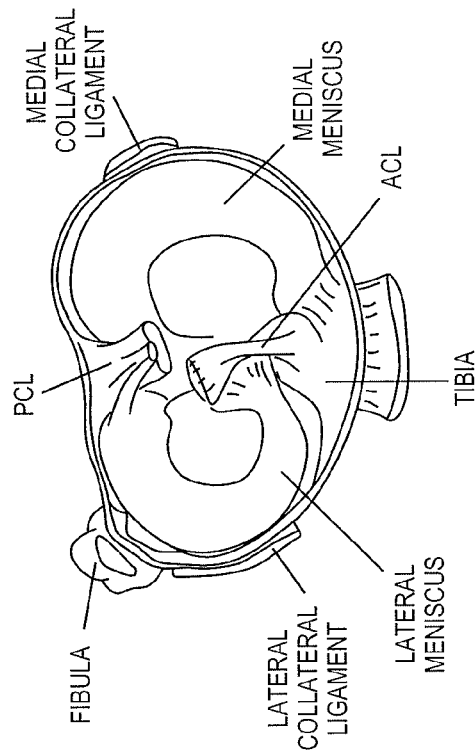
FIGS. 59A and 59B illustrate the anatomy of the meniscus.
Figure 59A:
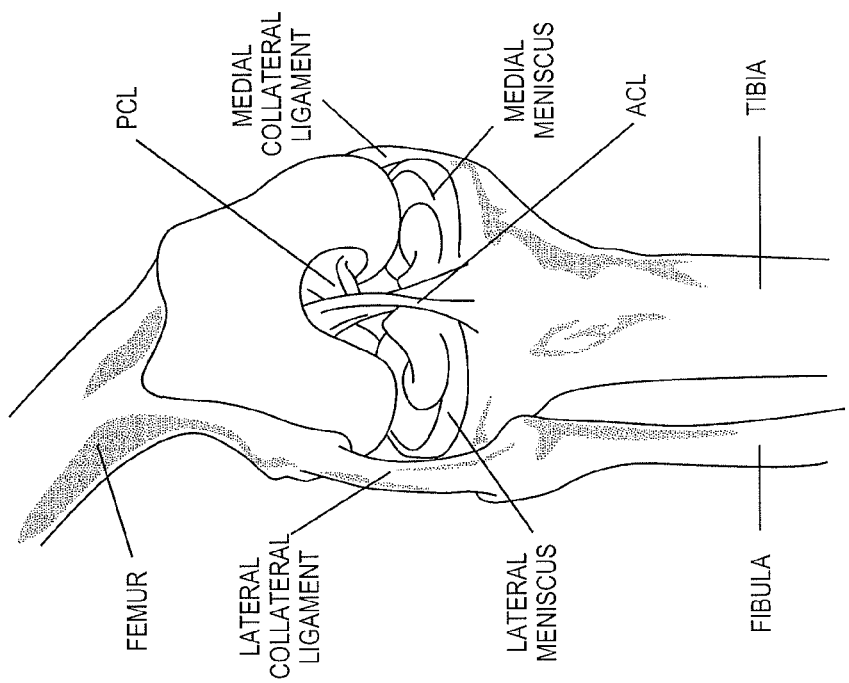
Figure 60:
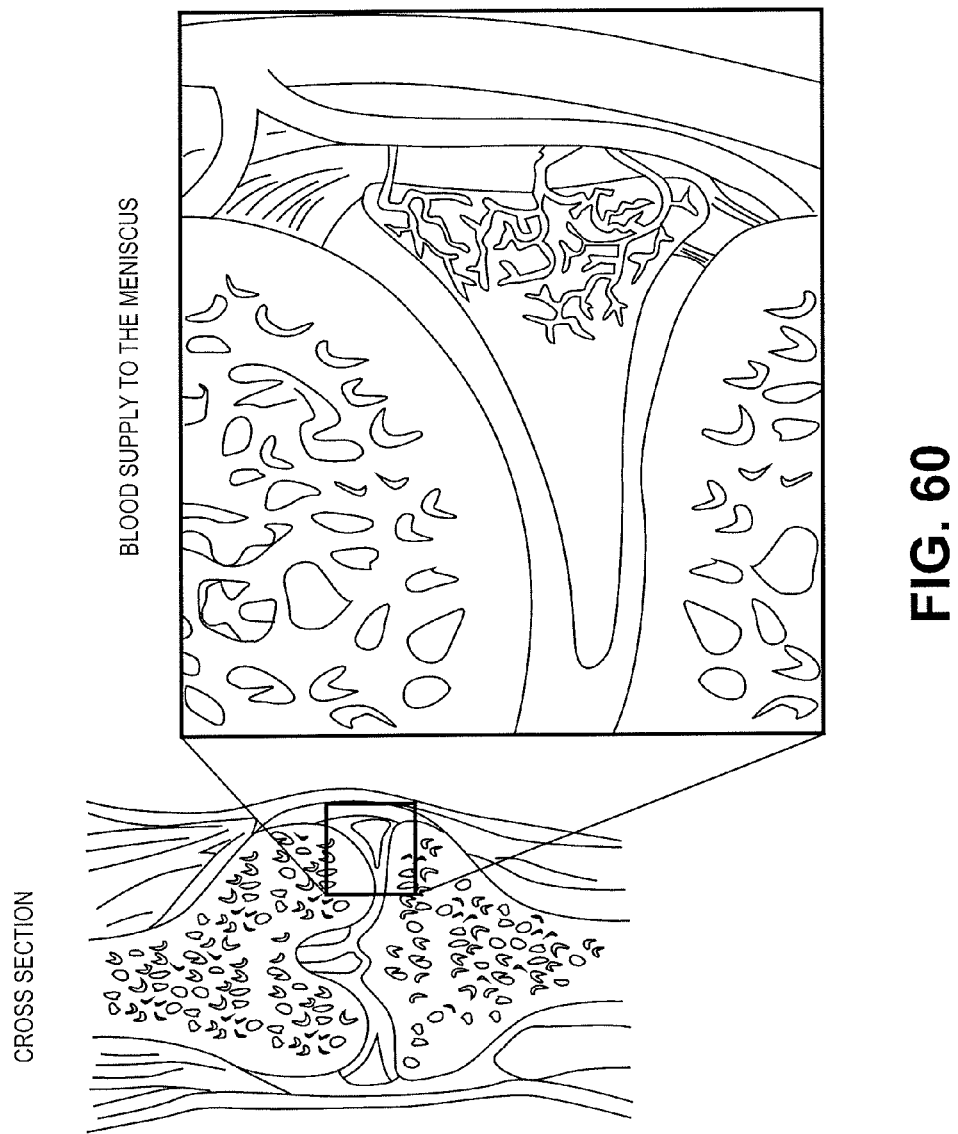
FIG. 60 illustrates the anatomy of the meniscus, including the capsule and associated vascular tissue.
Figure 61:
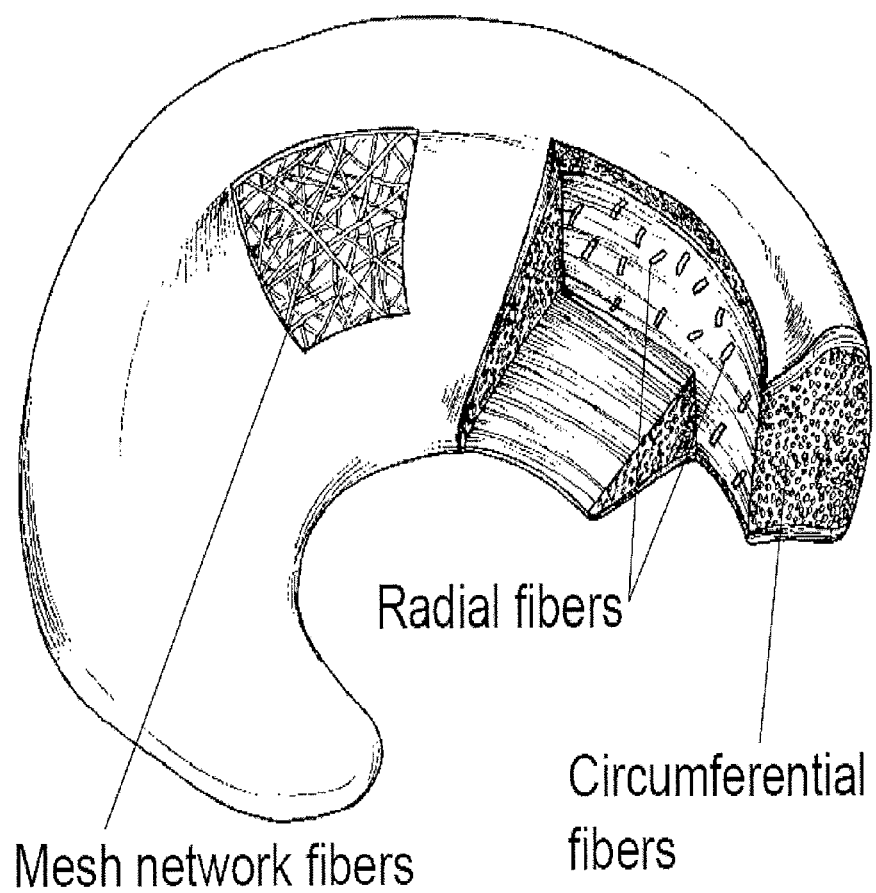
FIG. 61 illustrates the structure of a meniscus.

Standard shoulder arthroscopy portals are created and the camera is inserted into the subacromial space. A standard subacromial decompression is performed. A suture anchor may then be placed at the medial aspect of the greater tuberosity in close proximity to the humeral head cartilaginous surface. One limb of suture from the anchor may then be loaded into the suture passer device and the device may be inserted into the joint. The jaws may be placed around the leading edge of the rotator cuff tear and the tissue penetrator may be deployed to send the shuttle and/or suture from the first jaw to the second jaw. This passed suture end is then removed from the subacromial space through an anterior portal, illustrated in FIG. 55A. The suture passer device may then be loaded with the other suture strand from the medial row anchor and the device is reinserted into the subacromial space. The jaws may again be approximated around the leading edge of the torn rotator cuff tendon and the suture is passed from the first jaw to the second jaw, as in FIG. 55B. The distal end of the suture passer device may then be moved to the right or left and the tissue penetrator may be re-deployed to send the suture from the second jaw to the first, as illustrated in FIG. 55C. The distal end of the suture passer device may then be moved into a position that is medial to and in between the previous passes and the suture may again be passed from the first jaw to the second jaw, as in FIG. 55D. The knot may be tied using the suture passer device or using standard knot tying techniques, as those illustrated in FIGS. 55E and 56A. The two strands of remaining suture from the tied knot may then be brought laterally and tied down to a lateral row knotless anchor using standard techniques, such as those in FIGS. 56B-C.

13. Spinal Surgery

Dural tears are a common complication during spine surgery. If improperly closed they can lead to the development of dural-cutaneous fistulas, pseudomeningocele, and meningitis. Dural tear that are discovered or caused intraoperatively are best treated by direct repair, a fascial graft, or both.

Annular incisions are commonly made during microdiscectomy to allow access to the nuclear material. The annular incision is uncommonly closed secondary to difficulty manipulating suture and the tissue penetrator in this space. Sewing the annular incision would likely decrease recurrence rates of disc herniation. Thus a continuous suture passer would be useful to repair this incision.

A standard microdiscectomy posterior approach to the spine is performed. As FIGS. 57-58 illustrate, the jaws of the suture passer device may be placed around the dura (or annulus) at one side of the tear. The suture may be passed from the first jaw to the second jaw. The jaws may then be positioned around the contralateral side of the tear, and the suture may be passed from the second jaw to the first jaw. A standard knot may then be tied. The procedure may be repeated until the tear is completely repaired.

Figure 64A:
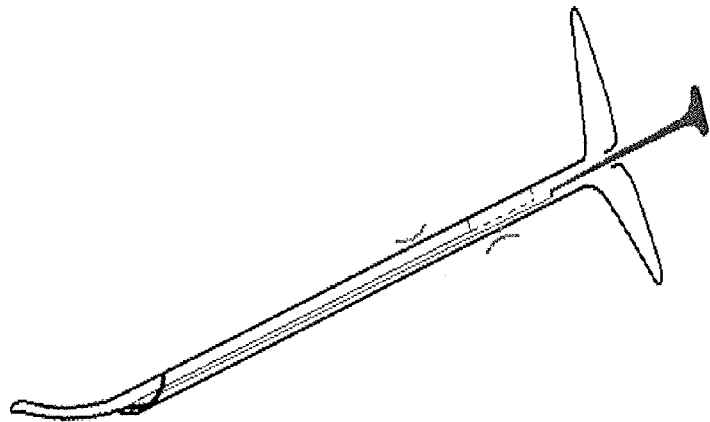
FIGS. 64A and 64B illustrate one variation of a meniscus repair suture passer.
Figure 64B:
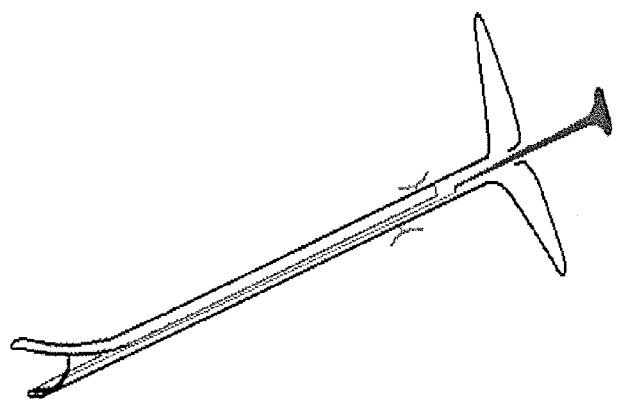

FIGS. 64A-64B illustrate another variation of a suture passer device particularly useful in repairing a meniscus, in which the upper and lower arms may be moved axially and individually locked into position.

The various configurations of the upper and lower arm relative to each other in one variation of a meniscus repair suture passer device are illustrated in FIGS. 64C to 64H. For example, FIGS. 64C and 64D illustrate two perspective views of one variation of a meniscus repair suture passer device 6401 having an elongate first arm 6403 that is axially movable (in the distal/proximal long axis of the device 6405) relative to the rest of the device, including a second arm 6407. The elongate second arm 6407 extends adjacent to the first arm along the long axis 6405 of the device. The elongate second arm also includes a bent distal end region 6409 that may be bent at an angle relative to the long axis 6405 of the device, as shown. The distal tip of this distal end region is atraumatic, and is shown as substantially blunt. In FIGS. 64C and 64D, the first arm is retracted proximally so that it does not form a distal opening in this position.

Figure 64G:
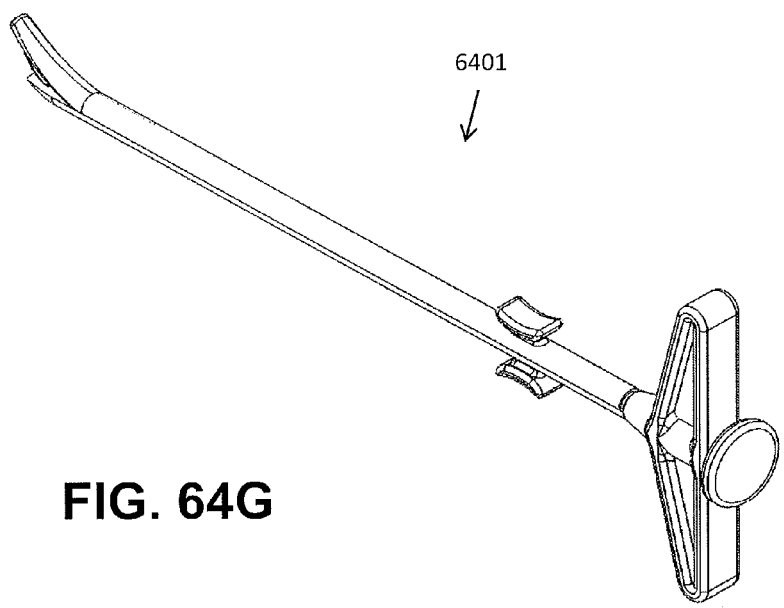
FIGS. 64G and 64H show a meniscus repair suture passer after the lower (straight) arm has been extended and the curved tissue penetrator has been extended.
Figure 64H:
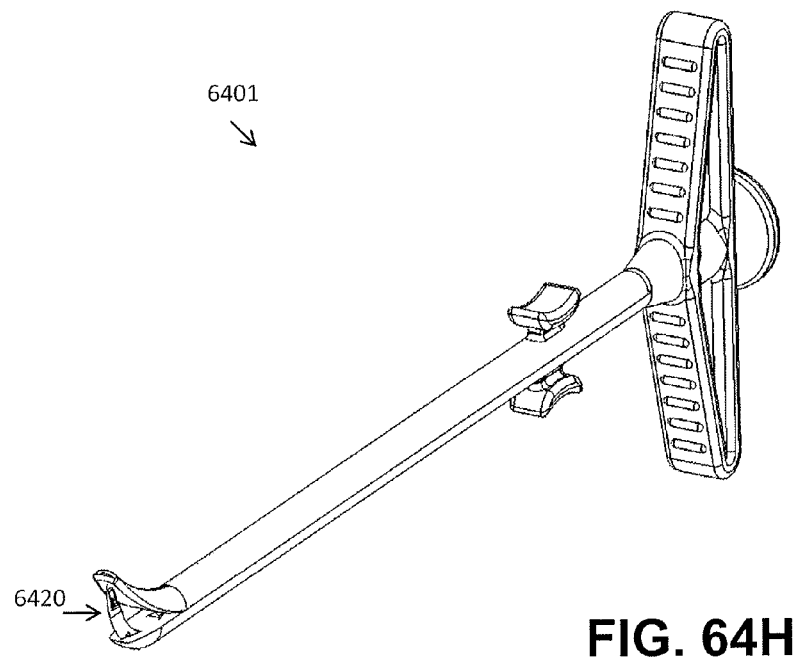

FIGS. 64E and 64F illustrate an extended position in which the distal end region of the first arm 6411 has been extended distally towards the distal end region 6409 of the upper arm (second arm 6407). The distal end regions of the first and second arms 6409, 6411 have formed a distal opening 6414 between the first and second arms. The exit for the tissue penetrator is visible as an opening 6418 in the lower arm 6403 in FIG. 64F. FIGS. 64G and 64H show the same views of the suture passers 6401 shown in FIGS. 64E and 64F, but with the tissue penetrator 6420 extended from the first (lower) arm 6403. The tissue penetrator may extend in a curved path through the tissue between the first and second arms, as shown. All of the devices shown in FIGS. 64A-64H include a handle. In FIGS. 64G and 64H a control on the handle is shown as depressed, actuating the extension of the tissue penetrator 6420 between the upper and lower arms.

Figures 62A, 62B, 62C, 62D, 62E:
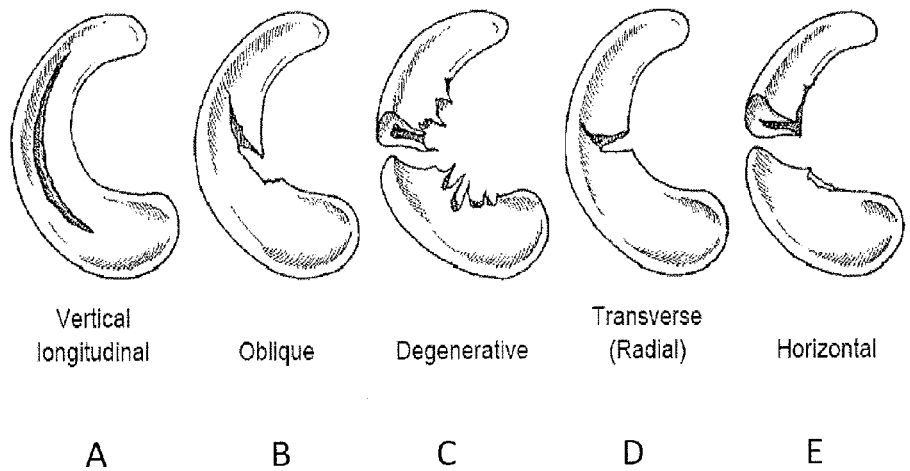
FIGS. 62A-62E illustrate various tear patterns that may be repaired using the invention described herein.
Figure 63A:
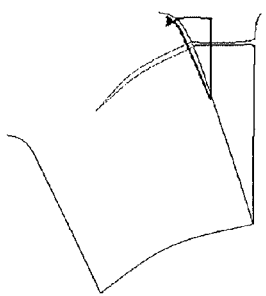
FIGS. 63A-63C illustrate meniscus repair using prior art devices.
Figure 63C:
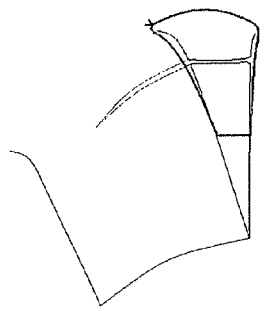
Figure 63B:
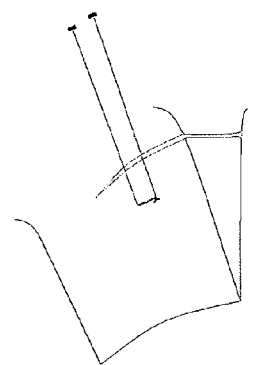
Figure 63D:
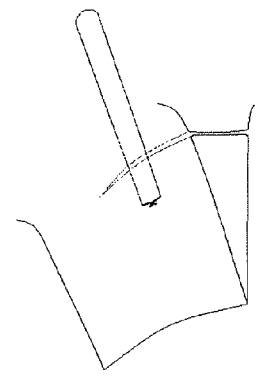
FIG. 63D illustrates meniscus repair using a device as described herein.

As described, the suture devices described herein may be used to repair longitudinal meniscus tears (e.g., FIG. 62A). The configuration of the arms in some variations (which move axially in the long axis of the device) and the tissue penetrator element (which is configured to extend substantially perpendicular to the lower arm), of the devices described herein may also be used to repair radial or even oblique tears in the meniscus (e.g., FIGS. 62B-62E). Repair of such tears is typically difficult or impossible using other prior art devices. Repair of such radial and oblique peripheral tears is made possible because the suture passer described herein may pass suture from the superior (upper) to the inferior (lower) surface of the meniscus (or vice versa). Repair of radial and oblique tears is also made simpler and more convenient because the meniscus suture passer devices described herein may continuously pass a suture between the upper and lower arms without having to be removed from the tissue.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What I claim is:

1. A method of repairing or reconstructing a meniscus of a knee, the method comprising:
arthroscopically positioning a first arm of a suture passer on a superior side of the meniscus before positioning a second arm of the suture passer on an inferior side of the meniscus, positioning the second arm on the inferior side of the meniscus so that the meniscus is within a distal-facing opening of the arms, wherein the suture passer has an elongate body having a proximal to distal long axis, and at least one of the first or second arms of the suture passer is axially movable relative to the other arm in the proximal to distal direction of the long axis;
passing a first limb of suture through the meniscus by extending a tissue penetrator between the distal-facing opening formed by the first and second arms, along a first path through the meniscus and retracting the tissue penetrator back through the meniscus along the first path;
repositioning the suture passer relative to the meniscus; and
passing a second limb of suture through the meniscus by extending the tissue penetrator between the distal-facing opening formed by the first and second arms, along a second path through the meniscus and retracting the tissue penetrator back through the meniscus along the second path.

2. The method of claim 1, wherein passing the suture through the meniscus by extending the tissue penetrator between the distal-facing opening formed by the first and second arms along the first path through the meniscus comprises engaging the suture with the tissue penetrator proximal to a distal tip of the tissue penetrator.

3. The method of claim 1, wherein repositioning the suture passer relative to the meniscus comprises moving the suture passer relative to the meniscus without removing the first and second arms of the suture passer from around the meniscus.

4. The method of claim 1, further comprising minimally invasively accessing the meniscus to position the suture passer.

5. The method of claim 1, wherein the first and second paths through the meniscus are curved paths.

6. The method of claim 1, wherein retracting the tissue penetrator back through the meniscus along the first path comprises retracing the tissue penetrator back into the first arm.

7. The method of claim 1, further comprising pulling the suture through the meniscus when retracting the tissue penetrator back through the meniscus.

8. The method of claim 1, wherein repositioning the suture passer comprises repositioning the suture passer so that at least one of the first or second arms of the suture passer moves from one side of a tear in the meniscus to another side of the tear.

9. The method of claim 1, wherein positioning the first arm and the second arm comprises pushing against the meniscus capsule with one of the first arm or second arm.

10. The method of claim 1, further comprising inserting the suture passer into the patient's knee with either the first or second arms proximally retracted so that the suture passer does not have a distal-facing opening between the first arm and the second arm of the suture passer.

11. The method of claim 1, further comprising inserting the suture passer into the patient's knee and then forming the distal-facing opening of the suture passer at the distal end of the suture passer by distally extending either the first or second arm axially relative to the other arm.

12. A method of repairing or reconstructing a torn meniscus of a knee using a suture passer having an elongate body with a proximal to distal long axis, a first arm and a second arm, wherein the second arm is axially movable relative to the first arm in the proximal to distal direction of the long axis, the method comprising:
arthroscopically positioning the first arm of the suture passer on a superior side of the meniscus;
axially sliding the second arm of the suture passer on to an inferior side of the meniscus after positioning the first arm so that the meniscus is at least partially within a distal-facing opening formed between the first and second arms;
passing a first limb of suture through the meniscus by extending a tissue penetrator across the distal-facing opening, along a first path through the meniscus and retracting the tissue penetrator back through the meniscus along the first path;
repositioning at least one arm of the suture passer relative to the meniscus;
passing a second limb of suture through the meniscus by extending the tissue penetrator across the distal-facing opening, along a second path through the meniscus and retracting the tissue penetrator back through the meniscus along the second path.

13. The method of claim 12, wherein repositioning at least one arm of the suture passer relative to the meniscus comprises moving one arm of the suture passer relative to the other arm.

14. The method of claim 12, further comprising minimally invasively accessing the meniscus to position the suture passer.

15. The method of claim 12, further comprising pulling the suture through the meniscus.

16. The method of claim 12, wherein retracting the tissue penetrator back through the meniscus comprises pulling the suture through the meniscus.

17. A method of arthroscopic meniscus repair or reconstruction using a suture passer having an elongate body with a proximal to distal long axis, a first arm and a second arm, wherein the second arm is axially movable relative to the first arm in the proximal to distal direction of the long axis, the method comprising:
arthroscopically accessing a meniscus with the suture passer wherein the second arm is retracted proximally relative to the elongate body of the suture passer so that it does not form a distal-facing opening with the first arm;
extending the second arm distally, relative to the first arm, after positioning the first arm on the meniscus, by sliding the second arm distally in the long axis so that the arms of the suture passer form a distal-facing opening around the meniscus;
extending a tissue penetrator along a first path through the meniscus and retracting the tissue penetrator back through the meniscus along the first path, to pass a first limb of suture through the meniscus;
repositioning at least one arm of the suture passer relative to the meniscus; and extending the tissue penetrator along a second path through the meniscus and retracting the tissue penetrator back through the meniscus along the second path, to pass a second limb of suture through the meniscus.

* * * * *

UNITED STATES PATENT AND TRADEMARK OFFICE
CERTIFICATE OF CORRECTION

PATENT NO. : 8,663,253 B2
APPLICATION NO. : 13/090089
DATED : March 4, 2014
INVENTOR(S) : Justin D. Saliman It is certified that error appears in the above-identified patent and that said Letters Patent is hereby corrected as shown below:

In the Specification

Column 1, line 56; after "joint" and before "the knee).", insert --(e.g.,--.

Column 2, line 2; after "meniscus." and before "this may", delete "White" and insert --While--.

Column 7, line 45; after "or the" and before "general", delete "like, in" and insert --like. In--.

Column 7, line 51; after "the uterus," and before "tho-", delete "hemonhoidectomy," and insert --hemorrhoidectomy,--.

Column 8, line 26; after "forms a", delete "FIG. 8" and insert --Figure 8.--.

Column 17, line 17; after "respect to the" and before "jaw 21,", delete "tower" and insert --lower--.

Column 23, line 20; after "open and" and before "in parallel.", delete "dose" and insert --close--.

Column 23, line 35; after "both the" and before "jaw 21", delete "tower" and insert --lower--.

Column 23, line 50; after "element 18 and the" and before "19.", delete "tower jaw 21 and pivot aim" and insert --lower jaw 21 and pivot arm--.

Column 26, line 15; after "pulley" and before "may be", delete "333," and insert --333',--.

Column 26, line 24; after "be too" and before "However,", delete "tong." and insert --long.--.

Column 26, line 32; after "within" and before "retainer", delete "shuffle" and insert --shuttle--.

Column 28, line 22; after "latch" and before "may be", delete "52" and insert --52'--.

Signed and Sealed this
Ninth Day of December, 2014

Michelle K. Lee
*Deputy Director of the United States Patent and Trademark Office*

CERTIFICATE OF CORRECTION (continued)
U.S. Pat. No. 8,663,253 B2

Column 28, line 44; after "of the" and before "addition,", delete "jaws) in" and insert --jaws). In--.

Column 31, line 27; after "Masson-" and before "Double", delete "Alien" and insert --Allen--.